United States Patent
Kitada et al.

(10) Patent No.: US 12,062,787 B2
(45) Date of Patent: Aug. 13, 2024

(54) SECONDARY BATTERY

(71) Applicant: MURATA MANUFACTURING CO., LTD., Kyoto (JP)

(72) Inventors: Keitaro Kitada, Kyoto (JP); Futoshi Sato, Kyoto (JP); Takaaki Matsui, Kyoto (JP); Taichi Kogure, Kyoto (JP); Aya Mashiko, Kyoto (JP); Yoshifumi Shimizu, Kyoto (JP); Kazuki Honda, Kyoto (JP); Yuta Hirano, Kyoto (JP); Shinji Hatake, Kyoto (JP); Naoko Yamakawa, Kyoto (JP); Moriaki Okuno, Kyoto (JP); Masahiro Miyamoto, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 635 days.

(21) Appl. No.: 17/307,661

(22) Filed: May 4, 2021

(65) Prior Publication Data
US 2021/0288322 A1    Sep. 16, 2021

Related U.S. Application Data

(63) Continuation of application No. PCT/JP2019/046743, filed on Nov. 29, 2019.

(30) Foreign Application Priority Data

Nov. 30, 2018 (JP) .................................. 2018-225937
Nov. 30, 2018 (JP) .................................. 2018-225939
(Continued)

(51) Int. Cl.
*H01M 4/525*    (2010.01)
*C07D 319/06*   (2006.01)
(Continued)

(52) U.S. Cl.
CPC .......... *H01M 4/525* (2013.01); *C07D 319/06* (2013.01); *C08F 214/22* (2013.01); *H01M 4/131* (2013.01);
(Continued)

(58) Field of Classification Search
CPC ...... H01M 4/525; H01M 4/131; H01M 4/133; H01M 4/134; H01M 4/364; H01M 4/386;
(Continued)

(56) References Cited

U.S. PATENT DOCUMENTS 9,666,905 B2 *  5/2017  Taeda ................ H01M 10/0569
2006/0222957 A1  10/2006  Hara et al.
(Continued)

FOREIGN PATENT DOCUMENTS

JP   2002252028 A   9/2002
JP   2006313719 A   11/2006
(Continued)

OTHER PUBLICATIONS

English machine translation of JP2016-170937 (application 2015-049168), Japan, 2016.*
(Continued)

*Primary Examiner* — Holly Rickman
(74) *Attorney, Agent, or Firm* — K&L Gates LLP

(57) ABSTRACT

A secondary battery includes a positive electrode, a negative electrode, and an electrolytic solution. The positive electrode includes a lithium-cobalt composite oxide having a layered rock-salt crystal structure. The negative electrode includes graphite. An open circuit potential of the negative electrode measured in a full charge state is from 19 mV to 86 mV. A potential variation of the negative electrode is greater than or equal to 1 mV when the secondary battery is discharged from the full charge state by a capacity corresponding to 1% of a maximum discharge capacity. The
(Continued)

maximum discharge capacity is obtained when the secondary battery is discharged with a constant current from the full charge state until the closed circuit voltage reaches 3.00 V, following which the secondary battery is discharged with a constant voltage of the closed circuit voltage of 3.00 V for 24 hours.

19 Claims, 6 Drawing Sheets

(30) Foreign Application Priority Data

| Nov. 30, 2018 | (JP) | ................. | 2018-225940 |
|---|---|---|---|
| Nov. 30, 2018 | (JP) | ................. | 2018-225942 |
| Nov. 30, 2018 | (JP) | ................. | 2018-225943 |
| Nov. 30, 2018 | (JP) | ................. | 2018-225944 |

(51) Int. Cl.

| *C08F 214/22* | (2006.01) |
|---|---|
| *H01M 4/131* | (2010.01) |
| *H01M 4/133* | (2010.01) |
| *H01M 4/134* | (2010.01) |
| *H01M 4/36* | (2006.01) |
| *H01M 4/38* | (2006.01) |
| *H01M 4/587* | (2010.01) |
| *H01M 4/62* | (2006.01) |
| *H01M 10/0525* | (2010.01) |
| *H01M 10/0567* | (2010.01) |
| *H01M 10/0587* | (2010.01) |
| *H01M 50/414* | (2021.01) |
| *H01M 50/449* | (2021.01) |
| *H01M 50/46* | (2021.01) |
| *H01M 4/02* | (2006.01) |

(52) U.S. Cl.
CPC ........... *H01M 4/133* (2013.01); *H01M 4/134* (2013.01); *H01M 4/364* (2013.01); *H01M 4/386* (2013.01); *H01M 4/587* (2013.01); *H01M 4/623* (2013.01); *H01M 4/625* (2013.01); *H01M 10/0525* (2013.01); *H01M 10/0567* (2013.01); *H01M 10/0587* (2013.01); *H01M 50/414* (2021.01); *H01M 50/449* (2021.01); *H01M 50/461* (2021.01); *H01M 2004/021* (2013.01); *H01M 2300/0025* (2013.01)

(58) Field of Classification Search
CPC ...... H01M 4/587; H01M 4/623; H01M 4/625; H01M 4/366; H01M 4/0404; H01M 50/414; H01M 50/449; H01M 50/461; H01M 50/105; H01M 2004/021; H01M 2300/0025; H10M 10/0525; H10M 10/0567; H10M 10/0587

See application file for complete search history.

(56) References Cited

U.S. PATENT DOCUMENTS

| 2007/0202406 A1 | 8/2007 | Takahashi et al. |
|---|---|---|
| 2012/0231347 A1 | 9/2012 | Hara et al. |
| 2018/0309161 A1 | 10/2018 | Kim et al. |

FOREIGN PATENT DOCUMENTS

| JP | 2007048560 A | 2/2007 |
|---|---|---|
| JP | 2007200821 A | 8/2007 |
| JP | 2009218112 A | 9/2009 |
| JP | 2014526772 | 10/2014 |
| JP | 2016081757 | 5/2016 |
| JP | 2016170937 A | 9/2016 |
| JP | 2017191662 A | 10/2017 |
| JP | 2018166108 | 10/2018 |
| JP | 2018530142 | 10/2018 |
| WO | 2007139130 A1 | 12/2007 |
| WO | 2011145301 A1 | 11/2011 |
| WO | 2014/136648 | 9/2014 |

OTHER PUBLICATIONS

English machine translation of JP2002-252028 ., Japan, 2002.*
English machine translation of JP2016-081757 (application 2014-212858), Japan 2016.*
English machine translation of JP2003-151638 (application 2002-332139), Japan, 2003.*
Japanese Office Action issued Mar. 15, 2022 in corresponding Japanese Application No. 2020-557850.
Chinese Office Action issued Aug. 17, 2023 in corresponding Chinese Application No. 201980072253.0.
Japanese Office Action issued Jun. 27, 2023 in corresponding Japanese Application No. JP2022-127087.
European Search Report issued Jun. 3, 2022 in corresponding European Application No. 19890574.7.
International Search Report for Application No. PCT/JP2019/046743, dated Mar. 3, 2020.
Japanese Office Action issued Nov. 28, 2023 in corresponding Japanese Application No. 2022-127087.

\* cited by examiner

SECONDARY BATTERY

CROSS REFERENCE TO RELATED APPLICATIONS

The present application is a continuation of PCT patent application no. PCT/JP2019/046743, filed on Nov. 29, 2019, which claims priority to Japanese patent application no. JP2018-225942 filed on Nov. 30, 2018, Japanese patent application no. JP2018-225940 filed on Nov. 30, 2018, Japanese patent application no. JP2018-225939 filed on Nov. 30, 2018, Japanese patent application no. JP2018-225944 filed on Nov. 30, 2018, Japanese patent application no. JP2018-225943 filed on Nov. 30, 2018, and Japanese patent application no. JP2018-225937 filed on Nov. 30, 2018, the entire contents of which are being incorporated herein by reference.

BACKGROUND

The present technology relates to a secondary battery.

Various electronic apparatuses such as mobile phones have been widely used. Accordingly, a secondary battery is under development as a power source which is smaller in size and lighter in weight and allows for a higher energy density. The secondary battery includes a positive electrode, a negative electrode, and an electrolytic solution.

Various considerations have been given to a configuration of the secondary battery to improve battery characteristics. Specifically, to achieve a higher energy density (a higher capacity), a charge voltage (a potential of a positive electrode versus a lithium reference electrode) is set to about 4.4 V or higher.

SUMMARY

The present technology relates to a secondary battery.

Electronic apparatuses, on which a secondary battery is to be mounted, are increasingly gaining higher performance and more functions, causing more frequent use of the electronic apparatuses and expanding a use environment of the electronic apparatuses. Accordingly, there is still room for improvement in terms of battery characteristics of the secondary battery.

The present technology has been made in view of such an issue and it is an object of the technology to provide a secondary battery that makes it possible to achieve a superior battery characteristic.

A secondary battery according to an embodiment of the technology includes a positive electrode, a negative electrode, and an electrolytic solution. The positive electrode includes a lithium-cobalt composite oxide represented by Formula (1) and having a layered rock-salt crystal structure. The negative electrode includes graphite. A open circuit potential, versus a lithium reference electrode, of the negative electrode measured in a full charge state is from 19 mV to 86 mV. The full charge state is a state in which the secondary battery is charged with a constant voltage of a closed circuit voltage of higher than or equal to 4.38 V for 24 hours. A potential variation of the negative electrode represented by Formula (2) is greater than or equal to 1 mV when the secondary battery is discharged from the full charge state by a capacity corresponding to 1% of a maximum discharge capacity. The maximum discharge capacity is a discharge capacity obtained when the secondary battery is discharged with a constant current from the full charge state until the closed circuit voltage reaches 3.00 V, following which the secondary battery is discharged with a constant voltage of the closed circuit voltage of 3.00 V for 24 hours.

$$Li_xCo_{1-y}M_yO_{2-z}X_z \tag{1}$$

where:
M represents at least one of titanium (Ti), vanadium (V), chromium (Cr), manganese (Mn), iron (Fe), nickel (Ni), copper (Cu), sodium (Na), magnesium (Mg), aluminum (Al), silicon (Si), tin (Sn), potassium (K), calcium (Ca), zinc (Zn), gallium (Ga), strontium (Sr), yttrium (Y), zirconium (Zr), niobium (Nb), molybdenum (Mo), barium (Ba), lanthanum (La), tungsten (W), or boron (B);
X is at least one of fluorine (F), chlorine (Cl), bromine (Br), iodine (I), or sulfur (S); and
x, y, and z satisfy $0.8<x<1.2$, $0\leq y<0.15$, and $0\leq z<0.05$.

Potential variation (mV) of negative electrode=second negative electrode potential (mV)–first negative electrode potential (mV) (2)

where:
the first negative electrode potential is the open circuit potential, versus the lithium reference electrode, of the negative electrode measured in the full charge state; and
the second negative electrode potential is an open circuit potential, versus the lithium reference electrode, of the negative electrode measured in a state in which the secondary battery is discharged from the full charge state by the capacity corresponding to 1 percent of the maximum discharge capacity.

According to the secondary battery of an embodiment of the present technology, the positive electrode includes the lithium-cobalt composite oxide, the negative electrode includes the graphite, the open circuit potential of the negative electrode measured in the full charge state is from 19 mV to 86 mV, the potential variation of the negative electrode is greater than or equal to 1 mV when the secondary battery is discharged from the full charge state by the capacity corresponding to 1% of the maximum discharge capacity. Accordingly, it is possible to achieve a superior battery characteristic.

It should be understood that effects of the technology are not necessarily limited to those described above and may include any of a series of effects described below in relation to the technology.

DETAILED DESCRIPTION

As described herein, the present disclosure will be described based on examples with reference to the drawings, but the present disclosure is not to be considered limited to the examples, and various numerical values and materials in the examples are considered by way of example.

A description is given first of a secondary battery according to a first embodiment of the technology.

The secondary battery described below is a lithium-ion secondary battery that obtains a battery capacity on the basis of a lithium insertion phenomenon and a lithium extraction phenomenon, as will be described later. The secondary battery includes a positive electrode 13 and a negative electrode 14 (see FIG. 3).

To prevent precipitation of lithium metal on a surface of the negative electrode 14 during charging, an electrochemical capacity per unit area of the negative electrode 14 is greater than an electrochemical capacity per unit area of the positive electrode 13 in the secondary battery.

It should be understood that, however, mass of a positive electrode active material included in the positive electrode 13 is sufficiently greater than mass of a negative electrode active material included in the negative electrode 14 to allow configuration conditions (a negative electrode potential Ef and a negative electrode potential variation Ev), which will be described later, to be satisfied.

Figure 1:
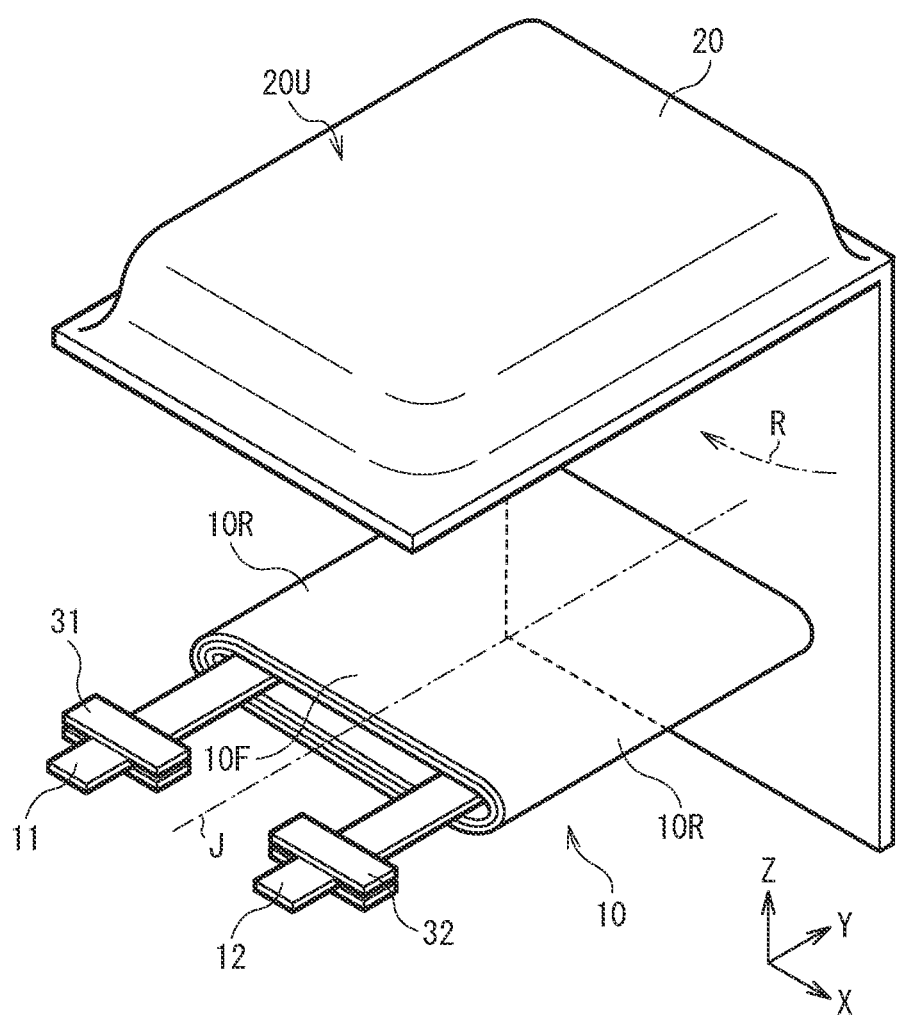
FIG. 1 is a perspective view of a configuration of a secondary battery according to an embodiment of the present technology.
Figure 2:
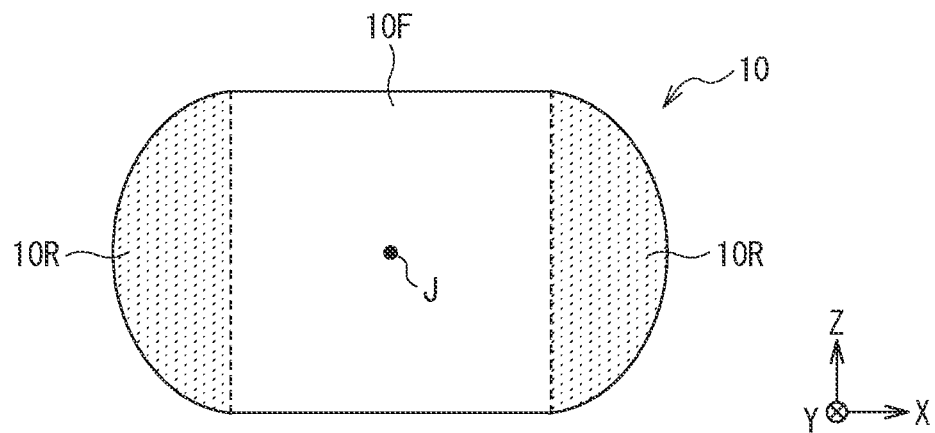
FIG. 2 is a schematic plan view of a wound electrode body illustrated in FIG. 1.
Figure 3:
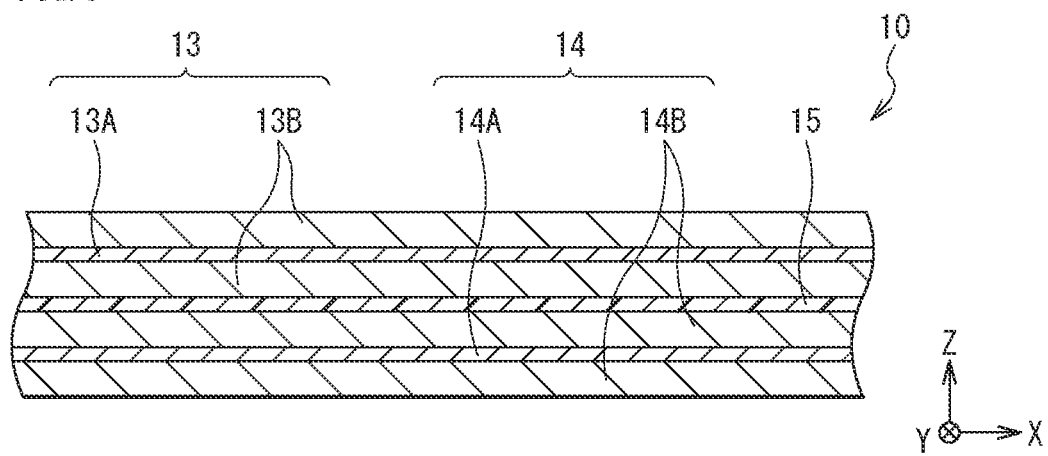
FIG. 3 is an enlarged sectional view of the wound electrode body illustrated in FIG. 1.

FIG. 1 is a perspective view of a configuration of the secondary battery. FIG. 2 is a schematic plan view of a configuration of a wound electrode body 10 illustrated in FIG. 1. FIG. 3 is an enlarged sectional view of the configuration of the wound electrode body 10. It should be understood that FIG. 1 illustrates a state in which the wound electrode body 10 and an outer package member 20 are separated away from each other, and FIG. 3 illustrates only a portion of the wound electrode body 10.

Referring to FIG. 1, the secondary battery includes, for example, the outer package member 20 having a film shape, and the wound electrode body 10 contained in the outer package member 20. The outer package member 20 has flexibility or softness. The wound electrode body 10 serves as a battery device. A positive electrode lead 11 and a negative electrode lead 12 are coupled to the wound electrode body 10. In other words, the secondary battery described here is a so-called laminated secondary battery.

Referring to FIG. 1, the outer package member 20 is, for example, a single film that is foldable in a direction of an arrow R. The outer package member 20 has a depression 20U, for example. The depression 20U is adapted to contain the wound electrode body 10. Thus, the outer package member 20 contains the wound electrode body 10, thereby containing, for example, the positive electrode 13, the negative electrode 14, and an electrolytic solution to be described later.

The outer package member 20 may be, for example: a film (a polymer film) including a polymer compound; a thin metal plate (a metal foil); or a stacked body (a laminated film) in which the polymer film and the metal foil are stacked on each other. The polymer film may have a single layer or multiple layers. In a similar manner, the metal foil may have a single layer or multiple layers. The laminated film may have, for example, polymer films and metal foils that are alternately stacked. The number of stacked layers of the polymer films and the number of stacked layers of the metal foils may each be set to any value.

In particular, the outer package member 20 is preferably a laminated film. A reason for this is that a sufficient sealing property is obtainable, and sufficient durability is also obtainable. Specifically, the outer package member 20 is a laminated film including, for example, a fusion-bonding layer, a metal layer, and a surface protective layer that are stacked in this order from an inner side to an outer side. In a process of manufacturing the secondary battery, for example, the outer package member 20 is folded in such a manner that portions of the fusion-bonding layer oppose each other with the wound electrode body 10 interposed therebetween. Thereafter, outer edges of the fusion-bonding layer are fusion-bonded to each other, thereby sealing the outer package member 20. The fusion-bonding layer is, for example, a polymer film including polypropylene. The metal layer is, for example, a metal foil including aluminum. The surface protective layer is, for example, a polymer film including nylon.

The outer package member 20 may include, for example, two laminated films that are adhered to each other by means of a material such as an adhesive.

A sealing film 31, for example, is disposed between the outer package member 20 and the positive electrode lead 11. The sealing film 31 is adapted to prevent entry of outside air into the outer package member 20. The sealing film 31 includes, for example, a polyolefin resin such as polypropylene.

A sealing film 32, for example, is disposed between the outer package member 20 and the negative electrode lead 12. The sealing film 32 has a role similar to that of the sealing film 31 described above. A material included in the sealing film 32 is similar to the material included in the sealing film 31.

As illustrated in FIGS. 1 to 3, the wound electrode body 10 includes the positive electrode 13, the negative electrode 14, and a separator 15, for example. In the wound electrode body 10, the positive electrode 13 and the negative electrode 14 are stacked with the separator 15 interposed therebetween, and the positive electrode 13, the negative electrode 14, and the separator 15 are wound, for example. The wound electrode body 10 is impregnated with an electrolytic solution, for example. The electrolytic solution is a liquid electrolyte. The positive electrode 13, the negative electrode 14, and the separator 15 are each impregnated with the electrolytic solution, for example. A surface of the wound electrode body 10 is protected by means of, for example, an unillustrated protective tape.

In a process of manufacturing the secondary battery, which will be described later, a jig having an elongated shape is used to wind the positive electrode 13, the negative electrode 14, and the separator 15 about a winding axis J, for example. The winding axis J is an axis extending in a Y-axis direction. Accordingly, the wound electrode body 10 is formed into an elongated shape resulting from the shape of the jig, as illustrated in FIG. 1, for example. Thus, as illustrated in FIG. 2, for example, the wound electrode body 10 includes a flat part (a flat part 10F) located in the middle and a pair of curved parts (curved parts 10R) located on both sides of the flat part 10F. That is, the pair of curved parts 10R opposes each other with the flat part 10F interposed therebetween. FIG. 2 includes a dashed line that indicates a border between the flat part 10F and each of the curved parts 10R and shading in the curved parts 10R for easier distinction between the flat part 10F and the curved parts 10R.

As illustrated in FIG. 3, the positive electrode 13 includes, for example, a positive electrode current collector 13A, and a positive electrode active material layer 13B provided on the positive electrode current collector 13A. The positive electrode active material layer 13B may be provided, for example, only on one side of the positive electrode current collector 13A, or on each of both sides of the positive electrode current collector 13A. FIG. 3 illustrates a case where the positive electrode active material layer 13B is provided on each of the both sides of the positive electrode current collector 13A, for example.

The positive electrode current collector 13A includes, for example, an electrically conductive material such as aluminum. The positive electrode active material layer 13B includes, as a positive electrode active material or positive electrode active materials, one or more of positive electrode materials into which lithium ions are insertable and from which lithium ions are extractable. The positive electrode active material layer 13B may further include another material, examples of which include a positive electrode binder and a positive electrode conductor.

The positive electrode material includes a lithium compound. The term "lithium compound" is a generic term for a compound that includes lithium as a constituent element. A reason for this is that a high energy density is achievable. The lithium compound includes a lithium-cobalt composite oxide having a layered rock-salt crystal structure. Hereinafter, the lithium-cobalt composite oxide having the layered rock-salt crystal structure is referred to as a "layered rock-salt lithium-cobalt composite oxide". A reason for this is that a high energy density is stably achievable. The term "layered rock-salt lithium-cobalt composite oxide" is a generic term for a composite oxide that includes lithium and cobalt as constituent elements. Accordingly, the layered rock-salt lithium-cobalt composite oxide may further include one or more of other elements (elements other than lithium and cobalt). The other elements are not limited to particular kinds; however, the other elements may be those belong to groups 2 to 15 in the long periodic table of elements, for example.

Specifically, the layered rock-salt lithium-cobalt composite oxide includes one or more of compounds represented by Formula (1) below. A reason for this is that a sufficient energy density is stably achievable. It should be understood that a composition of lithium differs depending on a charging state and a discharging state. A value of x included in Formula (1) represents a value of a state in which the positive electrode 13 is taken out from the secondary battery, following which the positive electrode 13 is discharged until the potential reaches 3 V (versus a lithium reference electrode).

$$Li_xCo_{1-y}M_yO_{2-z}X_z \quad (1)$$

where:
M is at least one of titanium (Ti), vanadium (V), chromium (Cr), manganese (Mn), iron (Fe), nickel (Ni), copper (Cu), sodium (Na), magnesium (Mg), aluminum (Al), silicon (Si), tin (Sn), potassium (K), calcium (Ca), zinc (Zn), gallium (Ga), strontium (Sr), yttrium (Y), zirconium (Zr), niobium (Nb), molybdenum (Mo), barium (Ba), lanthanum (La), tungsten (W), or boron (B);

X is at least one of fluorine (F), chlorine (Cl), bromine (Br), iodine (I), or sulfur (S); and x, y, and z satisfy $0.8 < x < 1.2$, $0 \leq y < 0.15$, and $0 \leq z < 0.05$.

As is apparent from Formula (1), the layered rock-salt lithium-cobalt composite oxide is a cobalt-based lithium composite oxide. The layered rock-salt lithium-cobalt composite oxide may further include one or more of first additional elements (M), and may further include one or more of second additional elements (X). Details on each of the first additional element (M) and the second additional element (X) are as described above.

In other words, as is apparent from a value range that y can take, the layered rock-salt lithium-cobalt composite oxide may include no first additional element (M). Similarly, as is apparent from a value range that z can take, the layered rock-salt lithium-cobalt composite oxide may include no second additional element (X).

The layered rock-salt lithium-cobalt composite oxide is not limited to a particular kind as long as the layered rock-salt lithium-cobalt composite oxide is a compound represented by Formula (1). Specific examples of the layered rock-salt lithium-cobalt composite oxide include $LiCoO_2$, $LiCo_{0.98}Al_{0.02}O_2$, $LiCo_{0.98}Mn_{0.02}O_2$, and $LiCo_{0.98}Mg_{0.02}O_2$.

It should be understood that the positive electrode material may include, for example, one or more of other lithium compounds together with the lithium compound (the layered rock-salt lithium-cobalt composite oxide) described above. Examples of the other lithium compounds include another lithium composite oxide and a lithium phosphate compound.

The term "other lithium composite oxide" is a generic term for a composite oxide that includes, as constituent elements, lithium and one or more of other elements. The other lithium composite oxide has any of crystal structures including, without limitation, a layered rock-salt crystal structure and a spinel crystal structure, for example. However, a compound corresponding to the layered rock-salt lithium-cobalt composite oxide is excluded from the other lithium composite oxide described here. The term "lithium phosphate compound" is a generic term for a phosphate compound that includes, as constituent elements, lithium and one or more of the other elements. The lithium phosphate compound has a crystal structure such as an olivine crystal structure, for example. Details of the other elements are as described above.

Examples of the other lithium composite oxide having the layered rock-salt crystal structure include $LiNiO_2$. Examples of the other lithium composite oxide having the spinel crystal structure include $LiMn_2O_4$. Examples of the lithium phosphate compound having the olivine crystal structure include $LiFePO_4$, $LiMnPO_4$, and $LiMn_{0.5}Fe_{0.5}PO_4$.

The positive electrode binder includes one or more of materials including, without limitation, a synthetic rubber and a polymer compound, for example. Examples of the synthetic rubber include a styrene-butadiene-based rubber. Examples of the polymer compound include polyvinylidene difluoride and polyimide.

The positive electrode conductor includes, for example, one or more of electrically conductive materials such as a carbon material. Examples of the carbon material include graphite, carbon black, acetylene black, and Ketjen black. The electrically conductive material may include a material such as a metal material or an electrically conductive polymer.

As illustrated in FIG. 3, the negative electrode 14 includes, for example, a negative electrode current collector 14A, and a negative electrode active material layer 14B provided on the negative electrode current collector 14A. The negative electrode active material layer 14B may be provided, for example, only on one side of the negative electrode current collector 14A, or on each of both sides of the negative electrode current collector 14A. FIG. 3 illustrates a case where the negative electrode active material layer 14B is provided on each of the both sides of the negative electrode current collector 14A, for example.

The negative electrode current collector 14A includes, for example, an electrically conductive material such as copper. It is preferable that the negative electrode current collector 14A have a surface roughened by a method such as an electrolysis method. A reason for this is that improved adherence of the negative electrode active material layer 14B to the negative electrode current collector 14A is achievable by utilizing a so-called anchor effect.

The negative electrode active material layer 14B includes, as a negative electrode active material or negative electrode active materials, one or more of negative electrode materials into which lithium ions are insertable and from which lithium ions are extractable. The negative electrode active material layer 14B may further include another material such as a negative electrode binder or a negative electrode conductor.

The negative electrode material includes a carbon material. The term "carbon material" is a generic term for a material mainly including carbon as a constituent element. A reason for this is that a high energy density is stably obtainable owing to the crystal structure of the carbon material which hardly varies upon insertion and extraction of lithium ions. Another reason is that improved electrical conductivity of the negative electrode active material layer 14B is achievable owing to the carbon material which also serves as the negative electrode conductor.

Specifically, the negative electrode material includes graphite. The graphite is not limited to a particular kind. The graphite may be artificial graphite, natural graphite, or both.

In a case where the negative electrode material includes a plurality of pieces of particulate graphite (a plurality of graphite particles), an average particle diameter (a median diameter D50) of the graphite particles is not particularly limited; however, the median diameter D50 is preferably from 3.5 μm to 30 μm both inclusive, and more preferably from 5 μm to 20 μm both inclusive. A reason for this is that precipitation of lithium metal is suppressed and occurrence of a side reaction is also suppressed. In detail, the median diameter D50 of smaller than 3.5 μm makes it easier for the side reaction to occur on surfaces of the graphite particles due to increased surface areas of the graphite particles, which may reduce an initial-cycle charge and discharge efficiency. In contrast, if the median diameter D50 is larger than 30 μm, gaps (vacancies) between graphite particles, which are flowing paths of the electrolytic solution, may be unevenly distributed, which may cause precipitation of lithium metal.

Here, it is preferable that some or all of the plurality of graphite particles form so-called secondary particles. A reason for this is that an orientation of the negative electrode 14 (the negative electrode active material layer 14B) is suppressed, thereby suppressing swelling of the negative electrode active material layer 14B upon charging and discharging. With respect to a weight of the plurality of graphite particles, a ratio of a weight occupied by a plurality of graphite particles forming the secondary particles is not particularly limited; however, the ratio is preferably from 20 wt % to 80 wt % both inclusive. If the ratio of graphite particles forming the secondary particles is relatively large, a total surface area of the particles is excessively increased due to a relatively small average particle diameter of primary particles, which may cause a decomposition reaction of the electrolytic solution to occur and a capacity per unit weight to be decreased.

In a case where graphite is analyzed by X-ray diffractometry (XRD), spacing of a graphene layer, having a graphite crystal structure, determined from a position of a peak derived from a (002) plane, that is, spacing S of the (002) plane, is preferably from 0.3355 nm to 0.3370 nm both inclusive, and more preferably from 0.3356 nm to 0.3363 nm both inclusive. A reason for this is that the decomposition reaction of the electrolytic solution is reduced while securing the battery capacity. In detail, if the spacing S is greater than 0.3370 nm, the battery capacity may be reduced due to inadequate graphitization of graphite. In contrast, if the spacing S is smaller than 0.3355 nm, a reactivity of the graphite to the electrolytic solution increases due to excessive graphitization of the graphite, which may cause the decomposition reaction of the electrolytic solution to occur.

The negative electrode material may include, for example, one or more of other materials together with the carbon material (graphite) described above. Examples of the other materials include another carbon material and a metal-based material. A reason for this is that the energy density further increases.

Examples of the other carbon material include non-graphitizable carbon. A reason for this is that a high energy density is stably achievable. A physical property of the non-graphitizable carbon is not particularly limited; however, in particular, spacing of the (002) plane is preferably greater than or equal to 0.37 nm. A reason for this is that a sufficient energy density is achievable.

The term "metal-based material" is a generic term for a material including, as a constituent element or constituent elements, one or more of: metal elements that are each able to form an alloy with lithium; and metalloid elements that are each able to form an alloy with lithium. The metal-based material may be a simple substance, an alloy, a compound, a mixture of two or more thereof, or a material including one or more phases thereof.

It should be understood that the simple substance described here merely refers to a simple substance in a general sense. The simple substance may therefore include a small amount of impurity, that is, does not necessarily have a purity of 100%. The term "alloy" encompasses, for example, not only a material that includes two or more metal elements but may also encompass a material that includes one or more metal elements and one or more metalloid elements. The alloy may further include one or more non-metallic elements. The metal-based material has a state such as a solid solution, a eutectic (a eutectic mixture), an intermetallic compound, or a state including two or more thereof that coexist, although not particularly limited thereto.

Specific examples of the metal element and the metalloid element include magnesium, boron, aluminum, gallium, indium, silicon, germanium, tin, lead, bismuth, cadmium, silver, zinc, hafnium, zirconium, yttrium, palladium, and platinum.

Among the above-described materials, a material including silicon as a constituent is preferable. Hereinafter, the material including silicon as a constituent is referred to as a "silicon-containing material". A reason for this is that a markedly high energy density is obtainable owing to superior lithium-ion insertion capacity and superior lithium-ion extraction capacity thereof.

The silicon alloy includes, as a constituent element or constituent elements other than silicon, for example, one or more of tin, nickel, copper, iron, cobalt, manganese, zinc, indium, silver, titanium, germanium, bismuth, antimony, and chromium. The silicon compound includes, as a constituent element or constituent elements other than silicon, for example, one or both of carbon and oxygen. The silicon compound may include, as a constituent element or constituent elements other than silicon, one or more of the series of constituent elements described in relation to the silicon alloy, for example.

Specific examples of the silicon-containing material include $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, and a silicon oxide represented by Formula (4) below. In particular, the silicon oxide is preferable. A reason for this is that the silicon oxide has a relatively large capacity per unit weight and a relatively large capacity per unit volume in graphite ratios. Another reason is that, in the silicon oxide which includes oxygen, a structure thereof is stabilized by an oxygen-silicon bond and a lithium-oxygen bond after being lithiated, thereby suppressing cracking of the particles. The silicon oxide is not limited to a particular kind, and examples thereof include SiO.

$$SiO_v \qquad (4)$$

where v satisfies $0.5 \leq v \leq 1.5$.

Details of the negative electrode binder are similar to those of the positive electrode binder, for example. Details of the negative electrode conductor are similar to those of the positive electrode conductor, for example. However, the negative electrode binder may be, for example, a water-based (water-soluble) polymer compound. Examples of the water-soluble polymer compound include carboxymethyl cellulose and a metal salt thereof.

The separator 15 is interposed between the positive electrode 13 and the negative electrode 14, and causes the positive electrode 13 and the negative electrode 14 to be separated away from each other. The separator 15 includes a porous film of a material such as a synthetic resin or ceramic, for example. The separator 15 may be a stacked film including two or more porous films that are stacked on each other, in one example. Examples of the synthetic resin include polyethylene.

The electrolytic solution includes, for example, a solvent and an electrolyte salt. Only one solvent may be used, or two or more solvents may be used. Only one electrolyte salt may be used, or two or more electrolyte salts may be used.

The solvent includes one or more of non-aqueous solvents (organic solvents), for example. An electrolytic solution including the non-aqueous solvent is a so-called non-aqueous electrolytic solution.

The non-aqueous solvent is not limited to a particular kind, and examples thereof include a cyclic carbonate ester, a chain carbonate ester, a lactone, a chain carboxylate ester, and a nitrile (mononitrile) compound. A reason for this is that characteristics including, without limitation, a capacity characteristic, a cyclability characteristic, and a storage characteristic are secured.

Examples of the cyclic carbonate ester include ethylene carbonate and propylene carbonate. Examples of the chain carbonate ester include dimethyl carbonate and diethyl carbonate. Examples of the lactone include γ-butyrolactone and γ-valerolactone. Examples of the chain carboxylate ester include methyl acetate, ethyl acetate, methyl propionate, and propyl propionate. Examples of the nitrile compound include acetonitrile, methoxy acetonitrile, and 3-methoxy propionitrile.

Examples of the non-aqueous solvent further include an unsaturated cyclic carbonate ester, a halogenated carbonate ester, a sulfonate ester, an acid anhydride, a dicyano compound (a dinitrile compound), a diisocyanate compound, and a phosphate ester. A reason for this is that one or more of the above-described characteristics including, without limitation, a capacity characteristic are further improved.

Examples of the unsaturated cyclic carbonate ester include vinylene carbonate, vinyl ethylene carbonate, and methylene ethylene carbonate. The halogenated carbonate ester may be a cyclic halogenated carbonate ester or a chain halogenated carbonate ester. Examples of the halogenated carbonate ester include 4-fluoro-1,3-dioxolane-2-one, 4,5-difluoro-1,3-dioxolane-2-one, and fluoromethyl methyl carbonate. Examples of the sulfonate ester include 1,3-propane sultone and 1,3-propene sultone. Examples of the acid anhydride include succinic anhydride, glutaric anhydride, maleic anhydride, ethane disulfonic anhydride, propane disulfonic anhydride, sulfobenzoic anhydride, sulfopropionic anhydride, and sulfobutyric anhydride. Examples of the dinitrile compound include succinonitrile, glutaronitrile, adiponitrile, and phthalonitrile. Examples of the diisocyanate compound include hexamethylene diisocyanate. Examples of the phosphate ester include trimethyl phosphate and triethyl phosphate.

The electrolyte salt includes one or more of lithium salts, for example. The electrolyte salt may further include one or more of light metal salts other than the lithium salt. The lithium salt is not limited to a particular kind, and examples thereof include lithium hexafluorophosphate ($LiPF_6$), lithium tetrafluoroborate ($LiBF_4$), lithium bis(fluorosulfonyl)imide ($LiN(SO_2F)_2$), lithium bis(trifluoromethane sulfonyl)imide ($LiN(CF_3SO_2)_2$), lithium fluorophosphate ($Li_2PFO_3$), lithium difluorophosphate ($LiPF_2O_2$), and lithium bis(oxalato)borate ($LiC_4BO_8$). A reason for this is that characteristics including, without limitation, a capacity characteristic, a cyclability characteristic, and a storage characteristic are secured.

A content of the electrolyte salt is, for example, greater than or equal to 0.3 mol/kg and less than or equal to 3.0 mol/kg with respect to the solvent, but is not particularly limited thereto.

[Positive Electrode Lead and Negative Electrode Lead]

The positive electrode lead 11 is coupled to the positive electrode 13, and is led out from inside to outside the outer package member 20. The positive electrode lead 11 includes, for example, an electrically conductive material such as aluminum. The positive electrode lead 11 has a shape such as a thin plate shape or a meshed shape, for example.

The negative electrode lead 12 is coupled to the negative electrode 14, and is led out from inside to outside the outer package member 20. A lead-out direction of the negative electrode lead 12 is, for example, similar to a lead-out direction of the positive electrode lead 11. The negative electrode lead 12 includes, for example, an electrically conductive material such as nickel. The negative electrode lead 12 has a shape similar to the shape of the positive electrode lead 11, for example.

Figure 4:
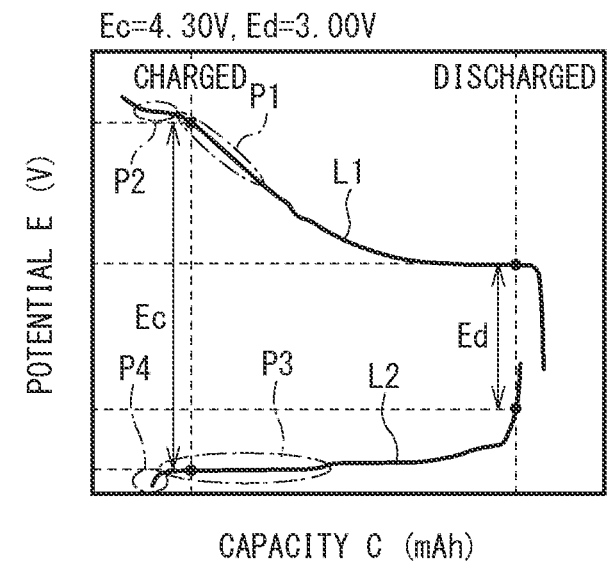
FIG. 4 is a capacity potential curve (charge voltage Ec=4.30 V) of a secondary battery according to a comparative example.
Figure 5:
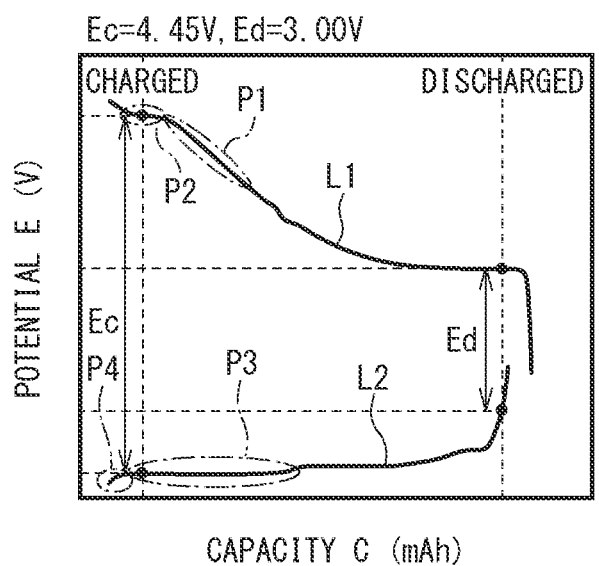
FIG. 5 is another capacity potential curve (charge voltage Ec=4.45 V) of the secondary battery according to the comparative example.
Figure 6:
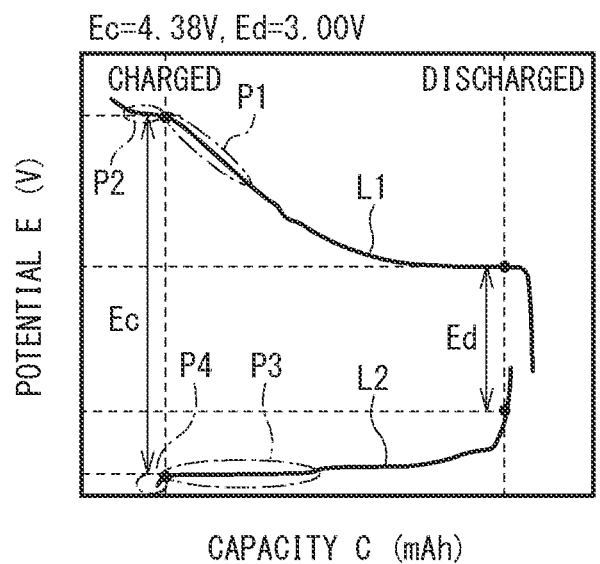
FIG. 6 is a capacity potential curve (charge voltage Ec=4.38 V) of a secondary battery according to an embodiment of the present technology.
Figure 7:
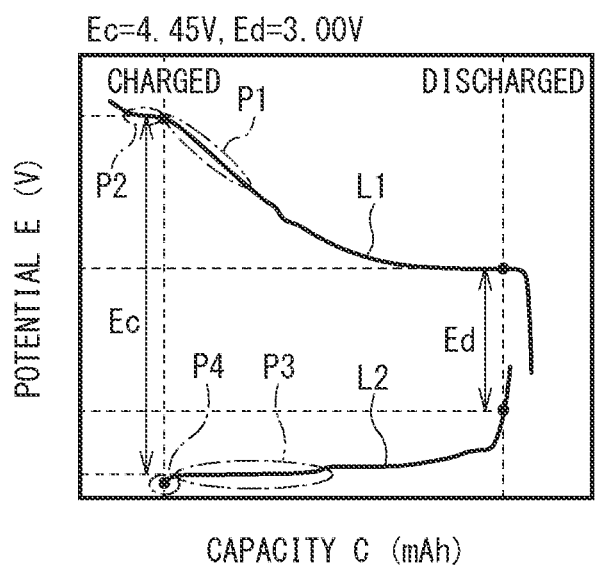
FIG. 7 is another capacity potential curve (charge voltage Ec=4.45 V) of the secondary battery according to an embodiment of the present technology.

A charge and discharge principle and configuration conditions of the secondary battery of the first embodiment will now be described. FIGS. 4 and 5 each represent a capacity potential curve related to a secondary battery according to a comparative example of the secondary battery according to the first embodiment. FIGS. 6 and 7 each represent a capacity potential curve related to the secondary battery according to the first embodiment.

In each of FIGS. 4 to 7, a horizontal axis represents a capacity C (mAh) and a vertical axis represents a potential E (V). The potential E is an open circuit potential to be measured with lithium metal as a reference electrode, i.e., a potential versus a lithium reference electrode. FIGS. 4 to 7 each indicate a charge and discharge curve L1 of the positive electrode 13 and a charge and discharge curve L2 of the negative electrode 14. It should be understood that a position of a dashed line indicated as "charged" represents a full charge state, and a position of a dashed line indicated as "discharged" represents a full discharge state.

A charge voltage Ec (V) and a discharge voltage Ed (V) are, for example, set as follows. In FIG. 4, the charge voltage Ec is set to 4.30 V and the discharge voltage Ed is set to 3.00 V. In FIG. 5, the charge voltage Ec is set to 4.45 V and the discharge voltage Ed is set to 3.00 V. In FIG. 6, the charge voltage Ec is set to 4.38 V and the discharge voltage Ed is set to 3.00 V. In FIG. 7, the charge voltage Ec is set to 4.45 V and the discharge voltage Ed is set to 3.00 V. Upon charging and discharging, the secondary battery is charged until a battery voltage (a closed circuit voltage) reaches the charge voltage Ec and then discharged until the battery voltage reaches the discharge voltage Ed.

In the following, a description is given of a premise for describing the charge and discharge principle and the configuration conditions of the secondary battery according to the first embodiment. Thereafter, the charge and discharge principle and the configuration conditions for achieving the charge and discharge principle are described.

[Premise]

In order to improve an energy density of the secondary battery, it is conceivable to increase the charge voltage Ec (a so-called end-of-charge voltage). Increase in the charge voltage Ec raises a potential E of the positive electrode 13 in an end stage of charging, and by extension at an end of charging, which causes increase in a use range of the potential E, i.e., a potential range to be used in the positive electrode 13 during charging.

In a case where the layered rock-salt lithium-cobalt composite oxide is used as the positive electrode active material, a potential constant region P2 associated with a phase transition (O3/H1-3 transition) generally exists. Increase in the charge voltage Ec also increases the potential E of the positive electrode 13 in the end stage of charging, which causes the potential E of the positive electrode 13 to reach inside the potential constant region P2 described above. Accordingly, a capacity potential curve L1 of the positive electrode 13 has a potential varying region P1 and the potential constant region P2 as indicated in FIGS. 4 to 7. The potential varying region P1 is a region in which the potential E varies as the capacity C varies. The potential constant region P2 is a region in the capacity potential curve located to the left of the potential varying region P1 and is a region in which the potential E hardly varies even if the capacity C varies as a result of the phase transition.

If the secondary battery including the layered rock-salt lithium-cobalt composite oxide is charged and discharged in such a manner that the potential E of the positive electrode 13 reaches inside the potential constant region P2 associated with the phase transition, or the potential E of the positive electrode 13 passes through the potential constant region P2 associated with the phase transition, a capacity loss relatively easily occurs and gas generation also relatively easily occurs. Such tendencies are relatively strong when the secondary battery is used and stored in a high temperature environment. In particular, if the charge voltage Ec is 4.38 V or higher, the potential E of the positive electrode 13 becomes easier to reach the potential constant region P2 associated with the phase transition, or the potential E of the positive electrode 13 becomes easier to pass through the potential constant region P2 associated with the phase transition.

In contrast, if the charge voltage Ec is increased in a case where graphite is used as the negative electrode active material, a two-phase coexistence reaction of an intercalation compound stage 1 and an interlayer compound stage 2 proceeds in the graphite. As a result, a capacity potential curve L2 of the negative electrode 14 has a potential constant region P3 as indicated in FIGS. 4 to 7. The potential constant region P3 is a region in which the potential E hardly varies even if the capacity C varies in association with the two-phase coexistence reaction. A potential E of the negative electrode 14 in the potential constant region P3 is about 90 mV to about 100 mV.

It should be understood that if the charge voltage Ec is further increased, the potential E of the negative electrode 14 exceeds the potential constant region P3, and thus the potential E varies markedly. In association with the increase in the charge voltage Ec that causes the potential E to exceed the potential constant region P3, the capacity potential curve L2 of the negative electrode 14 has a potential varying region P4, as indicated in FIGS. 4 to 7. In FIGS. 4 to 7, the potential varying region P4 is a region located on a lower potential side compared with the potential constant region P3 in the capacity potential curve, and is a region in which the potential E markedly varies (decreases) if the capacity C varies. The potential E of the negative electrode 14 in the potential varying region P4 is lower than about 90 m V.

In the secondary battery according to the first embodiment in which the positive electrode 13 includes the positive electrode active material (the layered rock-salt lithium-cobalt composite oxide) and the negative electrode 14 includes the negative electrode active material (graphite), charging and discharging are performed as described below on the basis of the premise described above. In the following, the charge and discharge principle of the secondary battery according to the first embodiment (FIGS. 6 and 7) will be described, compared with the charge and discharge principle of the secondary battery according to the comparative example (FIGS. 4 and 5).

In the secondary battery according to the comparative example, as indicated in FIG. 4, the potential E of the negative electrode 14 at the end of charging (charge voltage Ec=4.30 V) is set to cause the charging to be completed in the potential constant region P3, in order to prevent a battery capacity from decreasing due to precipitation of lithium metal on the negative electrode 14.

However, in a case where the charge voltage Ec of the secondary battery according to the comparative example is increased to 4.38 V or higher, more specifically, to 4.45 V, the potential E of the positive electrode 13 reaches 4.50 V or higher as indicated in FIG. 5 in association with the increase in the potential E of the negative electrode 14 at the end of charging. As a result, the potential E of the positive electrode 13 at the end of charging (charge voltage Ec=4.45 V) reaches the potential constant region P2 associated with the phase transition or passes through the potential constant region P2 associated with the phase transition.

Thus, in the secondary battery according to the comparative example, the increase in the charge voltage Ec to 4.38 V or higher makes it easier for the potential E of the positive electrode 13 to reach the potential constant region P2 associated with the phase transition, or for the potential E of the positive electrode 13 to pass through the potential constant region P2 associated with the phase transition. As a result, the capacity loss relatively easily occurs, and the gas generation also relatively easily occurs, making it easier to deteriorate battery characteristics. As described above, the tendency that the battery characteristics easily deteriorate becomes relatively strong when the secondary battery is used and stored in a high temperature environment.

Moreover, in the secondary battery according to the comparative example, the battery capacity is easily influenced by, for example, an active material ratio (a ratio between an amount of the positive electrode active material and an amount of the negative electrode active material) and the charge voltage Ec. Thus, the battery capacity easily varies in association with, for example, variation in the active material ratio (amount) and a setting error of the charge voltage Ec by a charging device. Accordingly, the variation in the capacity C of the positive electrode 13 makes it easier for the potential E of the positive electrode 13 to reach the potential constant region P2 associated with the phase transition, or the potential E of the positive electrode 13 to pass through the potential constant region P2 associated with phase transition. As a result, the battery capacity easily varies, and an operable time of, for example, an apparatus or a device that operates using the secondary battery as a power source is shortened due to decrease in the battery capacity. In addition, if the battery capacity varies, lithium metal is generated on the negative electrode 14 more easily.

In contrast, in the secondary battery according to the first embodiment, the potential E of the negative electrode 14 is set to help to prevent the potential E of the positive electrode 13 (the layered rock-salt lithium-cobalt composite oxide) from reaching the potential constant region P2 associated with the phase transition or the potential E of the positive electrode 13 from passing through the potential constant region P2 associated with the phase transition, and also to suppress the precipitation of lithium metal on the negative electrode 14. Specifically, as indicated in FIG. 6, the potential E of the negative electrode 14 at the end of charging (charge voltage Ec=4.38 V) is set to cause the charging not to be completed in the potential constant region P3 and to be completed in the potential varying region P4. Further, as indicated in FIG. 7, the potential E of the negative electrode 14 at the end of charging (charge voltage Ec=4.45 V) is similarly set to cause the charging not to be completed in the potential constant region P3 and to be completed in the potential varying region P4.

In this case, because the potential E of the negative electrode 14 at the end of charging decreases, the potential E of the positive electrode 13 at the end of charging also decreases. Specifically, in the secondary battery according to the first embodiment, the potential E of the positive electrode 13 does not reach 4.50 V or above even if the charge voltage Ec is increased to 4.38 V or higher, more specifically to 4.45 V, as indicated in FIGS. 6 and 7, in association with the decrease in the potential E of the negative electrode 14 at the end of charging. Thus, the potential E of the positive electrode 13 at the end of charging (charge voltage Ec=4.38 V or 4.45 V) is set not to reach the potential constant region P2 associated with the phase transition, or not to pass through the potential constant region P2 associated with the phase transition.

Upon charging, as is apparent from FIGS. 6 and 7, when the secondary battery is charged up to the charge voltage Ec of 4.38 V or higher, the potential E of the negative electrode 14 markedly decreases in the potential varying region P4, and thus a charging reaction is completed. Thus, the potential E of the positive electrode 13 is controlled at the end stage of charging as described above, which prevents the potential E of the positive electrode 13 from easily reaching the potential constant region P2 associated with the phase transition, or prevents the potential E of the positive electrode 13 from easily passing through the potential constant region P2 associated with the phase transition. In addition, if the potential E of the negative electrode 14 markedly decreases in the potential varying region P4, the charging reaction is immediately terminated. This prevents the charging reaction from proceeding to an extent where the precipitation of lithium metal occurs on the negative electrode 14.

Accordingly, in the secondary battery according to the first embodiment, even if the charge voltage Ec is increased to 4.38 V or higher, the potential E of the positive electrode 13 is prevented from easily reaching the potential constant region P2 associated with the phase transition, or the potential E of the positive electrode 13 is prevented from easily passing through the potential constant region P2 associated with the phase transition. As a result, the capacity loss is relatively suppressed, and the gas generation is also relatively suppressed. In addition, even if the charge voltage Ec is increased to 4.38 V or higher, the precipitation of lithium metal is suppressed on the negative electrode 14, which suppresses decrease in the battery capacity.

Moreover, in the secondary battery according to the first embodiment, the battery capacity is less influenced by, for example, an active material ratio and the charge voltage Ec. This helps to suppress variation in the battery capacity, and secures the operable time of, for example, an apparatus or a device that operates using the secondary battery as a power source. In addition, even if the battery capacity varies, generation of lithium metal is suppressed on the negative electrode 14.

In the secondary battery according to the first embodiment, two configuration conditions described below are satisfied in order to achieve the charge and discharge principle described above.

First, a state in which the secondary battery is charged with a constant voltage of a closed circuit voltage (CCV) of 4.38 V or higher for 24 hours is referred to as a full charge state. A potential E (a negative electrode potential Ef) of the negative electrode 14 measured in the secondary battery in the full charge state is from 19 mV to 86 mV both inclusive. It should be understood that a value of a current at the time of charging the secondary battery until the closed circuit voltage reaches 4.38 V or higher is not particularly limited, and may thus be set to any value.

That is, as described above, the potential E of the negative electrode 14 is set to cause the charging not to be completed in the potential constant region P3 and to be completed in the potential varying region P4. Accordingly, when the secondary battery is charged to the full charge state, the negative electrode potential Ef is lower in a case where the charging is completed in the potential varying region P4 than in a case where the charging is completed in the potential constant region P3. Thus, the negative electrode potential Ef becomes lower than about 90 mV, and more specifically, from 19 mV to 86 mV both inclusive, as described above.

Secondly, a discharge capacity obtained when the secondary battery is discharged with a constant current from the full charge state until a closed circuit voltage reaches 3.00 V, following which the secondary battery is discharged with a constant voltage of the closed circuit voltage of 3.00 V for 24 hours is referred to as a maximum discharge capacity (mAh). In this case, when the secondary battery is discharged from the full charge state by a capacity corresponding to 1% of the maximum discharge capacity, a variation of the potential E of the negative electrode 14, i.e., a negative electrode potential variation Ev, represented by Formula (2) below is 1 mV or greater. As is apparent from Formula (2), the negative electrode potential variation Ev is a difference between a potential E1 (a first negative electrode potential) and a potential E2 (a second negative electrode potential). It should be understood that the current value at the time of discharging the secondary battery from the full charge state until the closed circuit voltage reaches 3.00 V is not particularly limited and may be set to any value as long as the current value is within a general range, because the secondary battery is discharged with a constant voltage for 24 hours.

$$\text{Negative electrode potential variation } Ev \text{ (mV)} = \text{potential } E2 \text{ (mV)} - \text{potential } E1 \text{ (mV)} \tag{2}$$

where:
the potential E1 is an open circuit potential (versus a lithium reference electrode) of the negative electrode 14 measured in the secondary battery in the full charge state; and
the potential E2 is an open circuit potential (versus a lithium reference electrode) of the negative electrode 14 measured in the secondary battery in a state in which the secondary battery is discharged from the full charge state by the capacity corresponding to 1% of the maximum discharge capacity.

That is, as described above, in a case where the potential E of the negative electrode 14 is set to cause the charging to be completed in the potential varying region P4, the potential E of the negative electrode 14 increases markedly upon discharging the secondary battery in the full charge state by the capacity corresponding to 1% of the maximum discharge capacity, as is apparent from FIGS. 6 and 7. Thus, the potential E (E2) of the negative electrode 14 after the discharging is sufficiently increased as compared with the potential E (E1) of the negative electrode 14 before the discharging (the full charge state). Accordingly, the negative electrode potential variation Ev, which is the difference between the potential E1 and the potential E2, is 1 mV or greater as described above.

In a case where the two configuration conditions (the negative electrode potential Ef and the negative electrode potential variation Ev) are satisfied, it is more preferable that a variation of the potential E of the positive electrode 13 (a positive electrode potential variation Ew) represented by Formula (3) below be 2 mV or greater when the secondary battery is discharged from the full charge state by the capacity corresponding to 1% of the maximum discharge capacity. A reason for this is that, in end stage of charging, the potential E of the positive electrode 13 is prevented from easily reaching the potential constant region P2 associated with the phase transition, or the potential E of the positive electrode 13 is prevented from easily passing through the potential constant region P2 associated with the phase transition.

$$\text{Positive electrode potential variation } Ew \text{ (mV)} = \text{first positive electrode potential (mV)} - \text{second positive electrode potential (mV)} \tag{3}$$

where:
the first positive electrode potential is an open circuit potential (versus a lithium reference electrode) of the positive electrode 13 measured in the secondary battery in the full charge state; and
the second positive electrode potential is an open circuit potential (versus a lithium reference electrode) of the positive electrode 13 measured in the secondary battery that is discharged from the full charge state by the capacity corresponding to 1% of the maximum discharge capacity.

That is, as described above, in the secondary battery according to the first embodiment in which the potential E of the positive electrode 13 is set not to reach the potential constant region P2 associated with the phase transition, or not to pass through the potential constant region P2 associated with the phase transition, the potential E of the positive electrode 13 is sufficiently reduced upon discharging the secondary battery in the full charge state by the capacity corresponding to 1% of the maximum discharge capacity, as is apparent from FIGS. 6 and 7. Thus, the potential E (E2) of the positive electrode 13 after the discharging is sufficiently reduced as compared with the potential E (E1) of the positive electrode 13 before the discharging (the full charge state). Accordingly, the positive electrode potential variation Ew, which is the difference between the potential E1 and the potential E2, is 2 mV or greater as described above.

In contrast, as described above, in the secondary battery according to the comparative example in which the potential E of the positive electrode 13 is set to reach the potential constant region P2 associated with the phase transition, or to pass through the potential constant region P2 associated with the phase transition, the positive electrode 13 hardly varies upon discharging the secondary battery in the full charge state by the capacity corresponding to 1% of the maximum discharge capacity, as is apparent from FIGS. 4 and 5. Thus, the potential E (E2) of the positive electrode 13 after the discharging is substantially the same as the potential E (E1) of the positive electrode 13 before the discharging (the full charge state). Accordingly, the positive electrode potential variation Ew, which is the difference between the potential E1 and the potential E2, is less than 2 mV.

The secondary battery according to the first embodiment operates as follows, for example. Upon charging the secondary battery, lithium ions are extracted from the positive electrode 13, and the extracted lithium ions are inserted into the negative electrode 14 via the electrolytic solution. Upon discharging the secondary battery, lithium ions are extracted from the negative electrode 14, and the extracted lithium ions are inserted into the positive electrode 13 via the electrolytic solution.

In a case of manufacturing the secondary battery according to the first embodiment, the positive electrode 13 and the negative electrode 14 are fabricated and thereafter the secondary battery is assembled using the positive electrode 13 and the negative electrode 14, for example, as described below.

First, the positive electrode active material including the layered rock-salt lithium-cobalt composite oxide is mixed with materials including, without limitation, the positive electrode binder and the positive electrode conductor on an as-needed basis to thereby obtain a positive electrode mixture. Thereafter, the positive electrode mixture is dispersed or dissolved into a solvent such as an organic solvent to thereby prepare a paste positive electrode mixture slurry. Lastly, the positive electrode mixture slurry is applied on both sides of the positive electrode current collector 13A, following which the applied positive electrode mixture slurry is dried to thereby form the positive electrode active material layers 13B. Thereafter, the positive electrode active material layers 13B may be compression-molded by means of a machine such as a roll pressing machine. In this case, the positive electrode active material layers 13B may be heated. The positive electrode active material layers 13B may be compression-molded a plurality of times.

The negative electrode active material layers 14B are provided on both sides of the negative electrode current collector 14A by a procedure similar to the fabrication procedure of the positive electrode 13 described above. Specifically, the negative electrode active material including graphite is mixed with materials including, without limitation, the negative electrode binder and the negative electrode conductor on an as-needed basis to thereby obtain a negative electrode mixture. Thereafter, the negative electrode mixture is dispersed or dissolved into a solvent such as an organic solvent or an aqueous solvent to thereby prepare a paste negative electrode mixture slurry. Thereafter, the negative electrode mixture slurry is applied on both sides of the negative electrode current collector 14A, following which the applied negative electrode mixture slurry is dried to thereby form the negative electrode active material layers 14B. Thereafter, the negative electrode active material layers 14B may be compression-molded.

In the case of fabricating the positive electrode 13 and the negative electrode 14, a mixture ratio between the positive electrode active material and the negative electrode active material (a relationship between mass of the positive electrode active material and mass of the negative electrode active material) is adjusted in such a manner that the mass of the positive electrode active material is sufficiently greater, to thereby satisfy the above-described configuration conditions (the negative electrode potential Ef, the negative electrode potential variation Ev, and the positive electrode potential variation Ew).

First, the positive electrode lead 11 is coupled to the positive electrode 13 (the positive electrode current collector 13A) by a method such as a welding method, and the negative electrode lead 12 is coupled to the negative electrode 14 (the negative electrode current collector 14A) by a method such as a welding method. Thereafter, the positive electrode 13 and the negative electrode 14 are stacked on each other with the separator 15 interposed therebetween, following which the positive electrode 13, the negative electrode 14, and the separator 15 are wound to thereby form a wound body. In this case, an unillustrated jig having an elongated shape is used to wind the positive electrode 13, the negative electrode 14, and the separator 15 about the winding axis J to thereby cause the wound body to be in the elongated shape as illustrated in FIG. 1.

Thereafter, the outer package member 20 is folded in such a manner as to sandwich the wound electrode body 10, following which the outer edges excluding one side of the outer package member 20 are bonded to each other by a method such as a thermal fusion bonding method. Thus, the wound body is contained in the pouch-shaped outer package member 20. Lastly, the electrolytic solution is injected into the pouch-shaped outer package member 20, following which the outer package member 20 is sealed by a method such as a thermal fusion bonding method. In this case, the sealing film 31 is disposed between the outer package member 20 and the positive electrode lead 11, and the sealing film 32 is disposed between the outer package member 20 and the negative electrode lead 12. The wound body is thereby impregnated with the electrolytic solution, forming the wound electrode body 10. Thus, the wound electrode body 10 is contained in the outer package member 20. As a result, the secondary battery is completed.

According to the secondary battery of the first embodiment, in a case where the positive electrode 13 includes the positive electrode active material (the layered rock-salt lithium-cobalt composite oxide) and where the negative electrode 14 includes the negative electrode active material (graphite), the above-described two configuration conditions (the negative electrode potential Ef and the negative electrode potential variation Ev) are satisfied. In this case, as compared with the case where the two configuration conditions are not satisfied, even if the charge voltage Ec is increased to 4.38 V or higher: the potential E of the positive electrode 13 is prevented from easily reaching the potential constant region P2 associated with the phase transition, or the potential E of the positive electrode 13 is prevented from easily passing through the potential constant region P2 associated with the phase transition; and precipitation of lithium metal is suppressed on the negative electrode 14. As a result, not only the capacity loss and the gas generation are suppressed, but the decrease in battery capacity is also suppressed. Accordingly, it is possible to achieve superior battery characteristics.

In particular, the configuration condition related to the positive electrode potential variation Ew may also be satisfied. This prevents the potential E of the positive electrode 13 from easily reaching the potential constant region P2 associated with the phase transition, or prevents the potential E of the positive electrode 13 from easily passing through the potential constant region P2 associated with the phase transition, in the positive electrode 13 (the layered rock-salt lithium-cobalt composite oxide) of the end stage of charging. This makes it possible to achieve higher effects accordingly.

Further, the median diameter D50 of the graphite particles may be from 3.5 μm to 30 μm both inclusive. This suppresses the precipitation of lithium metal and also suppresses the occurrence of the side reaction, making it possible to achieve higher effects accordingly.

Moreover, the spacing S of the (002) plane of graphite may be from 0.3355 nm to 0.3370 nm both inclusive. This reduces the decomposition reaction of the electrolytic solution while securing the battery capacity, which makes it possible to achieve higher effects accordingly.

A description is given next of a secondary battery according to a second embodiment of the technology. The secondary battery according to the second embodiment has a configuration that is substantially similar to the configuration of the secondary battery according to the first embodiment described above, except for the points described below.

A positive electrode binder in the secondary battery according to the second embodiment includes one or more of a homopolymer and copolymers each including vinylidene fluoride as a polymerization unit. Hereinafter, the homopolymer and the copolymers each including vinylidene fluoride are each referred to as a "vinylidene fluoride-based polymer compound". A reason for this is that such a vinylidene fluoride-based polymer compound has superior physical strength and is electrochemically stable. Another reason is that, as will be described later, it becomes easier for the positive electrode binder to be swollen with the electrolytic solution.

The homopolymer including vinylidene fluoride as a polymerization unit is polyvinylidene difluoride. The copolymer including vinylidene fluoride as a polymerization unit is not limited to a particular kind, and examples thereof include: a copolymer of vinylidene fluoride and tetrafluoroethylene; a copolymer of vinylidene fluoride and hexafluoropropylene; and a copolymer of vinylidene fluoride, tetrafluoroethylene, and hexafluoropropylene. A reason for this is that it becomes easier for the positive electrode binder to be sufficiently swollen with the electrolytic solution.

In a case where the copolymer includes tetrafluoroethylene as a polymerization unit, a copolymerization amount of tetrafluoroethylene is not particularly limited, and is, for example, 0.1 wt % to 20 wt % both inclusive. In a case where the copolymer includes hexafluoropropylene as a polymerization unit, a copolymerization amount of hexafluoropropylene is not particularly limited, and is, for example, from 0.2 wt % to 5 wt % both inclusive. A reason for this is that it becomes easier for the positive electrode binder to be swollen with the electrolytic solution.

It should be understood that the positive electrode binder may further include one or more of other materials. Examples of the other materials include a synthetic rubber and a polymer compound. However, the vinylidene fluoride-based polymer compound described above is excluded from the polymer compound to be described here. Examples of the synthetic rubber include a styrene-butadiene-based rubber. Examples of the polymer compound include polyimide.

A solvent included in the secondary battery according to the second embodiment includes: a cyclic carbonate ester; and a chain carbonate ester, a chain carboxylate ester, or both. That is, the solvent may include the cyclic carbonate ester and the chain carbonate ester, may include the cyclic carbonate ester and the chain carboxylate ester, or may include the cyclic carbonate ester, the chain carbonate ester, and the chain carboxylate ester. The chain carboxylate ester may have a chain structure or a branched structure having one or more side chains.

The cyclic carbonate ester is not limited to a particular kind, and examples thereof include one or more of ethylene carbonate and propylene carbonate. The chain carbonate ester is not limited to a particular kind, and examples thereof include one or more of dimethyl carbonate and diethyl carbonate. The chain carboxylate ester is not limited to a particular kind, and examples thereof include one or more of an acetate ester, a propionate ester, and a butyrate ester. Specific examples of the chain carboxylate ester include methyl acetate, ethyl acetate, propyl acetate, butyl acetate, methyl propionate, ethyl propionate, propyl propionate, methyl butyrate, 2-methyl ethyl propionate, 2-methyl methyl propionate, and 2,2-dimethyl propionate. In particular, methyl propionate, ethyl propionate, and propyl propionate are preferable.

A reason that the solvent has the above-described composition is that softness of the positive electrode 13 is increased while securing ion conductivity of lithium ions, thereby suppressing cracking of the positive electrode 13 (the positive electrode active material layer 13B) upon charging and discharging, while achieving a higher energy density.

In detail, the cyclic carbonate ester has a high polarity, thereby having a property of easily swelling the positive electrode binder. This increases the softness of the positive electrode active material layer 13B owing to the swelling of the positive electrode binder, thereby preventing the positive electrode active material layer 13B from cracking easily upon charging and discharging. In addition, each of the chain carbonate ester and the chain carboxylate ester has a low polarity, thereby making lithium ions to be moved easily upon charging and discharging even if an area density and a volume density of the positive electrode active material layer 13B are each increased, as will be described later. As a result, a high energy density is achievable while charging and discharging reactions proceed smoothly and stably.

The solvent may also include one or more of other solvents, together with the cyclic carbonate ester, the chain carbonate ester, and the chain carboxylate ester described above.

The other solvent includes one or more of materials including, without limitation, non-aqueous solvents (organic solvents), and an electrolytic solution including the non-aqueous solvent is a so-called non-aqueous electrolytic solution. The non-aqueous solvent is not limited to a particular kind, and examples thereof include a lactone and a nitrile (mononitrile) compound. A reason for this is that characteristics including, without limitation, a battery capacity, a cyclability characteristic, and a storage characteristic are secured. Examples of the lactone include γ-butyrolactone and γ-valerolactone. Examples of the nitrile compound include acetonitrile, methoxy acetonitrile, and 3-methoxy propionitrile.

Examples of the other solvent include an unsaturated cyclic carbonate ester, a halogenated carbonate ester, a sulfonate ester, an acid anhydride, a dicyano compound (a dinitrile compound), a diisocyanate compound, and a phosphate ester. A reason for this is that one or more of the above-described characteristics including, without limitation, a capacity characteristic are further improved.

Examples of the unsaturated cyclic carbonate ester include vinylene carbonate, vinyl ethylene carbonate, and methylene ethylene carbonate. The halogenated carbonate ester may be a cyclic halogenated carbonate ester or a chain halogenated carbonate ester. Examples of the halogenated carbonate ester include 4-fluoro-1,3-dioxolane-2-one, 4,5-difluoro-1,3-dioxolane-2-one, and fluoromethyl methyl carbonate. Examples of the sulfonate ester include 1,3-propane sultone and 1,3-propene sultone. Examples of the acid anhydride include succinic anhydride, glutaric anhydride, maleic anhydride, ethane disulfonic anhydride, propane disulfonic anhydride, sulfobenzoic anhydride, sulfopropionic anhydride, and sulfobutyric anhydride. Examples of the dinitrile compound include succinonitrile, glutaronitrile, adiponitrile, and phthalonitrile. Examples of the diisocyanate compound include hexamethylene diisocyanate. Examples of the phosphate ester include trimethyl phosphate and triethyl phosphate.

The electrolyte salt includes one or more of lithium salts, for example. The electrolyte salt may further include one or more of light metal salts other than the lithium salt. The lithium salt is not limited to a particular kind, and examples thereof include lithium hexafluorophosphate ($LiPF_6$), lithium tetrafluoroborate ($LiBF_4$), lithium bis(fluorosulfonyl)imide ($LiN(SO_2F)_2$), lithium bis(trifluoromethane sulfonyl)imide ($LiN(CF_3SO_2)_2$), lithium fluorophosphate ($Li_2PFO_3$), lithium difluorophosphate ($LiPF_2O_2$), and lithium bis(oxalato)borate ($LiC_4BO_8$). A reason for this is that characteristics including, without limitation, a capacity characteristic, a cyclability characteristic, and a storage characteristic are secured.

A charge and discharge principle and configuration conditions of the secondary battery of the second embodiment will now be described.

The premise and the charge and discharge principle related to the secondary battery according to the second embodiment are similar to the premise and the charge and discharge principle related to the secondary battery according to the first embodiment described above.

In the secondary battery according to the second embodiment, seven configuration conditions described below are satisfied in order to achieve the charge and discharge principle described above.

First, a state in which the secondary battery is charged with a constant voltage of a closed circuit voltage (CCV) of 4.38 V or higher for 24 hours is referred to as a full charge state. A potential E (a negative electrode potential Ef) of the negative electrode 14 measured in the secondary battery in the full charge state is from 19 mV to 86 mV both inclusive. It should be understood that a value of a current at the time of charging the secondary battery until the closed circuit voltage reaches 4.38 V or higher is not particularly limited, and may thus be set to any value.

That is, as described above, the potential E of the negative electrode 14 is set to cause the charging not to be completed in the potential constant region P3 and to be completed in the potential varying region P4. Accordingly, when the secondary battery is charged to the full charge state, the negative electrode potential Ef is lower in a case where the charging is completed in the potential varying region P4 than in a case where the charging is completed in the potential constant region P3. Thus, the negative electrode potential Ef becomes lower than about 90 mV, and more specifically, from 19 mV to 86 mV both inclusive, as described above.

Second, a discharge capacity obtained when the secondary battery is discharged with a constant current from the full charge state until a closed circuit voltage reaches 3.00 V, following which the secondary battery is discharged with a constant voltage of the closed circuit voltage of 3.00 V for 24 hours is referred to as a maximum discharge capacity (mAh). In this case, when the secondary battery is discharged from the full charge state by a capacity corresponding to 1% of the maximum discharge capacity, a variation of the potential E of the negative electrode 14, i.e., a negative electrode potential variation Ev, represented by Formula (5) below is 1 mV or higher. As is apparent from Formula (5), the negative electrode potential variation Ev is a difference between a potential E1 (a first negative electrode potential) and a potential E2 (a second negative electrode potential). It should be understood that the current value at the time of discharging the secondary battery from the full charge state until the closed circuit voltage reaches 3.00 V is not particularly limited and may be set to any value as long as the current value is within a general range, because the secondary battery is discharged with a constant voltage for 24 hours.

$$\text{Negative electrode potential variation } Ev \text{ (mV)} = \text{potential } E2 \text{ (mV)} - \text{potential } E1 \text{ (mV)} \quad (5)$$

where:
the potential E1 is an open circuit potential (versus a lithium reference electrode) of the negative electrode 14 measured in the secondary battery in the full charge state; and
the potential E2 is an open circuit potential (versus a lithium reference electrode) of the negative electrode 14 measured in the secondary battery that is discharged from the full charge state by the capacity corresponding to 1% of the maximum discharge capacity.

That is, as described above, in a case where the potential E of the negative electrode 14 is set to cause the charging to be completed in the potential varying region P4, the potential E of the negative electrode 14 increases markedly upon discharging the secondary battery in the full charge state by the capacity corresponding to 1% of the maximum discharge capacity, as is apparent from FIGS. 6 and 7. Thus, the potential E (E2) of the negative electrode 14 after the discharging is sufficiently increased as compared with the potential E (E1) of the negative electrode 14 before the discharging (the full charge state). Accordingly, the negative electrode potential variation Ev, which is the difference between the potential E1 and the potential E2, is 1 mV or higher as described above.

Whether the above two configuration conditions (the negative electrode potential Ef and the negative electrode potential variation Ev) are satisfied is determined in accordance with a ratio between the mass of the positive electrode active material and the mass of the negative electrode active material. Specifically, in a case where the two configuration conditions are satisfied, the mass of the positive electrode active material is relatively large compared with a case where the two configuration conditions are not satisfied. This results in a relatively increased thickness (amount) of the positive electrode active material layer 13B in the former case compared with the latter case.

Third, the area density of the positive electrode active material layer 13B is greater than or equal to 36 mg/cm². Fourth, the volume density of the positive electrode active material layer 13B is greater than or equal to 3.9 g/cm³. Fifth, a content of the electrolyte salt in the electrolytic solution is from 0.7 mol/kg to 1.5 mol/kg both inclusive with respect to the solvent. A reason for these is the energy density increases.

However, the volume density described here is a bulk density of the positive electrode active material layer 13B excluding the electrolytic solution. In detail, in the completed secondary battery, because the wound electrode body 10 is impregnated with the electrolytic solution as described above, the positive electrode 13 (the positive electrode active material layer 13B) is impregnated with the electrolytic solution. Accordingly, in a case where the volume density is to be measured, the bulk density is measured after the electrolytic solution is sufficiently removed (volatilized) in order to prevent a weight of the electrolytic solution with which the positive electrode active material layer 13B is impregnated from being added.

Sixth, a rate (a content rate) of a weight of the positive electrode binder to a weight of the positive electrode active material layer 13B is from 0.8 wt % to 2.5 wt % both inclusive. The content rate is calculated on the basis of a calculation formula: content rate=(weight of positive electrode binder/weight of positive electrode active material layer)×100. A reason for this is that a content of the positive electrode binder in the positive electrode active material layer 13B is optimized, which makes it easier for the positive electrode binder to be swollen with the electrolytic solution (the cyclic carbonate ester serving as the solvent). This improves softness of the positive electrode active material layer 13B, preventing the positive electrode active material layer 13B from cracking easily upon charging and discharging. In particular, in the case where the two configuration conditions (the negative electrode potential Ef and the negative electrode potential variation Ev) described above are satisfied, the positive electrode active material layer 13B is sufficiently prevented from cracking easily even if the charge voltage Ec is increased to 4.38 V or higher.

Seventh, a ratio (a solvent ratio) of a weight of the cyclic carbonate ester to a sum of a weight of the chain carbonate ester and a weight of the chain carboxylate ester is from 0.2 to 1 both inclusive. This solvent ratio is calculated on the basis of a calculation formula: solvent ratio=weight of cyclic carbonate ester/(weight of chain carbonate ester+weight of chain carboxylate ester).

As described above, when the potential E of the negative electrode 14 decreases at the end of charging, a capacity range actually used becomes sufficiently large with respect to a theoretical capacity of the negative electrode 14. For this reason, increase in the energy density causes the positive electrode active material layer 13B to crack more easily due to swelling of the secondary battery, and precipitation of lithium metal tends to occur on the negative electrode 14, at the end of charging. In particular, in the case where the two configuration conditions (the negative electrode potential Ef and the negative electrode potential variation Ev) described above are satisfied, the thickness of the positive electrode active material layer 13B is relatively increased as described above, which causes the positive electrode active material layer 13B to crack further more easily. The tendency of the positive electrode active material layer 13B to crack in this manner becomes stronger in the curved part 10R where a large internal stress (distortion) occurs easily due to bending of the positive electrode 13 in a process of forming the wound electrode body 10. If the positive electrode active material layer 13B cracks, it becomes difficult for the charging and discharging reactions to proceed stably, and makes it easier for the electrolytic solution to be decomposed upon charging and discharging. Accordingly, battery characteristics are deteriorated.

However, even if the two configuration conditions (the negative electrode potential Ef and the negative electrode potential variation Ev) described above are satisfied, a mixture ratio of the cyclic carbonate ester to the chain carbonate ester and the chain carboxylate ester is optimized if the above-described configuration condition related to the solvent ratio is satisfied. This makes it easier for the positive electrode binder to be swollen with the electrolytic solution (the cyclic carbonate ester serving as the solvent), and also makes it easier for the lithium ions to move. Accordingly, even if the charge voltage Ec is increased to 4.38 V or higher, softness of the positive electrode 13 is increased, thereby preventing the positive electrode active material layer 13B from cracking easily, and mobility of lithium ions is ensured, thereby suppressing the precipitation of lithium metal on the negative electrode 14.

In a case of examining whether the above-described seven configuration conditions are satisfied using the completed secondary battery, the secondary battery is disassembled to thereby collect the positive electrode active material layer 13B, the positive electrode binder, and the electrolytic solution. The collected positive electrode active material layer 13B is used to thereby measure the area density and the volume density. The collected positive electrode active material layer 13B and the collected positive electrode binder are used to calculate the content rate. The collected electrolytic solution is analyzed to examine the solvent ratio and the content of the electrolyte salt.

It should be understood that, in a case of confirming whether the positive electrode active material layer 13B has cracked, the positive electrode active material layer 13B collected from the flat part 10F is preferably examined. A reason for this is that it is possible to accurately and reproducibly examine presence or absence of a crack that has occurred upon charging and discharging.

More specifically, in the curved part 10R where the positive electrode 13 is easily bent upon forming the wound electrode body 10, a large internal stress (distortion) is easily generated due to the bending. This causes a state of the positive electrode active material layer 13B to be varied easily from a state at the time of forming the wound electrode body 10. Thus, in a case where the positive electrode active material layer 13B collected from the curved part 10R is used and where the positive electrode active material layer 13B has cracked, it is difficult to distinguish whether the crack has been generated upon forming the wound electrode body 10 or the crack has been generated upon charging and discharging.

In contrast, in the flat part 10F where the positive electrode 13, for example, is not bent easily at the time of forming the wound electrode body 10, generation of the above-described large inner stress is suppressed, which allows the state of the positive electrode active material layer 13B to be easily maintained as the state at the time of forming. Thus, in a case where the positive electrode active material layer 13B collected from the flat part 10F is used and where the positive electrode active material layer 13B has cracked, it is possible to distinguish whether the crack has been generated upon forming the wound electrode body 10 or the crack has been generated upon charging and discharging.

The secondary battery according to the second embodiment operates as follows, for example. Upon charging the secondary battery, lithium ions are extracted from the positive electrode 13, and the extracted lithium ions are inserted into the negative electrode 14 via the electrolytic solution. Upon discharging the secondary battery, lithium ions are extracted from the negative electrode 14, and the extracted lithium ions are inserted into the positive electrode 13 via the electrolytic solution.

In a case of manufacturing the secondary battery according to the second embodiment, the positive electrode 13 and the negative electrode 14 are fabricated and thereafter the secondary battery is assembled using the positive electrode 13 and the negative electrode 14, for example, as described below.

First, the positive electrode active material including the layered rock-salt lithium-cobalt composite oxide and the positive electrode binder including the vinylidene fluoride-based polymer compound are mixed with materials including, without limitation, the positive electrode conductor on an as-needed basis to thereby obtain a positive electrode mixture. Thereafter, the positive electrode mixture is dispersed or dissolved into a solvent such as an organic solvent to thereby prepare a paste positive electrode mixture slurry. Lastly, the positive electrode mixture slurry is applied on both sides of the positive electrode current collector 13A, following which the applied positive electrode mixture slurry is dried to thereby form the positive electrode active material layers 13B. Thereafter, the positive electrode active material layers 13B may be compression-molded by means of a machine such as a roll pressing machine. In this case, the positive electrode active material layers 13B may be heated. The positive electrode active material layers 13B may be compression-molded a plurality of times.

In a case of fabricating the positive electrode 13, an addition amount of the positive electrode binder, for example, is adjusted to thereby satisfy the above-described configuration condition (the content rate), and a condition at the time of compression molding, for example, is adjusted to thereby satisfy the above-described configuration conditions (the area density and the volume density).

The negative electrode active material layers 14B are provided on both sides of the negative electrode current collector 14A by a procedure similar to the fabrication procedure of the positive electrode 13 described above. Specifically, the negative electrode active material including graphite is mixed with materials including, without limitation, the negative electrode binder and the negative electrode conductor on an as-needed basis to thereby obtain a negative electrode mixture. Thereafter, the negative electrode mixture is dispersed or dissolved into a solvent such as an organic solvent or an aqueous solvent to thereby prepare a paste negative electrode mixture slurry. Thereafter, the negative electrode mixture slurry is applied on both sides of the negative electrode current collector 14A, following which the applied negative electrode mixture slurry is dried to thereby form the negative electrode active material layers 14B. Thereafter, the negative electrode active material layers 14B may be compression-molded.

In the case of fabricating the positive electrode 13 and the negative electrode 14, a mixture ratio between the positive electrode active material and the negative electrode active material (a relationship between mass of the positive electrode active material and mass of the negative electrode active material) is adjusted in such a manner that the mass of the positive electrode active material is sufficiently greater, to thereby satisfy the above-described two configuration conditions (the negative electrode potential Ef and the negative electrode potential variation Ev).

The electrolyte salt is added to the solvent including: the cyclic carbonate ester; and the chain carbonate ester, the chain carboxylate ester, or both. Thereafter, the solvent is stirred. In this case, the mixture ratio of the solvent is adjusted to thereby satisfy the above-described configuration condition (the solvent ratio), and the addition amount of the electrolyte salt, for example, is adjusted to thereby satisfy the above-described configuration condition (the content of the electrolyte salt).

First, the positive electrode lead 11 is coupled to the positive electrode 13 (the positive electrode current collector 13A) by a method such as a welding method, and the negative electrode lead 12 is coupled to the negative electrode 14 (the negative electrode current collector 14A) by a method such as a welding method. Thereafter, the positive electrode 13 and the negative electrode 14 are stacked on each other with the separator 15 interposed therebetween, following which the positive electrode 13, the negative electrode 14, and the separator 15 are wound to thereby form a wound body. In this case, an unillustrated jig having an elongated shape is used to wind the positive electrode 13, the negative electrode 14, and the separator 15 about the winding axis J to thereby cause the wound body to be in the elongated shape as illustrated in FIG. 1.

Thereafter, the outer package member 20 is folded in such a manner as to sandwich the wound electrode body 10, following which the outer edges excluding one side of the outer package member 20 are bonded to each other by a method such as a thermal fusion bonding method. Thus, the wound body is contained in the pouch-shaped outer package member 20. Lastly, the electrolytic solution is injected into the pouch-shaped outer package member 20, following which the outer package member 20 is sealed by a method such as a thermal fusion bonding method. In this case, the sealing film 31 is disposed between the outer package member 20 and the positive electrode lead 11, and the sealing film 32 is disposed between the outer package member 20 and the negative electrode lead 12. The wound body is thereby impregnated with the electrolytic solution, forming the wound electrode body 10. Thus, the wound electrode body 10 is contained in the outer package member 20. As a result, the secondary battery is completed.

According to the secondary battery of the second embodiment, in a case where the positive electrode 13 includes the positive electrode active material (the layered rock-salt lithium-cobalt composite oxide) and the positive electrode binder (the vinylidene fluoride-based polymer compound), where the negative electrode 14 includes the negative electrode active material (graphite), and where the electrolytic solution includes the solvent (the chain carbonate ester, the chain carboxylate ester, or both, in addition to the cyclic carbonate ester): the above-described seven configuration conditions (the negative electrode potential Ef, the negative electrode potential variation Ev, the area density, the volume density, the content rate, the solvent ratio, and the content) may be satisfied. In this case, as compared with the case where the seven configuration conditions are not satisfied, even if the charge voltage Ec is increased to 4.38 V or higher: the potential E of the positive electrode 13 is prevented from easily reaching the potential constant region P2 associated with the phase transition, or the potential E of the positive electrode 13 is prevented from easily passing through the potential constant region P2 associated with the phase transition; precipitation of lithium metal is suppressed on the negative electrode 14; and, in addition, the positive electrode active material layer 13B is prevented from cracking easily. As a result, the capacity loss and the gas generation are suppressed, and the battery capacity is prevented from decreasing easily. In addition, even if the energy density is increased, it becomes easier for the charging and discharging reactions to proceed stably and decomposition of the electrolytic solution is suppressed. Accordingly, it is possible to achieve superior battery characteristics.

In particular, the vinylidene fluoride-based polymer compound may include a material such as polyvinylidene difluoride. This makes it easier for the positive electrode binder to be sufficiently swollen with the electrolytic solution, making it possible to achieve higher effects accordingly. In this case, a copolymerization amount of tetrafluoroethylene in the copolymer may be from 0.1 wt % to 20 wt % both inclusive, or a copolymerization amount of hexafluoropropylene in the copolymer may be from 0.2 wt % to 5 wt % both inclusive. This makes it further easier for the positive electrode binder to be swollen with the electrolytic solution, making it possible to achieve further higher effects accordingly.

Further, the median diameter D50 of the graphite particles may be from 3.5 μm to 30 μm both inclusive. This suppresses the precipitation of lithium metal and also suppresses the occurrence of the side reaction, making it possible to achieve higher effects accordingly. Moreover, the spacing S of the (002) plane of graphite may be from 0.3355 nm to 0.3370 nm both inclusive. This reduces the decomposition reaction of the electrolytic solution while securing the battery capacity, which makes it possible to achieve higher effects accordingly.

A description is given next of a secondary battery according to a third embodiment of the technology. The secondary battery according to the third embodiment has a configuration that is substantially similar to the configuration of the secondary battery according to the first embodiment described above, except for the points described below.

As illustrated in FIG. 3, the negative electrode 14 of the secondary battery according to the third embodiment includes, for example, the negative electrode current collector 14A, and the negative electrode active material layer 14B provided on the negative electrode current collector 14A. The negative electrode active material layer 14B includes, as a negative electrode active material or negative electrode active materials, one or more of negative electrode materials into which lithium ions are insertable and from which lithium ions are extractable. The negative electrode active material layer 14B may further include another material such as a negative electrode binder or a negative electrode conductor.

Here, the negative electrode active material layer 14B includes, for example, two kinds of particulate negative electrode active materials (a plurality of first negative electrode active material particles and a plurality of second negative electrode active material particles). The first negative electrode active material particle includes, as a negative electrode material or negative electrode materials, one or more of carbon materials, and the second negative electrode active material particle includes, as a negative electrode material or negative electrode materials, one or more of materials each including silicon as a constituent element (hereinafter, referred to as a "silicon-containing material").

The term "carbon material" is a generic term for a material mainly including carbon as a constituent element. A reason for this is that a high energy density is stably obtainable owing to the crystal structure of the carbon material which hardly varies upon insertion and extraction of lithium ions. Another reason is that improved electrical conductivity of the negative electrode active material layer 14B is achievable owing to the carbon material which also serves as the negative electrode conductor.

Specifically, the carbon material includes graphite. The graphite is not limited to a particular kind. The graphite may be artificial graphite, natural graphite, or both.

It is preferable that some or all of the plurality of first negative electrode active material particles each including graphite forms so-called secondary particles. A reason for this is that an orientation of the negative electrode 14 (the negative electrode active material layer 14B) is suppressed, thereby suppressing swelling of the negative electrode active material layer 14B upon charging and discharging. With respect to a total weight of the plurality of first negative electrode active material particles, a ratio of a weight occupied by a plurality of first negative electrode active material particles forming the secondary particles is not particularly limited; however, the ratio is preferably from 20 wt % to 80 wt % both inclusive. If the ratio of graphite particles forming the secondary particles is relatively large, a total surface area of the particles is excessively increased due to a relatively small average particle diameter of primary particles, which may cause a decomposition reaction of the electrolytic solution to occur and a capacity per unit weight to be decreased.

The term "silicon-containing material" is a generic term for a material including, as constituent elements, silicon and oxygen. A reason for this is that a markedly high energy density is obtainable. The silicon-containing material may be a simple substance of silicon, a silicon alloy, a silicon compound, a mixture of two or more thereof, or a material including one or more phases thereof.

It should be understood that the simple substance described here merely refers to a simple substance in a general sense. The simple substance may therefore include a small amount of impurity, that is, does not necessarily have a purity of 100%. The term "alloy" encompasses, for example, not only a material that includes two or more metal elements but may also encompass a material that includes one or more metal elements and one or more metalloid elements. The alloy may further include one or more non-metallic elements. The metal-based material has a state such as a solid solution, a eutectic (a eutectic mixture), an intermetallic compound, or a state including two or more thereof that coexist, although not particularly limited thereto.

The silicon alloy includes, as a constituent element or constituent elements other than silicon, for example, one or more of tin, nickel, copper, iron, cobalt, manganese, zinc, indium, silver, titanium, germanium, bismuth, antimony, and chromium. The silicon compound includes, as a constituent element or constituent elements other than silicon, for example, one or both of carbon and oxygen. The silicon compound may include, as a constituent element or constituent elements other than silicon, one or more of the series of constituent elements described in relation to the silicon alloy, for example.

Specific examples of the silicon-containing material include $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, $SiC$, $Si_3N_4$, $Si_2N_2O$, and a silicon oxide represented by Formula (9) below.

$$SiO_v \qquad (9)$$

where v satisfies $0.5 \le v \le 1.5$.

In particular, the silicon oxide is preferable. A reason for this is that the silicon oxide has a relatively large capacity per unit weight and a relatively large capacity per unit volume in graphite ratios. Another reason is that, in the silicon oxide which includes oxygen, a structure thereof is stabilized by an oxygen-silicon bond and a lithium-oxygen bond after being lithiated, thereby suppressing cracking of the particles. The silicon oxide is not limited to a particular kind, and examples thereof include SiO.

A portion of all of a surface of the second negative electrode active material particle may be covered with, for example, one or more of electrically conductive materials such as the carbon material. A reason for this is that an electric resistance of the negative electrode 14 is reduced owing to reduction in an electric resistance of the second negative electrode active material particle. The carbon material is not limited to a particular kind, and examples thereof include amorphous carbon, graphite, graphene, a carbon nanotube, and a carbon nanofiber. A method of forming the electrically conductive material (a method of covering the second negative electrode active material particle) is not particularly limited, and examples thereof include one or more of a deposition method, a sputtering method, and a chemical vapor deposition (CVD) method.

The negative electrode active material may include, for example, one or more of other negative electrode materials together with the two negative electrode materials (the carbon material and the silicon-containing material) described above. Examples of the other negative electrode materials include another carbon material and a metal-based material. A reason for this is that the energy density further increases.

Examples of the other carbon material include non-graphitizable carbon. A reason for this is that a high energy density is stably achievable. A physical property of the non-graphitizable carbon is not particularly limited; however, in particular, spacing of the (002) plane is preferably greater than or equal to 0.37 nm. A reason for this is that a sufficient energy density is achievable.

A charge and discharge principle and configuration conditions of the secondary battery of the third embodiment will now be described.

[Premise and Charge and Discharge Principle]

The premise and the charge and discharge principle related to the secondary battery according to the third embodiment are similar to the premise and the charge and discharge principle related to the secondary battery according to the first embodiment described above.

In the secondary battery according to the third embodiment, five configuration conditions described below are satisfied in order to achieve the charge and discharge principle described above.

First, a state in which the secondary battery is charged with a constant voltage of a closed circuit voltage (CCV) of 4.38 V or higher for 24 hours is referred to as a full charge state. A potential E (a negative electrode potential Ef) of the negative electrode 14 measured in the secondary battery in the full charge state is from 19 mV to 86 mV both inclusive. It should be understood that a value of a current at the time of charging the secondary battery until the closed circuit voltage reaches 4.38 V or higher is not particularly limited, and may thus be set to any value.

That is, as described above, the potential E of the negative electrode 14 is set to cause the charging not to be completed in the potential constant region P3 and to be completed in the potential varying region P4. Accordingly, when the secondary battery is charged to the full charge state, the negative electrode potential Ef is lower in a case where the charging is completed in the potential varying region P4 than in a case where the charging is completed in the potential constant region P3. Thus, the negative electrode potential Ef becomes lower than about 90 mV, and more specifically, from 19 mV to 86 mV both inclusive, as described above.

Second, a discharge capacity obtained when the secondary battery is discharged with a constant current from the full charge state until a closed circuit voltage reaches 3.00 V, following which the secondary battery is discharged with a constant voltage of the closed circuit voltage of 3.00 V for 24 hours is referred to as a maximum discharge capacity (mAh). In this case, when the secondary battery is discharged from the full charge state by a capacity corresponding to 1% of the maximum discharge capacity, a variation of the potential E of the negative electrode 14, i.e., a negative electrode potential variation Ev, represented by Formula (7) below is 1 mV or greater. As is apparent from Formula (7), the negative electrode potential variation Ev is a difference between a potential E1 (a first negative electrode potential) and a potential E2 (a second negative electrode potential). It should be understood that the current value at the time of discharging the secondary battery from the full charge state until the closed circuit voltage reaches 3.00 V is not particularly limited and may be set to any value as long as the current value is within a general range, because the secondary battery is discharged with a constant voltage for 24 hours.

$$\text{Negative electrode potential variation } Ev \text{ (mV)=potential } E2 \text{ (mV)-potential } E1 \text{ (mV)} \quad (7)$$

where:
the potential E1 is an open circuit potential (versus a lithium reference electrode) of the negative electrode 14 measured in the secondary battery in the full charge state; and
the potential E2 is an open circuit potential (versus a lithium reference electrode) of the negative electrode 14 measured in the secondary battery that is discharged from the full charge state by the capacity corresponding to 1% of the maximum discharge capacity.

That is, as described above, in a case where the potential E of the negative electrode 14 is set to cause the charging to be completed in the potential varying region P4, the potential E of the negative electrode 14 increases markedly upon discharging the secondary battery in the full charge state by the capacity corresponding to 1% of the maximum discharge capacity, as is apparent from FIGS. 6 and 7. Thus, the potential E (E2) of the negative electrode 14 after the discharging is sufficiently increased as compared with the potential E (E1) of the negative electrode 14 before the discharging (the full charge state). Accordingly, the negative electrode potential variation Ev, which is the difference between the potential E1 and the potential E2, is 1 mV or greater as described above.

Whether the above two configuration conditions (the negative electrode potential Ef and the negative electrode potential variation Ev) are satisfied is determined in accordance with a ratio between the mass of the positive electrode active material and the mass of the negative electrode active material. Specifically, in a case where the two configuration conditions are satisfied, the mass of the positive electrode active material is relatively large compared with a case where the two configuration conditions are not satisfied. This results in a relatively increased thickness (coating weight) of the positive electrode active material layer 13B in the former case compared with the latter case.

Third, a median diameter D50 of the plurality of first negative electrode active material particles each including graphite (hereinafter, referred to as a "median diameter D50A") is less than or equal to 20 μm, and preferably from 5 μm to 20 μm both inclusive. A reason for this is that it is easier for gaps (vacancies) between the first negative electrode active material particles, which are flowing paths of the electrolytic solution, to be evenly distributed, thereby making lithium ions to be moved easily. This suppresses the precipitation of lithium metal on the negative electrode 14 at the end stage of charging, even if the charge voltage Ec is increased.

Fourth, a volume density of the negative electrode active material layer 14B is greater than or equal to 1.5 g/cm$^3$, and preferably from 1.5 g/cm$^3$ to 1.8 g/cm$^3$ both inclusive. A reason for this is that an energy density increases. An upper-limit volume density is not particularly limited; but if the volume density is greater than 1.8 g/cm$^3$, mobility of the electrolytic solution in the negative electrode 14 may decrease. However, the volume density described here is a bulk density of the negative electrode active material layer 14B excluding the electrolytic solution. In detail, in the completed secondary battery, because the wound electrode body 10 is impregnated with the electrolytic solution as described above, the negative electrode 14 (the negative electrode active material layer 14B) is impregnated with the electrolytic solution. Accordingly, in a case where the volume density is to be measured, the bulk density is measured after the electric solution is sufficiently removed (volatilized) in order to prevent a weight of the electrolytic solution for the impregnation from being added.

Fifth, in a case where the negative electrode active material layer 14B (the first negative electrode active material particles each including graphite) is analyzed by X-ray diffractometry (XRD), an integrated intensity ratio represented by Formula (8) below is less than or equal to 500, and is preferably from 50 to 500 both inclusive.

$$\text{Integrated intensity ratio}=(110) \text{ integrated intensity/} (002) \text{ integrated intensity} \quad (8)$$

where:
the (002) integrated intensity is an integrated intensity of a peak derived from a (002) plane of the graphite, and serves as a first integrated intensity; and
the (110) integrated intensity is an integrated intensity of a peak derived from a (110) plane of the graphite, and serves as a second integrated intensity.

As described above, when the potential E of the negative electrode 14 decreases at the end of charging, a capacity range actually used becomes sufficiently large with respect to the theoretical capacity of the negative electrode 14. For this reason, in a case where the energy density is increased, the precipitation of lithium metal tends to occur on the negative electrode 14.

However, even if the two configuration conditions (the negative electrode potential Ef and the negative electrode potential variation Ev) described above are satisfied, an orientation of the first negative electrode active material particle (graphite) decreases if the above-described configuration condition related to the integrated intensity ratio is satisfied. Specifically, a graphene plane of the graphite is prevented from being easily oriented along a plane (an XY plane) in which the negative electrode active material layer 14B is provided on the negative electrode current collector 14A. Accordingly, a curvature of a fine pore serving as a conductive path of ions in the negative electrode 14 is decreased and polarization is suppressed in the negative electrode 14. This suppresses the precipitation of lithium metal on the surfaces of the first negative electrode active material particles. A lower-limit integrated intensity ratio is not particularly limited; but if the integrated intensity ratio is smaller than 50, the orientation of the graphene plane of the graphite is too low, which may deteriorate productivity and may cause damage to the negative electrode current collector 14A and the separator 15 depending on a shape of the carbon material.

To determine the integrated intensity ratio using XRD, for example, an X-ray diffraction apparatus RAD-IIC available from Rigaku Corporation (optical system=concentration method optical system, source=Cu tube, X-ray wavelength=Cu-Kα, Cu-Kβ, tube voltage=45 kV, and tube current=200 mA) is used to thereby analyze the negative electrode active material layer 14B (the first negative electrode active material particles each including graphite). To detect the peak derived from the (002) plane, a scan range 2θ is set to 24° to 29°, a step is set to 0.02°, a coefficient time is set to 1 second, a divergence slit is set to 0.5°, a scattering slit is set to 0.5°, and a light receiving slit is set to 0.3 mm. To detect the peak derived from the (110) plane, the scan range 2θ is set to 75° to 80°, the step is set to 0.02°, the coefficient time is set to 4 seconds, the divergence slit is set to 2°, the scattering slit is set to 2°, and the light receiving slit is set to 0.3 mm. In a case where analysis data is processed, the analysis data is cut out in such a manner that only a target peak is included by using integrated intensity calculation software (Integral analysis for windows version 6.0), and thereafter, a smoothing process, a BG-removing process, and an integration calculation process are performed. In a case where a degree of orientation is calculated, the degree of orientation is determined as follows: degree of orientation=peak area of (002) plane/peak area of (110) plane/16.

As described above, in the case where the negative electrode active material layer 14B includes the first negative electrode active material particles (graphite) and the second negative electrode active material particles (silicon-containing material), it is preferable that a configuration condition below be further satisfied.

Specifically, a mixture ratio between the first negative electrode active material particles and the second negative electrode active material particles is not particularly limited, and, in particular, a ratio (a content rate) of mass of the second negative electrode active material particles to mass of the first negative electrode active material particles is preferably from 0.1 mass % to 5 mass % both inclusive. A reason for this is that an addition amount of the second negative electrode active material particles is optimized, thereby suppressing the precipitation of lithium metal sufficiently on the negative electrode 14 while securing a high energy density. The content rate is calculated on the basis of a calculation formula: content rate=(mass of second negative electrode active material particles/mass of first negative electrode active material particles)×100.

A median diameter D50 of the second negative electrode active material particles (hereinafter, referred to as a "median diameter D50B") is not particularly limited, however is preferably smaller than the median diameter D50A in particular. A reason for this is that flowing paths of lithium ions are ensured while a high energy density is secured. Specifically, the median diameter D50B is, for example, from 1 μm to 10 μm both inclusive. A reason for this is that a sufficient reactive area with the lithium ions is obtainable.

In a case of examining whether the above-described five configuration conditions are satisfied using the completed secondary battery, the secondary battery is disassembled to thereby collect the negative electrode active material layer 14B. The collected negative electrode active material layer 14B is used to thereby examine the median diameters D50A and D50B, the volume density, and the integrated intensity ratio.

It should be understood that, in a case of examining the above-described median diameter D50A, for example, the negative electrode active material layer 14B collected from the flat part 10F is preferably examined. A reason for this is that it is possible to accurately and reproducibly examine the median diameter D50A, for example.

More specifically, in the curved part 10R where the negative electrode 14 is easily bent upon forming the wound electrode body 10, a large internal stress (distortion) is easily generated due to the bending. This causes a state of the negative electrode 14 to be varied easily from a state at the time of forming the wound electrode body 10. Thus, in a case where the negative electrode active material layer 14B collected from the curved part 10R is used, the median diameter D50A, for example, may possibly be varied from an original value.

In contrast, in the flat part 10F where the negative electrode 14 is not bent easily at the time of forming the wound electrode body 10, generation of the above-described large inner stress is suppressed, which allows the state of the negative electrode active material layer 14B to be easily maintained as the state at the time of forming. Thus, in a case where the negative electrode active material layer 14B collected from the flat part 10F is used, it is possible to examine an original value related to the median diameter D50A, for example.

The secondary battery according to the third embodiment operates as follows, for example. Upon charging the secondary battery, lithium ions are extracted from the positive electrode 13, and the extracted lithium ions are inserted into the negative electrode 14 via the electrolytic solution. Upon discharging the secondary battery, lithium ions are extracted from the negative electrode 14, and the extracted lithium ions are inserted into the positive electrode 13 via the electrolytic solution.

In a case of manufacturing the secondary battery according to the third embodiment, the positive electrode 13 and the negative electrode 14 are fabricated and thereafter the secondary battery is assembled using the positive electrode 13 and the negative electrode 14, for example, as described below.

First, the positive electrode active material including the layered rock-salt lithium-cobalt composite oxide and the positive electrode binder including the vinylidene fluoride-based polymer compound are mixed with materials including, without limitation, the positive electrode conductor on an as-needed basis to thereby obtain a positive electrode mixture. Thereafter, the positive electrode mixture is dispersed or dissolved into a solvent such as an organic solvent to thereby prepare a paste positive electrode mixture slurry. Lastly, the positive electrode mixture slurry is applied on both sides of the positive electrode current collector 13A, following which the applied positive electrode mixture slurry is dried to thereby form the positive electrode active material layers 13B. Thereafter, the positive electrode active material layers 13B may be compression-molded by means of a machine such as a roll pressing machine. In this case, the positive electrode active material layers 13B may be heated. The positive electrode active material layers 13B may be compression-molded a plurality of times.

The negative electrode active material layers 14B are provided on both sides of the negative electrode current collector 14A by a procedure similar to the fabrication procedure of the positive electrode 13 described above. Specifically, the negative electrode active material including the first negative electrode active material particles (graphite) and the second negative electrode active material particles (the silicon-containing material) is mixed with materials including, without limitation, the negative electrode binder and the negative electrode conductor on an as-needed basis to thereby obtain a negative electrode mixture. Thereafter, the negative electrode mixture is dispersed or dissolved into a solvent such as an organic solvent or an aqueous solvent to thereby prepare a paste negative electrode mixture slurry. Thereafter, the negative electrode mixture slurry is applied on both sides of the negative electrode current collector 14A, following which the applied negative electrode mixture slurry is dried to thereby form the negative electrode active material layers 14B. Thereafter, the negative electrode active material layers 14B may be compression-molded.

In the case of fabricating the negative electrode 14, the respective kinds of the first negative electrode active material particles and the second negative electrode active material particles, for example, are adjusted to thereby satisfy the above-described configuration conditions (the median diameters D50A and D50B and the integrated intensity ratio), and a condition at the time of compression molding, for example, is adjusted to thereby satisfy the above-described configuration condition (the volume density).

In the case of providing the electrically conductive material (the carbon material) on the surface of the second negative electrode active material particle, the electrically conductive material is deposited on the surface of the second negative electrode active material particle by a CVD method, for example, using a carbon source as a raw material.

In the case of fabricating the positive electrode 13 and the negative electrode 14, a mixture ratio between the positive electrode active material and the negative electrode active material (a relationship between mass of the positive electrode active material and mass of the negative electrode active material) is adjusted in such a manner that the mass of the positive electrode active material is sufficiently greater, to thereby satisfy the above-described two configuration conditions (the negative electrode potential Ef and the negative electrode potential variation Ev).

First, the positive electrode lead 11 is coupled to the positive electrode 13 (the positive electrode current collector 13A) by a method such as a welding method, and the negative electrode lead 12 is coupled to the negative electrode 14 (the negative electrode current collector 14A) by a method such as a welding method. Thereafter, the positive electrode 13 and the negative electrode 14 are stacked on each other with the separator 15 interposed therebetween, following which the positive electrode 13, the negative electrode 14, and the separator 15 are wound to thereby form a wound body. In this case, an unillustrated jig having an elongated shape is used to wind the positive electrode 13, the negative electrode 14, and the separator 15 about the winding axis J to thereby cause the wound body to be in the elongated shape as illustrated in FIG. 1.

Thereafter, the outer package member 20 is folded in such a manner as to sandwich the wound electrode body 10, following which the outer edges excluding one side of the outer package member 20 are bonded to each other by a method such as a thermal fusion bonding method. Thus, the wound body is contained in the pouch-shaped outer package member 20. Lastly, the electrolytic solution is injected into the pouch-shaped outer package member 20, following which the outer package member 20 is sealed by a method such as a thermal fusion bonding method. In this case, the sealing film 31 is interposed between the outer package member 20 and the positive electrode lead 11, and the sealing film 32 is interposed between the outer package member 20 and the negative electrode lead 12. The wound body is thereby impregnated with the electrolytic solution, forming the wound electrode body 10. Thus, the wound electrode body 10 is contained in the outer package member 20. As a result, the secondary battery is completed.

According to the secondary battery of the third embodiment, in a case where the positive electrode 13 includes the positive electrode active material (the layered rock-salt lithium-cobalt composite oxide) and where the negative electrode 14 (the first negative electrode active material particles) includes graphite: the above-described five configuration conditions (the negative electrode potential Ef, the negative electrode potential variation Ev, the median diameter D50A, the volume density, and the integrated intensity ratio) may be satisfied. In this case, as compared with the case where the five configuration conditions are not satisfied, even if the charge voltage Ec is increased to 4.38 V or higher: the potential E of the positive electrode 13 is further prevented from easily reaching the potential constant region P2 associated with the phase transition, or the potential E of the positive electrode 13 is further prevented from easily passing through the potential constant region P2 associated with the phase transition; and the precipitation of lithium metal is suppressed on the negative electrode 14. As a result, the capacity loss and the gas generation are suppressed. In addition, the decrease in battery capacity is suppressed. Accordingly, it is possible to achieve superior battery characteristics.

In particular, the spacing S of the (002) plane of graphite may be from 0.3355 nm to 0.3370 nm both inclusive. This reduces the decomposition reaction of the electrolytic solution while securing the battery capacity, which makes it possible to achieve higher effects accordingly.

Further, the negative electrode 14 may include the first negative electrode active material particles (graphite) and the second negative electrode active material particles (the silicon-containing material). This greatly increases an amount of lithium insertion per unit mass of the negative electrode active material included in the negative electrode 14, making it possible to achieve higher effects accordingly. In contrast, for example, in a case where non-graphitizable carbon having a high acceptability of lithium ions as compared to graphite is used as the second negative electrode active material particles, the amount of lithium insertion per unit mass of the negative electrode active material included in the negative electrode 14 does not greatly increase. Thus, obtainable effects are limited as compared with the case of using graphite.

Still further, the silicon-containing material may include silicon oxide. This prevents the negative electrode active material from cracking easily while securing, for example, a capacity per unit mass, making it possible to achieve further higher effects accordingly. The content rate may be from 0.1 mass % to 5 mass % both inclusive. This further suppresses the precipitation of lithium metal while securing a high energy density, which makes it possible to achieve further higher effects accordingly. The median diameter D50B may be smaller than the median diameter D50A, and more specifically, the median diameter D50B may be from 1 µm to 10 µm both inclusive. This ensures the sufficient reactive area with the lithium ions while securing a high energy density, making it possible to achieve further higher effects accordingly.

Moreover, a portion or all of a surface of the second negative electrode active material particle may be covered with the carbon material. This reduces the electric resistance of the negative electrode 14, making it possible to achieve higher effects accordingly. In this case, the carbon material may be a material such as amorphous carbon. This sufficiently reduces the electric resistance of the negative electrode 14, making it possible to achieve further higher effects accordingly.

A description is given next of a secondary battery according to a fourth embodiment of the technology. The secondary battery according to the fourth embodiment has a configuration that is substantially similar to the configuration of the secondary battery according to the first embodiment described above, except for the points described below.

As illustrated in FIG. 3, the positive electrode 13 of the secondary battery according to the fourth embodiment includes, for example, the positive electrode current collector 13A, and the positive electrode active material layer 13B provided on the positive electrode current collector 13A. The positive electrode current collector 13A includes, for example, one or more of electrically conductive materials including, without limitation, aluminum and an aluminum alloy. The aluminum alloy will be described later in detail.

A charge and discharge principle and configuration conditions of the secondary battery according to the fourth embodiment will now be described.

The premise and the charge and discharge principle related to the secondary battery according to the fourth embodiment are similar to the premise and the charge and discharge principle related to the secondary battery according to the first embodiment described above.

In the secondary battery according to the fourth embodiment, three configuration conditions described below are satisfied in order to achieve the charge and discharge principle described above.

First, a state in which the secondary battery is charged with a constant voltage of a closed circuit voltage (CCV) of 4.38 V or higher for 24 hours is referred to as a full charge state. A potential E (a negative electrode potential Ef) of the negative electrode 14 measured in the secondary battery in the full charge state is from 19 mV to 86 mV both inclusive. It should be understood that a value of a current at the time of charging the secondary battery until the closed circuit voltage reaches 4.38 V or higher is not particularly limited, and may thus be set to any value.

That is, as described above, the potential E of the negative electrode 14 is set to cause the charging not to be completed in the potential constant region P3 and to be completed in the potential varying region P4. Accordingly, when the secondary battery is charged to the full charge state, the negative electrode potential Ef is lower in a case where the charging is completed in the potential varying region P4 than in a case where the charging is completed in the potential constant region P3. Thus, the negative electrode potential Ef becomes lower than about 90 mV, and more specifically, from 19 mV to 86 mV both inclusive, as described above.

Second, a discharge capacity obtained when the secondary battery is discharged with a constant current from the full charge state until a closed circuit voltage reaches 3.00 V, following which the secondary battery is discharged with a constant voltage of the closed circuit voltage of 3.00 V for 24 hours is referred to as a maximum discharge capacity (mAh). In this case, when the secondary battery is discharged from the full charge state by a capacity corresponding to 1% of the maximum discharge capacity, a variation of the potential E of the negative electrode 14, i.e., a negative electrode potential variation Ev, represented by Formula (11) below is 1 mV or greater. As is apparent from Formula (11), the negative electrode potential variation Ev is a difference between a potential E1 (a first negative electrode potential) and a potential E2 (a second negative electrode potential). It should be understood that the current value at the time of discharging the secondary battery from the full charge state until the closed circuit voltage reaches 3.00 V is not particularly limited and may be set to any value as long as the current value is within a general range, because the secondary battery is discharged with a constant voltage for 24 hours.

$$\text{Negative electrode potential variation } Ev \text{ (mV)} = \text{potential } E2 \text{ (mV)} - \text{potential } E1 \text{ (mV)} \quad (11)$$

where:

the potential E1 is an open circuit potential (versus a lithium reference electrode) of the negative electrode 14 measured in the secondary battery in the full charge state; and the potential E2 is an open circuit potential (versus a lithium reference electrode) of the negative electrode 14 measured in the secondary battery that is discharged from the full charge state by the capacity corresponding to 1% of the maximum discharge capacity.

That is, as described above, in a case where the potential E of the negative electrode 14 is set to cause the charging to be completed in the potential varying region P4, the potential E of the negative electrode 14 increases markedly upon discharging the secondary battery in the full charge state by the capacity corresponding to 1% of the maximum discharge capacity, as is apparent from FIGS. 6 and 7. Thus, the potential E (E2) of the negative electrode 14 after the discharging is sufficiently increased as compared with the potential E (E1) of the negative electrode 14 before the discharging (the full charge state). Accordingly, the negative electrode potential variation Ev, which is the difference between the potential E1 and the potential E2, is 1 mV or greater as described above.

Whether the two configuration conditions (the negative electrode potential Ef and the negative electrode potential variation Ev) are satisfied is determined in accordance with a ratio between the mass of the positive electrode active material and the mass of the negative electrode active material. Specifically, in a case where the two configuration conditions are satisfied, the mass of the positive electrode active material is relatively large compared with a case where the two configuration conditions are not satisfied. This results in a relatively increased thickness (coating weight) of the positive electrode active material layer 13B in the former case compared with the latter case.

Third, a degree of durability of the positive electrode 13 in the pair of curved parts 10R of the wound electrode body 10 represented by Formula (12) below is less than or equal to 200.

Degree of durability=(area density (mg/cm$^2$) of positive electrode active material layer 13B×volume density (g/cm$^3$) of positive electrode active material layer 13B)/piercing strength (N) of positive electrode 13   (12)

In a case where the two configuration conditions (the negative electrode potential Ef and the negative electrode potential variation Ev) are satisfied, the potential E of the positive electrode 13 does not increase excessively at the end of charging, but the potential E of the negative electrode 14 decreases markedly at the end of charging. As a result, a capacity range actually used becomes sufficiently large with respect to the theoretical capacity of the negative electrode 14, which easily causes swelling of the secondary battery in the end stage of charging.

In this case, as described above, in the case where the thickness of the positive electrode active material layer 13B is relatively increased and where the use range of the capacity of the negative electrode 14 with respect to the theoretical capacity of the negative electrode 14 is large as compared to a typical secondary battery, a crack easily occur in the positive electrode active material layer 13B due to the swelling of the secondary battery. The tendency of crack occurrence is particularly remarkable in the curved part 10R where a large internal stress (distortion) is easily generated due to bending of the positive electrode 13 in the process of forming the wound electrode body 10. The occurrence of a crack in the positive electrode active material layer 13B makes it difficult for the charging and discharging reactions to proceed stably, and makes it easier for the electrolytic solution to be decomposed upon charging and discharging. Accordingly, battery characteristics are deteriorated.

However, in a case where the two configuration conditions are satisfied and where the configuration condition described above related to the degree of durability is satisfied, a physical durability of the positive electrode 13 (the positive electrode active material layer 13B) is secured in the curved part 10R. Accordingly, the occurrence of a crack is suppressed in the positive electrode active material layer 13B even if the secondary battery swells in the end stage of charging. In this case, in particular, the occurrence of a crack is sufficiently suppressed even if the charge voltage Ec is increased to 4.38 V or higher.

The degree of durability is determined substantially on the basis of the piercing strength of the positive electrode 13, and the piercing strength of the positive electrode 13 is determined substantially on the basis of the strength of the positive electrode current collector 13A which is harder than the positive electrode active material layer 13B. A reason why the configuration condition (degree of durability) described above is satisfied is that the positive electrode current collector 13A has a sufficient strength (hardness).

The area density of the positive electrode active material layer 13B is not particularly limited, and is, for example, from 20.0 mg/cm$^2$ to 50.0 mg/cm$^2$ both inclusive. The volume density of the positive electrode active material layer 13B is not particularly limited, and is, for example, from 3.5 g/cm$^3$ to 4.3 g/cm$^3$ both inclusive. The piercing strength of the positive electrode 13 is not particularly limited, and is, for example, from 0.8 N to 1.2 N both inclusive. A reason for those is that it becomes easier to satisfy and maintain the above-described configuration condition (the degree of durability). It should be understood that, for example, in a case where the positive electrode current collector 13A includes aluminum, the aluminum alloy, or both, the positive electrode current collector 13A has a thickness of, for example, from 8 μm to 30 μm both inclusive. A reason for this is that it becomes easier to satisfy the above-described configuration condition (the degree of durability) in a case where the positive electrode current collector 13A includes a substance such as aluminum.

The degree of durability is an index representing the physical durability of the positive electrode 13 (the positive electrode active material layer 13B), and is calculated on the basis of Formula (12) described above after the area density and the volume density of the positive electrode active material layer 13B and the piercing strength of the positive electrode 13 are measured.

Here, in a case of calculating the area density, first, the secondary battery is disassembled to thereby collect the wound electrode body 10. Thereafter, the positive electrode 13, the negative electrode 14, and the separator 15 wound about the winding axis J are loosened, following which the positive electrode 13 is cut in a region corresponding to the curved part 10R to thereby retrieve a sample (the positive electrode current collector 13A and the positive electrode active material layer 13B) for calculating the area density. In this case, the positive electrode 13 is cut at any position of the region corresponding to the curved part 10R in such a manner as to have a rectangular shape having a predetermined area (cm$^2$). Thereafter, a weight (g) of the sample is measured, following which the positive electrode current collector 13A is peeled from the positive electrode active material layer 13B to thereby measure a weight (g) of the positive electrode current collector 13A. Thereafter, a weight (g) of the positive electrode active material layer 13B is calculated by subtracting the weight of the positive electrode current collector 13A from the weight of the sample. Lastly, the area density is calculated on the basis of the area of the sample (the positive electrode active material layer 13B) and the weight of the positive electrode active material layer 13B described above.

In a case of calculating the volume density, for example, a procedure similar to that in the case of calculating the area density is used, except that the volume of the positive electrode active material layer 13B is measured instead of the area of the positive electrode active material layer 13B, following which the volume density is calculated on the basis of the volume and the weight of the positive electrode active material layer 13B.

Figure 8:
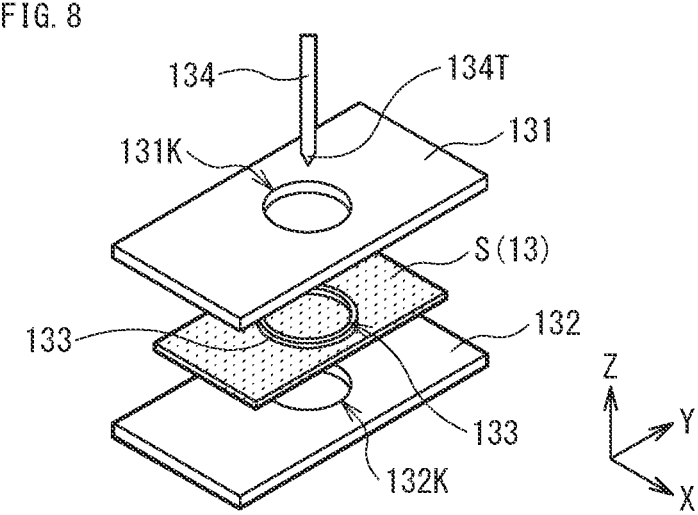
FIG. 8 is a perspective view for describing a method of measuring a piercing strength according to an embodiment of the present technology.
Figure 9:
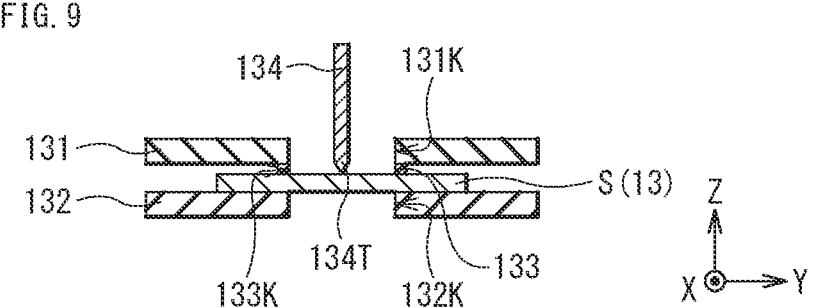
FIG. 9 is a sectional view for describing a measuring process that follows a measuring process illustrated in FIG. 8.
Figure 10:
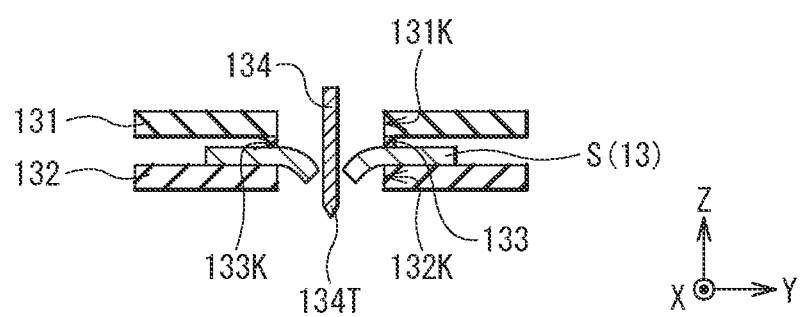
FIG. 10 is a sectional view for describing a measuring process that follows the measuring process illustrated in FIG. 9.

In a case of determining the piercing strength, for example, a piercing test described below is performed. FIGS. 8 to 10 illustrate a perspective view and sectional views of a configuration of a sample S (the positive electrode 13) in order to describe a method of measuring the piercing strength.

In the piercing test, first, the sample S (the positive electrode 13 including the positive electrode current collector 13A and the positive electrode active material layer 13B) is retrieved from the secondary battery by the above-described procedure. Thereafter, as illustrated in FIGS. 8 and 9, a substrate 131 having an opening 131K, a substrate 132 having an opening 132K, a ring 133 including rubber and having an opening 133K, and a piercing jig 134 having a substantially cylindrical shape that includes an end portion 134T having a pointed shape are prepared. An inner diameter of each of the openings 131K, 132K, and 133K is, for example, 10 mm. An outer diameter of the ring 133 is, for example, 13 mm. An outer diameter of the piercing jig 134 is, for example, 2 mm. Thereafter, the sample S, the ring 133, and the substrate 131 are stacked in this order on the substrate 132. In this case, the substrates 131 and 132 and the ring 133 are aligned with each other in such a manner that respective positions of the openings 131K, 132K, and 133K match each other. In FIG. 8, the sample S is shaded.

Lastly, as illustrated in FIG. 8, the piercing jig 134 is disposed in such a manner that the end portion 134T opposes the sample S and that the end portion 134T extends in a direction (a Z-axis direction) intersecting an extending surface (the XY plane) of the sample S. Thereafter, a load (N) applied to piercing jig 134 is measured while moving the piercing jig 134 toward the sample S, as illustrated in FIGS. 9 and 10. In this case, the piercing jig 134 is moved at a rate of 50 mm/min until the end portion 134T comes into contact with the sample S and breaks through the sample S. Thus, for example, in a case where the positive electrode active material layer 13B is provided on each of both sides of the positive electrode current collector 13A, the piercing jig 134 penetrates the positive electrode active material layer 13B, the positive electrode current collector 13A, and the positive electrode active material layer 13B in this order. On the basis of measurement results of the load, a maximum value of the load is set as the piercing strength.

However, a value of the area density is a value obtained by rounding off to the first decimal place. A value of the volume density is a value obtained by rounding off to the first decimal place. A value of piercing strength is a value obtained by rounding off to the first decimal place. A value of the degree of durability is a value obtained by rounding off to the nearest whole number.

It should be understood that the piercing strength which greatly influences the degree of durability is adjustable depending on, for example, a composition and a manufacturing condition of the positive electrode current collector 13A.

For example, in a case where the positive electrode current collector 13A includes the aluminum alloy, the composition of the positive electrode current collector 13A is a composition of the aluminum alloy, and more specifically, refers to a kind of aluminum alloy and a content of a component other than aluminum, for example. The aluminum alloy is not limited to a particular kind, and examples thereof include an aluminum-iron alloy, an aluminum-silicon alloy and an aluminum-copper alloy. In particular, inclusion of the aluminum-silicon alloy tends to increase the piercing strength, and increase in the content of silicon in the aluminum-silicon alloy increases the piercing strength.

For example, in a case where a metal foil is rolled while being heated to manufacture the positive electrode current collector 13A, manufacturing conditions of the positive electrode current collector 13A include, for example, a heating temperature, a temperature variation pattern at the time of heating, a rolling method, and the like. With increase in the piercing strength of the metal foil in accordance with the above-described composition, it generally tends to become difficult to roll the metal foil.

The secondary battery according to the fourth embodiment operates as follows, for example. Upon charging the secondary battery, lithium ions are extracted from the positive electrode 13, and the extracted lithium ions are inserted into the negative electrode 14 via the electrolytic solution. Upon discharging the secondary battery, lithium ions are extracted from the negative electrode 14, and the extracted lithium ions are inserted into the positive electrode 13 via the electrolytic solution.

In a case of manufacturing the secondary battery according to the fourth embodiment, the positive electrode 13 and the negative electrode 14 are fabricated and thereafter the secondary battery is assembled using the positive electrode 13 and the negative electrode 14, for example, as described below.

First, the positive electrode active material including the layered rock-salt lithium-cobalt composite oxide is mixed with materials including, without limitation, the positive electrode binder and the positive electrode conductor on an as-needed basis to thereby obtain a positive electrode mixture. Thereafter, the positive electrode mixture is dispersed or dissolved into a solvent such as an organic solvent to thereby prepare a paste positive electrode mixture slurry. Lastly, the positive electrode mixture slurry is applied on both sides of the positive electrode current collector 13A, following which the applied positive electrode mixture slurry is dried to thereby form the positive electrode active material layers 13B. Thereafter, the positive electrode active material layers 13B may be compression-molded by means of a machine such as a roll pressing machine. In this case, the positive electrode active material layers 13B may be heated. The positive electrode active material layers 13B may be compression-molded a plurality of times.

In a case of fabricating the positive electrode 13, a composition and a manufacturing condition of the positive electrode current collector 13A, for example, are adjusted to thereby satisfy the above-described configuration condition (the degree of durability).

The negative electrode active material layers 14B are provided on both sides of the negative electrode current collector 14A by a procedure similar to the fabrication procedure of the positive electrode 13 described above. Specifically, the negative electrode active material including graphite is mixed with materials including, without limitation, the negative electrode binder and the negative electrode conductor on an as-needed basis to thereby obtain a negative electrode mixture. Thereafter, the negative electrode mixture is dispersed or dissolved into a solvent such as an organic solvent or an aqueous solvent to thereby prepare a paste negative electrode mixture slurry. Thereafter, the negative electrode mixture slurry is applied on both sides of the negative electrode current collector 14A, following which the applied negative electrode mixture slurry is dried to thereby form the negative electrode active material layers 14B. Thereafter, the negative electrode active material layers 14B may be compression-molded.

In the case of fabricating the positive electrode 13 and the negative electrode 14, a mixture ratio between the positive electrode active material and the negative electrode active material (a relationship between mass of the positive electrode active material and mass of the negative electrode active material) is adjusted in such a manner that the mass of the positive electrode active material is sufficiently greater, to thereby satisfy the above-described two configuration conditions (the negative electrode potential Ef and the negative electrode potential variation Ev).

First, the positive electrode lead 11 is coupled to the positive electrode 13 (the positive electrode current collector 13A) by a method such as a welding method, and the negative electrode lead 12 is coupled to the negative electrode 14 (the negative electrode current collector 14A) by a method such as a welding method. Thereafter, the positive electrode 13 and the negative electrode 14 are stacked on each other with the separator 15 interposed therebetween, following which the positive electrode 13, the negative electrode 14, and the separator 15 are wound to thereby form a wound body. In this case, an unillustrated jig having an elongated shape is used to wind the positive electrode 13, the negative electrode 14, and the separator 15 about the winding axis J to thereby cause the wound body to be in the elongated shape as illustrated in FIG. 1.

Thereafter, the outer package member 20 is folded in such a manner as to sandwich the wound electrode body 10, following which the outer edges excluding one side of the outer package member 20 are bonded to each other by a method such as a thermal fusion bonding method. Thus, the wound body is contained in the pouch-shaped outer package member 20. Lastly, the electrolytic solution is injected into the pouch-shaped outer package member 20, following which the outer package member 20 is sealed by a method such as a thermal fusion bonding method. In this case, the sealing film 31 is interposed between the outer package member 20 and the positive electrode lead 11, and the sealing film 32 is interposed between the outer package member 20 and the negative electrode lead 12. The wound body is thereby impregnated with the electrolytic solution, forming the wound electrode body 10, and the wound electrode body 10 is also contained in the outer package member 20. As a result, the secondary battery is completed.

According to the secondary battery of the fourth embodiment, in a case where the wound electrode body 10 has an elongated shape, where the positive electrode 13 includes the positive electrode active material (the layered rock-salt lithium-cobalt composite oxide), and where the negative electrode 14 includes the negative electrode active material (graphite): the above-described three configuration conditions (the negative electrode potential Ef, the negative electrode potential variation Ev, and the degree of durability) may be satisfied. In this case, as compared with the case where the three configuration conditions are not satisfied, even if the charge voltage Ec is increased to 4.38 V or higher: the potential E of the positive electrode 13 is prevented from easily reaching the potential constant region P2 associated with the phase transition, or the potential E of the positive electrode 13 is prevented from easily passing through the potential constant region P2 associated with the phase transition; the precipitation of lithium metal is suppressed on the negative electrode 14; and, in addition, the occurrence of a crack is suppressed in the positive electrode active material layer 13B. As a result, not only the capacity loss and the gas generation are suppressed, but also the decrease in battery capacity is suppressed. In addition, it becomes easier for the charging and discharging reactions to proceed stably and decomposition of the electrolytic solution is suppressed upon charging and discharging. This further suppresses the capacity loss and the gas generation, and further suppresses the decrease in battery capacity. Accordingly, it is possible to achieve superior battery characteristics.

In particular, the positive electrode current collector 13A may include a substance such as aluminum. This makes it easier to satisfy the configuration condition (the degree of durability) in the case where the positive electrode current collector 13A includes the substance such as aluminum, making it possible to achieve higher effects accordingly.

In this case, the area density of the positive electrode active material layer 13B may be from 20.0 mg/cm$^2$ to 50.0 mg/cm$^2$ both inclusive and the volume density of the positive electrode active material layer 13B may be from 3.5 g/cm$^3$ to 4.3 g/cm$^3$ both inclusive. This makes it further easier to satisfy the above-described configuration condition (the degree of durability), making it possible to achieve further higher effects accordingly.

A description is given next of a secondary battery according to a fifth embodiment of the technology. The secondary battery according to the fifth embodiment has a configuration that is substantially similar to the configuration of the secondary battery according to the first embodiment described above, except for the points described below.

As illustrated in FIG. 3, the separator 15 included in the secondary battery according to the fifth embodiment is interposed between the positive electrode 13 and the negative electrode 14, and is adhered to the positive electrode 13 (the positive electrode active material layer 13B) and to the negative electrode 14 (the negative electrode active material layer 14B).

Specifically, the separator 15 includes, for example, a base layer 15A, two polymer compound layers 15B (a positive electrode-side polymer compound layer 15BX and a negative electrode-side polymer compound layer 15BY) each provided on corresponding one of both sides of the base layer 15A. A reason why the positive electrode-side polymer compound layer 15BX is provided on the base layer 15A is that adhesion of the separator 15 to the positive electrode active material layer 13B improves. A reason why the negative electrode-side polymer compound layer 15BY is provided on the base layer 15A is that adhesion of the separator 15 to the negative electrode active material layer 14B improves.

The base layer 15A includes a porous film of a material such as a synthetic resin or ceramic, for example. The base layer 15A may be a stacked film including two or more porous films that are stacked on each other, in one example. Examples of the synthetic resin include polyethylene.

The positive electrode-side polymer compound layer 15BX is a second polymer compound layer interposed between the base layer 15A and the positive electrode active material layer 13B, and is adhered to the positive electrode active material layer 13B. The negative electrode-side polymer compound layer 15BY is a first polymer compound layer interposed between the base layer 15A and the negative electrode active material layer 14B, and is adhered to the negative electrode active material layer 14B. The positive electrode-side polymer compound layer 15BX and the negative electrode-side polymer compound layer 15BY each include, for example, one or more of polymer compounds. A kind of the polymer compound included in the positive electrode-side polymer compound layer 15BX and a kind of the polymer compound included in the negative electrode-side polymer compound layer 15BY may be the same as or different from each other.

The polymer compound is not limited to a particular kind, and in particular, the above-described fluorine-based polymer compound is preferable. A reason for this is that adhesion of the positive electrode active material layer 13B to the separator 15 (the positive electrode-side polymer compound layer 15BX) improves and adhesion of the negative electrode active material layer 14B to the separator 15 (the negative electrode-side polymer compound layer 15BY) improves. Details on the fluorine-based polymer compound are as described above.

In particular, in a case where the positive electrode active material layer 13B includes the fluorine-based polymer compound as the positive electrode binder and where the positive electrode-side polymer compound layer 15BX also includes the fluorine-based polymer compound, the adhesion of the positive electrode active material layer 13B to the separator 15 (the positive electrode-side polymer compound layer 15BX) markedly improves. Similarly, in a case where the negative electrode active material layer 14B includes the fluorine-based polymer compound as the negative electrode binder and where the negative electrode-side polymer compound layer 15BY also includes the fluorine-based polymer compound, the adhesion of the negative electrode active material layer 14B to the separator 15 (the negative electrode-side polymer compound layer 15BY) markedly improves.

It should be understood that the positive electrode-side polymer compound layer 15BX and the negative electrode-side polymer compound layer 15BY may each include a plurality of insulating particles. A reason for this is that, at the time of heat generation in the secondary battery, the insulating particles absorb heat, and at the time of damage occurrence (for example, melting) in the separator 15, the insulating particles electrically separate the positive electrode 13 and the negative electrode 14 from each other, thereby improving safety. The insulating particles are not limited to a particular kind, and examples thereof include a plurality of inorganic particles. The inorganic particles each include one or more of compounds including, without limitation, aluminum oxide and aluminum nitride.

A charge and discharge principle and configuration conditions of the secondary battery according to the fifth embodiment will now be described.

The premise and the charge and discharge principle related to the secondary battery according to the fifth embodiment are similar to the premise and the charge and discharge principle related to the secondary battery according to the first embodiment described above.

In the secondary battery according to the fifth embodiment, three configuration conditions described below are satisfied in order to achieve the charge and discharge principle described above.

First, a state in which the secondary battery is charged with a constant voltage of a closed circuit voltage (CCV) of 4.38 V or higher for 24 hours is referred to as a full charge state. A potential E (a negative electrode potential Ef) of the negative electrode 14 measured in the secondary battery in the full charge state is from 19 mV to 86 mV both inclusive. It should be understood that a value of a current at the time of charging the secondary battery until the closed circuit voltage reaches 4.38 V or higher is not particularly limited, and may thus be set to any value.

That is, as described above, the potential E of the negative electrode 14 is set to cause the charging not to be completed in the potential constant region P3 and to be completed in the potential varying region P4. Accordingly, when the secondary battery is charged to the full charge state, the negative electrode potential Ef is lower in a case where the charging is completed in the potential varying region P4 than in a case where the charging is completed in the potential constant region P3. Thus, the negative electrode potential Ef becomes lower than about 90 mV, and more specifically, from 19 mV to 86 mV both inclusive, as described above.

Second, a discharge capacity obtained when the secondary battery is discharged with a constant current from the full charge state until a closed circuit voltage reaches 3.00 V, following which the secondary battery is discharged with a constant voltage of the closed circuit voltage of 3.00 V for 24 hours is referred to as a maximum discharge capacity (mAh). In this case, when the secondary battery is discharged from the full charge state by a capacity corresponding to 1% of the maximum discharge capacity, a variation of the potential E of the negative electrode 14, i.e., a negative electrode potential variation Ev, represented by Formula (14) below is 1 mV or greater. As is apparent from Formula (14), the negative electrode potential variation Ev is a difference between a potential E1 (a first negative electrode potential) and a potential E2 (a second negative electrode potential). It should be understood that the current value at the time of discharging the secondary battery from the full charge state until the closed circuit voltage reaches 3.00 V is not particularly limited and may be set to any value as long as the current value is within a general range, because the secondary battery is discharged with a constant voltage for 24 hours.

$$\text{Negative electrode potential variation } Ev \text{ (mV)} = \text{potential } E2 \text{ (mV)} - \text{potential } E1 \text{ (mV)} \tag{14}$$

where:
the potential E1 is an open circuit potential (versus a lithium reference electrode) of the negative electrode 14 measured in the secondary battery in the full charge state; and
the potential E2 is an open circuit potential (versus a lithium reference electrode) of the negative electrode 14 measured in the secondary battery that is discharged from the full charge state by the capacity corresponding to 1% of the maximum discharge capacity.

That is, as described above, in a case where the potential E of the negative electrode 14 is set to cause the charging to be completed in the potential varying region P4, the potential E of the negative electrode 14 increases markedly upon discharging the secondary battery in the full charge state by the capacity corresponding to 1% of the maximum discharge capacity, as is apparent from FIGS. 6 and 7. Thus, the potential E (E2) of the negative electrode 14 after the discharging is sufficiently increased as compared with the potential E (E1) of the negative electrode 14 before the discharging (the full charge state). Accordingly, the negative electrode potential variation Ev, which is the difference between the potential E1 and the potential E2, is 1 mV or greater as described above.

Third, an adhesive strength FA of the negative electrode 14 (the negative electrode active material layer 14B) to the separator 15 (the negative electrode-side polymer compound layer 15BY) is from 5 mN/mm to 100 mN/mm both inclusive, and preferably from 10 mN/mm to 40 mN/mm both inclusive.

In the case where the two configuration conditions (the negative electrode potential Ef and the negative electrode potential variation Ev) are satisfied, the potential E of the positive electrode 13 is not excessively increased at the end of charging, but the potential E of the negative electrode 14 is markedly decreased at the end of charging. As a result, the capacity range actually used becomes sufficiently large with respect to the theoretical capacity of the negative electrode 14, which easily causes the swelling of the secondary battery at the end of charging. If the negative electrode 14 is peeled off from the separator 15 due to the swelling of the secondary battery, it makes it difficult for the charging and discharging reactions to proceed stably, and makes it easier for the electrolytic solution to be decomposed upon charging and discharging. Accordingly, battery characteristics are deteriorated. However, in a case where the two configuration conditions are satisfied and where the configuration condition related to the adhesive strength FA described above is also satisfied, adhesion of the negative electrode 14 to the separator 15 is secured. This prevents the negative electrode 14 from be being easily peeled off from the separator 15 even if the charge voltage Ec is increased to 4.38 V or higher.

Here, for example, an adhesive strength FC of the positive electrode 13 (the positive electrode active material layer 13B) to the separator 15 (the positive electrode-side polymer compound layer 15BX) is likewise from 5 mN/mm to 100 mN/m both inclusive, and preferably from 10 mN/mm to 40 mN/mm both inclusive. A reason for this is that the adhesion of the positive electrode 13 to the separator 15 is secured for a reason similar to that for the adhesive strength FA described above, which prevents the positive electrode 13 from being easily peeled off from the separator 15 even if the charge voltage Ec is increased to 4.38 V or higher.

The respective configuration conditions described above for the adhesive strength FC and the adhesive strength FA are satisfied because, as will be described later, the wound electrode body 10 is hot-pressed in a process of manufacturing the secondary battery (at the time of initial-cycle charging), in other words, the wound electrode body 10 is heated while being applied with pressure. The hot pressing improves the adhesion of the positive electrode active material layer 13B to the separator 15 (the positive electrode-side polymer compound layer 15BX) and also improves the adhesion of the negative electrode active material layer 14B to the separator 15 (the negative electrode-side polymer compound layer 15BY). Details of the hot-pressing of the secondary battery will be described later.

A method of measuring the adhesive strengths FC and FA are as follows, for example. Here, a procedure of measuring, for example, the adhesive strength FA will be described. The procedure of measuring the adhesive strength FC is similar to the procedure of measuring the adhesive strength FA, except that the positive electrode 13 is used instead of the negative electrode 14.

In a case of measuring the adhesive strength FA, first, a secondary battery is prepared. In a case where a secondary battery in a charged state is to be used, the secondary battery is discharged until the closed circuit voltage is 0.5 V or less in order to avoid smoking and ignition. Thereafter, the secondary battery is disassembled to thereby collect a four-layer structure (the positive electrode 13/the separator 15/the negative electrode 14/the separator 15), following which the four-layer structure is separated at an interface between the separator 15 and the negative electrode 14. Thus, a two-layer structure including the positive electrode 13 (the positive electrode 13/the separator 15) is obtained, and a two-layer structure including the negative electrode 14 (the negative electrode 14/the separator 15) is also obtained.

Thereafter, the two-layer structure including the negative electrode 14 is cut into strips, thereby retrieving, as illustrated in FIG. 1, a sample S for measuring the adhesive strength FA. In this case, in the flat part 10F, the two-layer structure is cut in such a manner that the sample S extends in a direction (a direction along the extending direction of the winding axis J, i.e., the Y-axis direction) intersecting with the winding direction of the wound electrode body 10. A width W (mm) of the sample S may be set to any value. In FIG. 1, a retrieving range of the sample S, i.e., a cut portion of the two-layer structure including the negative electrode 14, is denoted by a dashed line, and the retrieving range of the sample S is shaded.

A reason for using the flat part 10F to retrieve the sample S is that the original adhesive strength FA is easily measured stably with satisfactory reproducibility. In detail, an internal stress is easily generated in the curved part 10R at the time of applying pressure to the secondary battery, which causes the adhesive strength FA to easily vary due to an influence of the internal stress. In contrast, the internal stress is not generated easily in the flat part 10F at the time of applying pressure to the secondary battery, which makes the adhesive strength FA to be easily maintained without being influenced by the internal stress.

Thereafter, the sample S is fixed to a support plate including metal using a double-stick tape. In this case, the double-stick tape is adhered to the sample S to thereby adhering the sample S to the support plate. Thereafter, the separator 15 is peeled off from the negative electrode 14 by about 5 mm, following which a fixing tape is adhered to the negative electrode 14 in a region where the separator 15 is peeled off.

Lastly, the sample S is set on a tensile tester (Autograph AGS-50B available from Shimadzu Corporation), following which a tensile test force N (mN) is measured while peeling the separator 15 from the negative electrode 14 using the tensile tester (a kind of measurement=peel). In this case, the separator 15 is pulled in a direction of 180° with respect to an extending direction of the sample S, and a tensile rate of the separator 15 is set to 100 mm/min. Further, the tensile test force N is divided by the width W of the sample S to thereby calculate a load (N/W), that is, the adhesive strength FA (mN/mm). In particular, the adhesive strength FA is determined by: excluding a load calculated in a range of 5 mm after a start of pulling (a load immediately after the start of pulling) and a load calculated in a range of 5 mm before an end of pulling (a load immediately before the end of pulling); and calculating an average value of the loads calculated in ranges other than the above-described ranges.

A reason why the load immediately after the start of pulling and the load immediately before the end of pulling are excluded in calculating the adhesive strength FA is that the tensile test force tends to vary greatly in these ranges due to a pulling operation after the start of pulling and a pulling operation before the end of pulling. The adhesive strength FA is calculated by excluding the loads calculated in these ranges, thereby making it possible to calculate the adhesive strength FA stably and with high accuracy.

The secondary battery according to the fifth embodiment operates as follows, for example. Upon charging the secondary battery, lithium ions are extracted from the positive electrode 13, and the extracted lithium ions are inserted into the negative electrode 14 via the electrolytic solution. Upon discharging the secondary battery, lithium ions are extracted from the negative electrode 14, and the extracted lithium ions are inserted into the positive electrode 13 via the electrolytic solution.

In a case of manufacturing the secondary battery according to the fifth embodiment, the positive electrode 13 and the negative electrode 14 are fabricated and thereafter the secondary battery is assembled using the positive electrode 13 and the negative electrode 14, following which the secondary battery is hot-pressed, for example, as described below.

First, the positive electrode active material including the layered rock-salt lithium-cobalt composite oxide is mixed with materials including, without limitation, the positive electrode binder and the positive electrode conductor on an as-needed basis to thereby obtain a positive electrode mixture. Thereafter, the positive electrode mixture is dispersed or dissolved into a solvent such as an organic solvent to thereby prepare a paste positive electrode mixture slurry. Lastly, the positive electrode mixture slurry is applied on both sides of the positive electrode current collector 13A, following which the applied positive electrode mixture slurry is dried to thereby form the positive electrode active material layers 13B. Thereafter, the positive electrode active material layers 13B may be compression-molded by means of a machine such as a roll pressing machine. In this case, the positive electrode active material layers 13B may be heated. The positive electrode active material layers 13B may be compression-molded a plurality of times.

The negative electrode active material layers 14B are provided on both sides of the negative electrode current collector 14A by a procedure similar to the fabrication procedure of the positive electrode 13 described above. Specifically, the negative electrode active material including graphite is mixed with materials including, without limitation, the negative electrode binder and the negative electrode conductor on an as-needed basis to thereby obtain a negative electrode mixture. Thereafter, the negative electrode mixture is dispersed or dissolved into a solvent such as an organic solvent or an aqueous solvent to thereby prepare a paste negative electrode mixture slurry. Thereafter, the negative electrode mixture slurry is applied on both sides of the negative electrode current collector 14A, following which the applied negative electrode mixture slurry is dried to thereby form the negative electrode active material layers 14B. Thereafter, the negative electrode active material layers 14B may be compression-molded.

In the case of fabricating the positive electrode 13 and the negative electrode 14, a mixture ratio between the positive electrode active material and the negative electrode active material (a relationship between mass of the positive electrode active material and mass of the negative electrode active material) is adjusted in such a manner that the mass of the positive electrode active material is sufficiently greater, to thereby satisfy the above-described two configuration conditions (the negative electrode potential Ef and the negative electrode potential variation Ev).

A compound such as a polymer compound is added to a solvent such as an organic solvent, and thereafter the solvent is stirred to thereby prepare a precursor solution. In this case, the insulating particles may be added to the solvent on an as-needed basis. Thereafter, the precursor solution is applied to one side of the base layer 15A, following which the precursor solution is dried to thereby form the polymer compound layer 15B (the positive electrode-side polymer compound layer 15BX). Further, the precursor solution is applied to the other side of the base layer 15A, following which the precursor solution is dried to thereby form the polymer compound layer 15B (the negative electrode-side polymer compound layer 15BY).

First, the positive electrode lead 11 is coupled to the positive electrode 13 (the positive electrode current collector 13A) by a method such as a welding method, and the negative electrode lead 12 is coupled to the negative electrode 14 (the negative electrode current collector 14A) by a method such as a welding method. Thereafter, the positive electrode 13 and the negative electrode 14 are stacked on each other with the separator 15 interposed therebetween, following which the positive electrode 13, the negative electrode 14, and the separator 15 are wound to thereby form a wound body. In this case, an unillustrated jig having an elongated shape is used to wind the positive electrode 13, the negative electrode 14, and the separator 15 about the winding axis J to thereby cause the wound body to be in the elongated shape as illustrated in FIG. 1.

Thereafter, the outer package member 20 is folded in such a manner as to sandwich the wound electrode body 10, following which the outer edges excluding one side of the outer package member 20 are bonded to each other by a method such as a thermal fusion bonding method. Thus, the wound body is contained in the pouch-shaped outer package member 20. Thereafter, the electrolytic solution is injected into the pouch-shaped outer package member 20, following which the outer package member 20 is sealed by a method such as a thermal fusion bonding method. In this case, the sealing film 31 is interposed between the outer package member 20 and the positive electrode lead 11, and the sealing film 32 is interposed between the outer package member 20 and the negative electrode lead 12. The wound body is thereby impregnated with the electrolytic solution, forming the wound electrode body 10. Accordingly, the wound electrode body 10 is contained in the outer package member 20. Thus, the secondary battery is assembled.

After having been assembled, the secondary battery is applied with pressure and heated using a machine such as a hot press machine in a direction (the Z-axis direction) intersecting the winding axis J while charging (i.e., performing initial-cycle charging of) the secondary battery. A charging condition is not particularly limited as long as it is a condition where the closed circuit voltage is 2.5 V or higher. This initial-cycle charging forms a film such as an SEI (Solid Electrolyte Interphase) film on a surface of the negative electrode 14. A temperature at the time of heating is not particularly limited, and is, for example, 25° C. to 105° C. both inclusive. Pressure at the time of pressure application is not particularly limited, and is, for example, from 3 kgf/cm$^2$ to 30 kgf/cm$^2$ both inclusive. As a result, the positive electrode 13 is closely attached to the separator 15 and the negative electrode 14 is closely attached to the separator 15, thereby completing the secondary battery.

In this hot pressing, the above-described conditions such as the temperature and the pressure are adjusted to thereby satisfy the above-described configuration condition (the adhesive strength FA). Similarly, in the hot pressing, for example, the above-described configuration condition (the adhesive strength FC), for example, is satisfied.

According to the secondary battery of the fifth embodiment, in a case where the positive electrode 13 includes the positive electrode active material (the layered rock-salt lithium-cobalt composite oxide), where the negative electrode 14 includes the negative electrode active material (graphite), and where the separator 15 is adhered to the negative electrode active material layer 14B: the above-described three configuration conditions (the negative electrode potential Ef, the negative electrode potential variation Ev, and the adhesive strength FA) may be satisfied. In this case, as compared with the case where the three configuration conditions are not satisfied, even if the charge voltage Ec is increased to 4.38 V or higher: the potential E of the positive electrode 13 is prevented from easily reaching the potential constant region P2 associated with the phase transition, or the potential E of the positive electrode 13 is prevented from easily passing through the potential constant region P2 associated with the phase transition; the precipitation of lithium metal is suppressed on the negative electrode 14; and the negative electrode 14 is prevented from easily being peeled off from the separator 15. As a result, not only the capacity loss and the gas generation are suppressed, but also the decrease in battery capacity is suppressed. In addition, it becomes easier for the charging and discharging reactions to proceed stably and the decomposition of the electrolytic solution is suppressed upon charging and discharging. This further suppresses the capacity loss and the gas generation, and further suppresses the decrease in battery capacity. Accordingly, it is possible to achieve superior battery characteristics.

In particular, the separator 15 may include the polymer compound layer 15B (the negative electrode-side polymer compound layer 15BY) together with the base layer 15A. This makes it easier for the negative electrode active material layer 14B to be closely attached to the separator 15, making it possible to achieve higher effects accordingly. In this case, the negative electrode-side polymer compound layer 15BY may include the insulating particles. This improves safety, making it possible to achieve further higher effects accordingly.

In addition, the adhesive strength FC may satisfy the above-described configuration condition, in other words, the above-described four configuration conditions (the negative electrode potential Ef, the negative electrode potential variation Ev, and the adhesive strengths FC and FA) may be satisfied. This prevents the positive electrode 13 from being easily peeled off from the separator 15 even if the charge voltage Ec is increased to 4.38 V or higher, which makes it possible to achieve higher effects accordingly. In this case, the separator 15 may include the polymer compound layer 15B (the positive electrode-side polymer compound layer 15BX) together with the base layer 15A. This makes it easier for the positive electrode active material layer 13B to be closely attached to the separator 15, making it possible to achieve further higher effects accordingly. Further, the positive electrode active material layer 13B (the positive electrode binder) and the positive electrode-side polymer compound layer 15BX may each include the fluorine-based polymer compound. This makes it further easier for the positive electrode active material layer 13B to be closely attached to the separator 15, making it possible to achieve further higher effects accordingly. Still further, the positive electrode-side polymer compound layer 15BX may include the insulating particles. This improves safety, making it possible to achieve further higher effects accordingly.

A description is given next of a secondary battery according to a sixth embodiment of the technology. The secondary battery according to the sixth embodiment has a configuration that is substantially similar to the configuration of the secondary battery according to the first embodiment described above, except for the points described below.

An electrolytic solution included in the secondary battery according to the sixth embodiment includes a solvent and an electrolyte salt. Only one solvent may be used, or two or more solvents may be used. Only one electrolyte salt may be used, or two or more electrolyte salts may be used.

The solvent includes one or more of solvents including, without limitation, non-aqueous solvents (organic solvents). An electrolytic solution including the non-aqueous solvent is a so-called non-aqueous electrolytic solution. Specifically, the solvent includes: a carbonate ester, a lactone, or both; and a chain carboxylate ester. The carbonate ester may be, for example, a cyclic carbonate ester, a chain carbonate ester, or both. The chain carboxylate ester may have a chain structure or a branched structure having one or more side chains. Only one carbonate ester may be used, or two or more carbonate esters may be used. Similarly, only one lactone may be used, or two or more lactones may be used. Only one chain carboxylate ester may be used, or two or more chain carboxylate esters may be used.

The cyclic carbonate ester is not limited to a particular kind, and examples thereof include ethylene carbonate and propylene carbonate. The chain carbonate ester is not limited to a particular kind, and examples thereof include dimethyl carbonate and diethyl carbonate. The lactone is not limited to a particular kind, and examples thereof include γ-butyrolactone and γ-valerolactone.

The chain carboxylate ester is not limited to a particular kind, and preferably includes, for example, one or more of an acetate ester, a propionate ester, and a butyrate ester. In this case, a molecular weight of the chain carboxylate ester is not particularly limited, and is preferably 119 or less in particular. A reason for this is that a viscosity of the electrolytic solution does not increase excessively, suppressing inhibition of movement of lithium ions. This improves ionic conductivity of the lithium ions. Specific examples of the chain carboxylate ester include methyl acetate, ethyl acetate, propyl acetate, butyl acetate, methyl propionate, ethyl propionate, propyl propionate, methyl butyrate, 2-methyl ethyl propionate, 2-methyl methyl propionate, and 2,2-dimethyl propionate.

A reason why the solvent includes the chain carboxylate ester together with the carbonate ester and the lactone is that the chain carboxylate ester has a low viscosity, making it easier for the lithium ions to move in the electrolytic solution. This suppresses the precipitation of lithium metal on the negative electrode 14 upon charging and discharging, and in particular, suppresses the precipitation of lithium metal even if the charge voltage Ec to be described later is increased. In this case, if the chain carboxylate ester is, for example, methyl acetate described above, it sufficiently makes it easier for the lithium ions to move, which sufficiently suppresses the precipitation of lithium metal.

It should be understood that the solvent may also include one or more of other non-aqueous solvents together with the carbonate ester, the lactone, and the chain carboxylate ester described above.

The other non-aqueous solvent includes, for example, one or more of nitrile (mononitrile) compounds. Examples of the nitrile compound include acetonitrile, methoxy acetonitrile, and 3-methoxy propionitrile. A reason for this is that characteristics including, without limitation, a capacity characteristic, a cyclability characteristic, and a storage characteristic are secured.

In particular, it is preferable that the non-aqueous solvent include one or more of dinitrile compounds. A reason for this is that: an oxidation resistance of the chain carboxylate ester is low, thereby making it easier for the chain carboxylate ester to be decomposed upon charging and discharging; however, the oxidation resistance of the chain carboxylate ester is improved if the electrolytic solution includes the dinitrile compound, thereby suppressing decomposition of the carboxylate ester upon charging and discharging. In particular, as the chain carboxylate ester tends to be easily decomposed in a high temperature environment, the decomposition of the chain carboxylate ester is sufficiently suppressed even in the high temperature environment if the electrolytic solution includes the dinitrile compound.

The dinitrile compound is not limited to a particular kind, and examples thereof include succinonitrile (NC—$C_2H_4$—

CN), glutaronitrile (NC—$C_3H_6$—CN), adiponitrile (NC-$C_4H_8$—CN), sebaconitrile (NC—$C_8H_{10}$—CN), and phthalonitrile (NC—$C_6H_4$—CN).

A content of the dinitrile compound in the electrolytic solution is not particularly limited; however, in particular, the content is preferably from 1 wt % to 20 wt % both inclusive. A reason for this is that the decomposition of the chain carboxylate ester is sufficiently suppressed while decrease in battery capacity is suppressed.

In particular, the non-aqueous solvent preferably includes a dioxane compound together with the halogenated carbonate ester. The dioxane compound is, for example, one or more of compounds represented by Formula (17) below. Only one halogenated carbonate ester may be used, or two or more halogenated carbonate esters may be used. A reason for this is that a film derived from the halogenated carbonate ester is provided on a surface of the negative electrode 14 upon charging and discharging, thereby protecting the surface of the negative electrode 14 by the film. Thus, even if the precipitation of lithium metal occurs on the negative electrode 14, the lithium metal is prevented from reacting excessively with the electrolytic solution. This improves reversibility of the lithium metal upon charging and discharging, thereby suppressing the precipitation of lithium metal. Another reason for this is that, although the halogenated carbonate ester has a property of easily generating a gas due to a reaction with, for example, the electrolytic solution, the generation of the gas due to the reaction of the halogenated carbonate ester is suppressed by the dioxane compound. As a result, even if gas generation occurs inside the secondary battery, swelling of the secondary battery is suppressed.

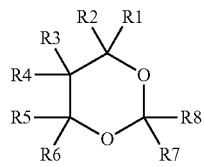

(17)

where each of R1 to R8 is one of a hydrogen group and a monovalent hydrocarbon group.

The term "halogenated carbonate ester" is a generic term for a carbonate ester including one or more halogens as a constituent element or constituent elements. The halogenated carbonate ester may be a cyclic halogenated carbonate ester or a chain halogenated carbonate ester. Examples of the kind of the one or more halogens include fluorine, chlorine, bromine, and iodine.

Specific examples of the cyclic halogenated carbonate ester include 4-fluoro-1,3-dioxolane-2-one and 4,5-difluoro-1,3-dioxolane-2-one. Examples of the chain halogenated carbonate ester include fluoromethyl methyl carbonate, bis (fluoromethyl) carbonate, and difluoromethyl methyl carbonate.

As is apparent from Formula (17), the dioxane compounds are 1,3-dioxane and a derivative thereof. A kind of each of R1 to R8 is not particularly limited as long as each of R1 to R8 is, as described above, one of the hydrogen group and the monovalent hydrocarbon group. The term "monovalent hydrocarbon group" is a generic term for a monovalent group including carbon and hydrogen. The monovalent hydrocarbon group may have: a straight-chain structure; a branched structure having one or more side chains; a cyclic structure having one or more rings; or a bonded structure including two or more thereof that are bonded to each other. The monovalent hydrocarbon group may include one or more carbon-carbon unsaturated bonds, or may include no carbon-carbon unsaturated bond. The carbon-carbon unsaturated bond may be a carbon-carbon double bond, a carbon-carbon triple bond, or both.

Examples of the monovalent hydrocarbon group include an alkyl group, an alkenyl group, an alkynyl group, a cycloalkyl group, an aryl group, and a bonded group. The bonded group is a monovalent group in which two or more of an alkyl group, an alkenyl group, an alkynyl group, a cycloalkyl group, and an aryl group are bonded to each other. The carbon number of the monovalent hydrocarbon group is not particularly limited.

Specific examples of the dioxane compound include 1,3-dioxane, 4-methyl-1,3-dioxane, 4,5-dimethyl-1,3-dioxane, and 4,5,6-trimethyl-1,3-dioxane.

A content of the halogenated carbonate ester in the electrolytic solution is not particularly limited; however, in particular, the content of the halogenated carbonate ester is preferably from 1 wt % to 20 wt % both inclusive. Further, a content of the dioxane compound in the electrolytic solution is not particularly limited; however, in particular, the content of the dioxane compound is preferably from 0.1 wt % to 2 wt % both inclusive. A reason for this is that reaction of lithium metal with the electrolytic solution is sufficiently suppressed while the swelling of the secondary battery is sufficiently suppressed.

In addition thereto, the non-aqueous solvent may include, for example, one or more of an unsaturated cyclic carbonate ester, a sulfonate ester, an acid anhydride, a diisocyanate compound, and a phosphate ester. A reason for this is that characteristics including, without limitation, a battery capacity, a cyclability characteristic, and a storage characteristic are further improved.

Examples of the unsaturated cyclic carbonate ester include vinylene carbonate, vinyl ethylene carbonate, and methylene ethylene carbonate. Examples of the sulfonate ester include 1,3-propane sultone and 1,3-propene sultone. Examples of the acid anhydride include succinic anhydride, glutaric anhydride, maleic anhydride, ethane disulfonic anhydride, propane disulfonic anhydride, sulfobenzoic anhydride, sulfopropionic anhydride, and sulfobutyric anhydride. Examples of the diisocyanate compound include hexamethylene diisocyanate. Examples of the phosphate ester include trimethyl phosphate and triethyl phosphate.

The electrolyte salt includes one or more of lithium salts, for example. The electrolyte salt may further include one or more of light metal salts other than the lithium salt. The lithium salt is not limited to a particular kind, and examples thereof include lithium hexafluorophosphate ($LiPF_6$), lithium tetrafluoroborate ($LiBF_4$), lithium bis(fluorosulfonyl)imide ($LiN(SO_2F)_2$), lithium bis(trifluoromethane sulfonyl)imide ($LiN(CF_3SO_2)_2$), lithium fluorophosphate ($Li_2PFO_3$), lithium difluorophosphate ($LiPF_2O_2$), and lithium bis(oxalato)borate ($LiC_4BO_8$). A reason for this is that characteristics including, without limitation, a capacity characteristic, a cyclability characteristic, and a storage characteristic are secured.

A content of the electrolyte salt is, for example, greater than or equal to 0.3 mol/kg and less than or equal to 3.0 mol/kg with respect to the solvent, but is not particularly limited thereto.

In particular, the electrolytic solution preferably includes the dioxane compound together with a lithium salt including boron as a constituent element (hereinafter, referred to as a "boron-containing lithium salt"). Details of the dioxane compound are as described above. This is because, for a reason similar to that of the case where the non-aqueous solvent includes the dioxane compound together with the halogenated carbonate ester, the precipitation of lithium metal is suppressed upon charging and discharging and the swelling of the secondary battery is also suppressed. Only one boron-containing lithium salt may be used, or two or more boron-containing lithium salts may be used.

The boron-containing lithium salt is not limited to a particular kind, and is a compound represented by each of Formula (18-1) and Formula (18-2) below in addition to lithium tetrafluoride described above.

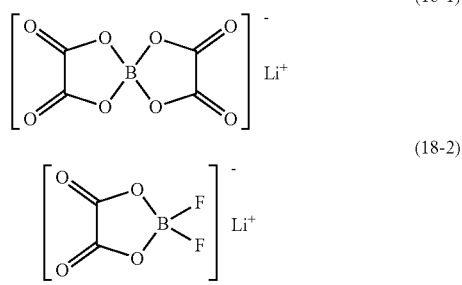

A content of the boron-containing lithium salt in the electrolytic solution is not particularly limited; however, in particular, the content of the boron-containing lithium salt is preferably from 0.1 mol/l to 2 mol/l both inclusive (i.e., from 0.1 mol/dm$^3$ to 2 mol/dm$^3$ both inclusive). Further, a content of the dioxane compound in the electrolytic solution is not particularly limited; however, in particular, the content of the dioxane compound is preferably from 0.1 wt % to 2 wt % both inclusive. A reason for this is that reaction of lithium metal with the electrolytic solution is sufficiently suppressed while the swelling of the secondary battery is sufficiently suppressed.

A charge and discharge principle and configuration conditions of the secondary battery according to the sixth embodiment will now be described.

[Premise and Charge and Discharge Principle]

The premise and the charge and discharge principle related to the secondary battery according to the sixth embodiment are similar to the premise and the charge and discharge principle related to the secondary battery according to the first embodiment described above.

In the secondary battery according to the sixth embodiment, three configuration conditions described below are satisfied in order to achieve the charge and discharge principle described above.

First, a state in which the secondary battery is charged with a constant voltage of a closed circuit voltage (CCV) of 4.38 V or higher for 24 hours is referred to as a full charge state. A potential E (a negative electrode potential Ef) of the negative electrode 14 measured in the secondary battery in the full charge state is from 19 mV to 86 mV both inclusive. It should be understood that a value of a current at the time of charging the secondary battery until the closed circuit voltage reaches 4.38 V or higher is not particularly limited, and may thus be set to any value.

That is, as described above, the potential E of the negative electrode 14 is set to cause the charging not to be completed in the potential constant region P3 and to be completed in the potential varying region P4. Accordingly, when the secondary battery is charged to the full charge state, the negative electrode potential Ef is lower in a case where the charging is completed in the potential varying region P4 than in a case where the charging is completed in the potential constant region P3. Thus, the negative electrode potential Ef becomes lower than about 90 mV, and more specifically, from 19 mV to 86 mV both inclusive, as described above.

Second, a discharge capacity obtained when the secondary battery is discharged with a constant current from the full charge state until a closed circuit voltage reaches 3.00 V, following which the secondary battery is discharged with a constant voltage of the closed circuit voltage of 3.00 V for 24 hours is referred to as a maximum discharge capacity (mAh). In this case, when the secondary battery is discharged from the full charge state by a capacity corresponding to 1% of the maximum discharge capacity, a variation of the potential E of the negative electrode 14, i.e., a negative electrode potential variation Ev, represented by Formula (16) below is 1 mV or greater. As is apparent from Formula (16), the negative electrode potential variation Ev is a difference between a potential E1 (a first negative electrode potential) and a potential E2 (a second negative electrode potential). It should be understood that the current value at the time of discharging the secondary battery from the full charge state until the closed circuit voltage reaches 3.00 V is not particularly limited and may be set to any value as long as the current value is within a general range, because the secondary battery is discharged with a constant voltage for 24 hours.

Negative electrode potential variation $Ev$ (mV)=potential E2 (mV)−potential $E1$ (mV)  (16)

where:
the potential E1 is an open circuit potential (versus a lithium reference electrode) of the negative electrode 14 measured in the secondary battery in the full charge state; and
the potential E2 is an open circuit potential (versus a lithium reference electrode) of the negative electrode 14 measured in the secondary battery that is discharged from the full charge state by the capacity corresponding to 1% of the maximum discharge capacity.

That is, as described above, in a case where the potential E of the negative electrode 14 is set to cause the charging to be completed in the potential varying region P4, the potential E of the negative electrode 14 increases markedly upon discharging the secondary battery in the full charge state by the capacity corresponding to 1% of the maximum discharge capacity, as is apparent from FIGS. 6 and 7. Thus, the potential E (E2) of the negative electrode 14 after the discharging is sufficiently increased as compared with the potential E (E1) of the negative electrode 14 before the discharging (the full charge state). Accordingly, the negative electrode potential variation Ev, which is the difference between the potential E1 and the potential E2, is 1 mV or greater as described above.

Third, regarding a composition of the solvent included in the electrolytic solution, a ratio of a volume of the chain carboxylate ester to a sum of a volume of the carbonate ester, a volume of the lactone, and a volume of the chain carboxylate ester is from 10 vol % to 80 vol % both inclusive. The ratio of the volume (vol %) of the chain carboxylate ester is calculated by a calculation formula: ratio of volume of chain carboxylate ester=[volume of chain carboxylate ester/(volume of carbonate ester+volume of lactone+volume of chain carboxylate ester)]×100.

As described above, when the potential E of the negative electrode 14 decreases at the end of charging, a capacity range actually used becomes sufficiently large with respect to the theoretical capacity of the negative electrode 14; thus, the precipitation of lithium metal tends to occur on the negative electrode 14 at the end of charging. However, in a case where the two configuration conditions (the negative electrode potential Ef and the negative electrode potential variation Ev) described above are satisfied and where the above-described configuration condition related to the ratio of the chain carboxylate ester having a low viscosity is also satisfied, the ratio of the chain carboxylate ester is optimized. As a result, the precipitation of lithium metal is further suppressed on the negative electrode 14 even if the charge voltage Ec is increased to 4.38 V or higher.

The secondary battery according to the sixth embodiment operates as follows, for example. Upon charging the secondary battery, lithium ions are extracted from the positive electrode 13, and the extracted lithium ions are inserted into the negative electrode 14 via the electrolytic solution. Upon discharging the secondary battery, lithium ions are extracted from the negative electrode 14, and the extracted lithium ions are inserted into the positive electrode 13 via the electrolytic solution.

In a case of manufacturing the secondary battery according to the sixth embodiment, the positive electrode 13 and the negative electrode 14 are fabricated and thereafter the secondary battery is assembled using the positive electrode 13 and the negative electrode 14, for example, as described below.

First, the positive electrode active material including the layered rock-salt lithium-cobalt composite oxide is mixed with materials including, without limitation, the positive electrode binder and the positive electrode conductor on an as-needed basis to thereby obtain a positive electrode mixture. Thereafter, the positive electrode mixture is dispersed or dissolved into a solvent such as an organic solvent to thereby prepare a paste positive electrode mixture slurry. Lastly, the positive electrode mixture slurry is applied on both sides of the positive electrode current collector 13A, following which the applied positive electrode mixture slurry is dried to thereby form the positive electrode active material layers 13B. Thereafter, the positive electrode active material layers 13B may be compression-molded by means of a machine such as a roll pressing machine. In this case, the positive electrode active material layers 13B may be heated. The positive electrode active material layers 13B may be compression-molded a plurality of times.

The negative electrode active material layers 14B are provided on both sides of the negative electrode current collector 14A by a procedure similar to the fabrication procedure of the positive electrode 13 described above. Specifically, the negative electrode active material including graphite is mixed with materials including, without limitation, the negative electrode binder and the negative electrode conductor on an as-needed basis to thereby obtain a negative electrode mixture. Thereafter, the negative electrode mixture is dispersed or dissolved into a solvent such as an organic solvent or an aqueous solvent to thereby prepare a paste negative electrode mixture slurry. Thereafter, the negative electrode mixture slurry is applied on both sides of the negative electrode current collector 14A, following which the applied negative electrode mixture slurry is dried to thereby form the negative electrode active material layers 14B. Thereafter, the negative electrode active material layers 14B may be compression-molded.

In the case of fabricating the positive electrode 13 and the negative electrode 14, a mixture ratio between the positive electrode active material and the negative electrode active material (a relationship between mass of the positive electrode active material and mass of the negative electrode active material) is adjusted in such a manner that the mass of the positive electrode active material is sufficiently greater, to thereby satisfy the above-described two configuration conditions (the negative electrode potential Ef and the negative electrode potential variation Ev).

In a case of preparing the electrolytic solution, the electrolyte salt is added to the solvent including: the carbonate ester, the lactone, or both; and the chain carboxylate ester. Thereafter, the solvent is stirred. In this case, the mixture ratio (a volume ratio) between the carbonate ester, the lactone, and the chain carboxylate ester is adjusted to thereby satisfy the above-described configuration condition (the ratio of the chain carboxylate ester).

First, the positive electrode lead 11 is coupled to the positive electrode 13 (the positive electrode current collector 13A) by a method such as a welding method, and the negative electrode lead 12 is coupled to the negative electrode 14 (the negative electrode current collector 14A) by a method such as a welding method. Thereafter, the positive electrode 13 and the negative electrode 14 are stacked on each other with the separator 15 interposed therebetween, following which the positive electrode 13, the negative electrode 14, and the separator 15 are wound to thereby form a wound body. In this case, an unillustrated jig having an elongated shape is used to wind the positive electrode 13, the negative electrode 14, and the separator 15 about the winding axis J to thereby cause the wound body to be in the elongated shape as illustrated in FIG. 1.

Thereafter, the outer package member 20 is folded in such a manner as to sandwich the wound electrode body 10, following which the outer edges excluding one side of the outer package member 20 are bonded to each other by a method such as a thermal fusion bonding method. Thus, the wound body is contained in the pouch-shaped outer package member 20. Lastly, the electrolytic solution is injected into the pouch-shaped outer package member 20, following which the outer package member 20 is sealed by a method such as a thermal fusion bonding method. In this case, the sealing film 31 is interposed between the outer package member 20 and the positive electrode lead 11, and the sealing film 32 is interposed between the outer package member 20 and the negative electrode lead 12. The wound body is thereby impregnated with the electrolytic solution, forming the wound electrode body 10. Accordingly, the wound electrode body 10 is contained in the outer package member 20. Thus, the secondary battery is completed.

According to the secondary battery of the sixth embodiment, in a case where the positive electrode 13 includes the positive electrode active material (the layered rock-salt lithium-cobalt composite oxide), where the negative electrode 14 includes the negative electrode active material (graphite), and where the electrolytic solution includes the solvent (the carbonate ester, the lactone, or both, in addition to the chain carboxylate ester): the above-described three configuration conditions (the negative electrode potential Ef, the negative electrode potential variation Ev, and the ratio of the chain carboxylate ester) may be satisfied. In this case, as compared with the case where the three configuration conditions are not satisfied, even if the charge voltage Ec is increased to 4.38 V or higher: the potential E of the positive electrode 13 is prevented from easily reaching the potential constant region P2 associated with the phase transition, or the potential E of the positive electrode 13 is prevented from easily passing through the potential constant region P2 associated with the phase transition; and the precipitation of lithium metal is suppressed on the negative electrode 14. Accordingly, not only the capacity loss and the gas generation are suppressed, but also the decrease in battery capacity is suppressed, making it possible to achieve superior battery characteristics.

In particular, the chain carboxylate ester may include esters including, without limitation, the acetate ester, and the molecular weight of the chain carboxylate ester may be 119 or less. This prevents the viscosity of the electrolytic solution from increasing excessively, thereby improving the ionic conductivity of the lithium ions, which makes it possible to achieve higher effects accordingly.

Further, the electrolytic solution may include the dinitrile compound, and the content of the dinitrile compound in the electrolytic solution may be from 1 wt % to 20 wt % both inclusive. This sufficiently suppresses decomposition of the chain carboxylate ester while suppressing, for example, decrease in battery capacity, which makes it possible to achieve higher effects accordingly.

Further, the electrolytic solution may include the dioxane compound together with the halogenated carbonate ester, the content of the halogenated carbonate ester in the electrolytic solution may be from 1 wt % to 20 wt % both inclusive, and the content of the dioxane compound in the electrolytic solution may be from 0.1 wt % to 2 wt % both inclusive. This sufficiently suppresses reaction of lithium metal with the electrolytic solution while sufficiently reducing the swelling of the secondary battery, which makes it possible to achieve higher effects accordingly.

Still further, the electrolytic solution may include the dioxane compound together with the boron-containing lithium salt, the content of the boron-containing lithium salt in the electrolytic solution may be from 0.1 $mol/dm^3$ to 2 $mol/dm^3$ both inclusive, and the content of the dioxane compound in the electrolytic solution may be from 0.1 wt % to 2.0 wt % both inclusive. This sufficiently suppresses reaction of lithium metal with the electrolytic solution while sufficiently reducing the swelling of the secondary battery, which makes it possible to achieve higher effects accordingly.

Still further, the median diameter D50 of the graphite particles may be from 3.5 μm to 30 μm both inclusive. This improves acceptability of lithium ions while suppressing the precipitation of lithium metal, which makes it possible to achieve higher effects accordingly.

Moreover, the spacing S of the (002) plane of graphite may be from 0.3355 nm to 0.3370 nm both inclusive. This reduces the decomposition reaction of the electrolytic solution while securing the battery capacity, which makes it possible to achieve higher effects accordingly.

The configurations of the secondary batteries described above are appropriately modifiable as described below. It should be understood that any two or more of the following series of modifications may be combined.

Figure 11:
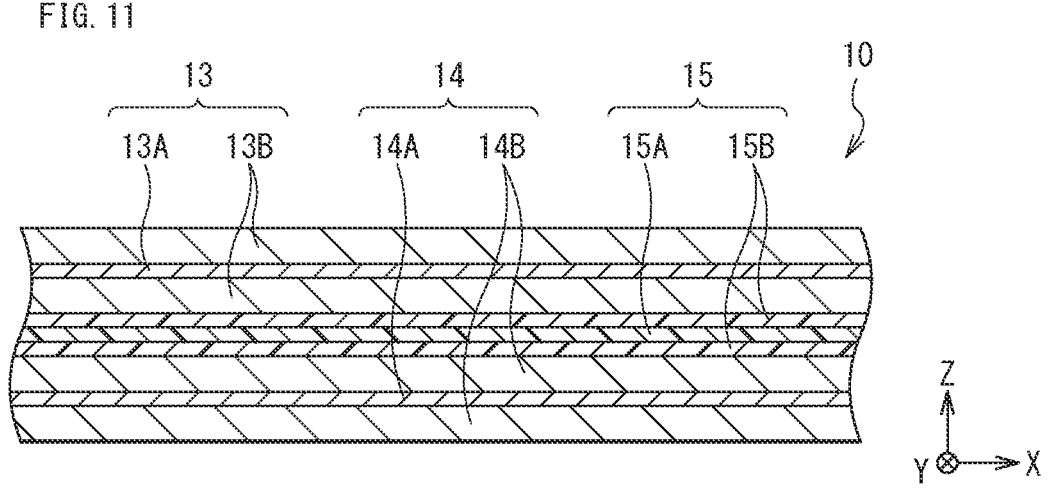
FIG. 11 is a sectional view of a configuration of a secondary battery according to an embodiment of the present technology.

FIG. 11 illustrates a sectional configuration of a secondary battery (the wound electrode body 10) of Modification 1, and corresponds to FIG. 3. As illustrated in FIG. 11, the separator 15 may include, for example, the base layer 15A and the polymer compound layer 15B provided on the base layer 15A. The polymer compound layer 15B may be provided on only one side of the base layer 15A, or on each of both sides of the base layer 15A. FIG. 11 illustrates a case where the polymer compound layer 15B is provided on each of the both sides of the base layer 15A, for example.

The base layer 15A is, for example, the porous film described above. The polymer compound layer 15B includes, for example, a polymer compound such as polyvinylidene difluoride, because such a polymer compound has superior physical strength and is electrochemically stable. It should be understood that the polymer compound layer may include a plurality of insulating particles such as a plurality of inorganic particles. A reason for this is that, at the time of heat generation in the secondary battery, the insulating particles absorb heat, and at the time of damage occurrence (for example, melting) in the separator 15, the insulating particles electrically separate the positive electrode 13 and the negative electrode 14 from each other, thereby improving safety. The insulating particles are not limited to a particular kind, and examples thereof include aluminum oxide and aluminum nitride.

In a case of fabricating the separator 15, for example, a precursor solution that includes materials including, without limitation, the polymer compound and an organic solvent is prepared to thereby apply the precursor solution on each of both sides of the base layer 15A. Thereafter, the precursor solution is dried to thereby form the polymer compound layer 15B.

Also in this case, similar effects are obtainable by satisfying the above-described configuration conditions (the negative electrode potential Ef and the negative electrode potential variation Ev). In particular, adherence of the separator 15 to the positive electrode 13 is improved and adherence of the separator 15 to the negative electrode 14 is improved, suppressing distortion of the wound electrode body 10. This suppresses a decomposition reaction of the electrolytic solution and also suppresses leakage of the electrolytic solution with which the base layer 15A is impregnated, making it possible to achieve higher effects accordingly.

Figure 12:
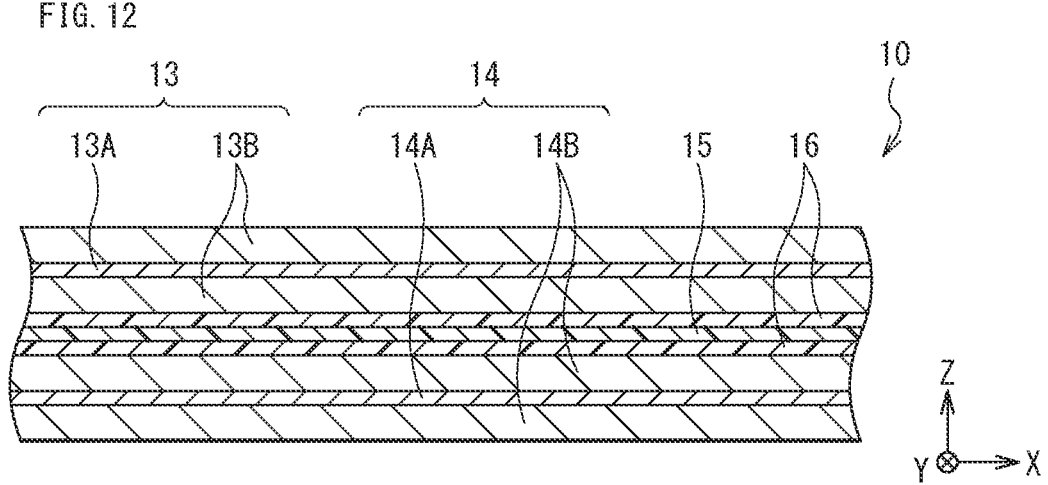
FIG. 12 is a sectional view of a configuration of a secondary battery according to an embodiment of the present technology.

FIG. 12 illustrates a sectional configuration of a secondary battery (the wound electrode body 10) of Modification 2, and corresponds to FIG. 3. As illustrated in FIG. 12, the wound electrode body 10 may include, for example, an electrolyte layer 16 which is a gel electrolyte instead of an electrolytic solution which is a liquid electrolyte.

As illustrated in FIG. 12, in the wound electrode body 10, the positive electrode 13 and the negative electrode 14 are stacked with the separator 15 and the electrolyte layer 16 interposed therebetween, and the positive electrode 13, the negative electrode 14, the separator 15, and the electrolyte layer 16 are wound, for example. The electrolyte layer 16 is interposed, for example, between the positive electrode 13 and the separator 15, and between the negative electrode 14 and the separator 15. However, the electrolyte layer 16 may be interposed only between the positive electrode 13 and the separator 15 or only between the negative electrode 14 and the separator 15.

The electrolyte layer 16 includes a polymer compound together with the electrolytic solution. As described above, the electrolyte layer 16 described here is the gel electrolyte; thus, the electrolytic solution is held by the polymer compound in the electrolyte layer 16. A configuration of the electrolytic solution is as described above. Regarding the electrolyte layer 16 which is the gel electrolyte, the concept of the solvent included in the electrolytic solution is broad and encompasses not only a liquid material but also an ion-conductive material that is able to dissociate the electrolyte salt. Accordingly, the ion-conductive polymer compound is also encompassed by the solvent. The polymer compound includes, for example, a homopolymer, a copolymer, or both. Examples of the homopolymer include polyvinylidene difluoride. Examples of the copolymer include a copolymer of vinylidene fluoride and hexafluoropyrene.

In a case of forming the electrolyte layer 16, for example, a precursor solution that includes materials including, without limitation, the electrolytic solution, the polymer compound, and an organic solvent is prepared to thereby apply the precursor solution on each of the positive electrode 13 and the negative electrode 14, following which the precursor solution is dried.

Also in this case, similar effects are obtainable by satisfying the above-described configuration conditions (the negative electrode potential Ef and the negative electrode potential variation Ev). In particular, this case suppresses leakage of the electrolytic solution, making it possible to achieve higher effects accordingly.

The negative electrode 14 (the negative electrode active material layer 14B) may only include the first negative electrode active material particles (graphite) and does not necessarily include the second negative electrode active material particles (the silicon-containing material). Also in this case, similar effects are obtainable by satisfying the above-described five configuration conditions (the negative electrode potential Ef, the negative electrode potential variation Ev, the median diameter D50A, the volume density, and the integrated intensity ratio).

The above-described configuration condition related to the adhesive strength FA has been satisfied, and the above-described configuration condition related to the adhesive strength FC has also been satisfied.

However, while the configuration condition related to the adhesive strength FA is satisfied, the configuration condition related to the adhesive strength FC is not necessarily satisfied. The adhesive strength FC in this case may be set to any value in a range in which the configuration condition is not satisfied. Also in this case, as compared with a case where neither of the configuration condition related to the adhesive strength FC and the configuration condition related to the adhesive strength FA are satisfied, the negative electrode 14 is prevented from easily peeled off from the separator 15. Thus, similar effects are obtainable.

As long as the configuration condition related to the adhesive strength FA is satisfied, the configuration condition related to the adhesive strength FC is not necessarily satisfied. A reason for this is that, in the secondary battery described here, the lithium ions are inserted into the negative electrode 14 upon charging as described above, making it easier for the negative electrode 14 to swell as compared with the positive electrode 13. Accordingly, as long as the adhesive strength FA is secured, it becomes easier for the charging and discharging reactions to proceed stably and decomposition of the electrolytic solution is suppressed upon charging and discharging. Thus, similar effects are obtainable.

However, in order to sufficiently suppress the decomposition of the electrolytic solution upon charging and discharging, it is preferable that the configuration conditions related to the adhesive strength FC and the adhesive strength FA be both satisfied.

The separator 15 has included two polymer compound layers 15B (the positive electrode-side polymer compound layer 15BX and the negative electrode-side polymer compound layer 15BY). However, in a case where only the configuration condition related to the adhesive strength FA is satisfied or in a case where both the configuration conditions related to the adhesive strengths FC and FA are satisfied, the configuration of the separator 15 may be varied appropriately.

Specifically, the separator 15 may include either one of the positive electrode-side polymer compound layer 15BX and the negative electrode-side polymer compound layer 15BY, or the separator 15 may include neither the positive electrode-side polymer compound layer 15BX nor the negative electrode-side polymer compound layer 15BY. Also in these cases, in the case where only the configuration condition related to the adhesive strength FA is satisfied or in the case where both the configuration conditions related to the adhesive strengths FC and FA are satisfied, similar effects are obtainable. The applications of the secondary battery are not particularly limited as long as they are, for example, machines, apparatuses, instruments, devices, or systems (assembly of a plurality of apparatuses, for example) in which the secondary battery is usable as a driving power source, an electric power storage source for electric power accumulation, or any other source. The secondary battery used as a power source may serve as a main power source or an auxiliary power source. The main power source is preferentially used regardless of the presence of any other power source. The auxiliary power source may be used in place of the main power source, or may be switched from the main power source on an as-needed basis. In a case where the secondary battery is used as the auxiliary power source, the kind of the main power source is not limited to the secondary battery.

Specific examples of the applications of the secondary battery include: electronic apparatuses including portable electronic apparatuses; portable life appliances; storage devices; electric power tools; battery packs mountable on laptop personal computers or other apparatuses as a detachable power source; medical electronic apparatuses; electric vehicles; and electric power storage systems. Examples of the electronic apparatuses include video cameras, digital still cameras, mobile phones, laptop personal computers, cordless phones, headphone stereos, portable radios, portable televisions, and portable information terminals. Examples of the portable life appliances include electric shavers. Examples of the storage devices include backup power sources and memory cards. Examples of the electric power tools include electric drills and electric saws. Examples of the medical electronic apparatuses include pacemakers and hearing aids. Examples of the electric vehicles include electric automobiles including hybrid automobiles. Examples of the electric power storage systems include home battery systems for accumulation of electric power for emergency. Needless to say, the secondary battery may have applications other than those described above.

EXAMPLES

A description is given of Examples of the technology below.

Experiment Examples 1-1 to 1-20

Laminated secondary batteries (lithium-ion secondary batteries) illustrated in FIGS. 1 and 2 were fabricated, following which battery characteristics of the secondary batteries were evaluated as described below.

In a case of fabricating the positive electrode 13, first, 91 parts by mass of the positive electrode active material (lithium cobalt oxide ($LiCoO_2$) serving as the layered rock-salt lithium-cobalt composite oxide), 3 parts by mass of the positive electrode binder (polyvinylidene difluoride), and 6 parts by mass of the positive electrode conductor (graphite) were mixed with each other to thereby obtain a positive electrode mixture. Thereafter, the positive electrode mixture was put into an organic solvent (N-methyl-2-pyrrolidone), following which the organic solvent was stirred to thereby prepare a paste positive electrode mixture slurry. Thereafter, the positive electrode mixture slurry was applied on both sides of the positive electrode current collector 13A (a band-shaped aluminum foil having a thickness of 12 µm) by means of a coating apparatus, following which the applied positive electrode mixture slurry was dried to thereby form the positive electrode active material layers 13B. Lastly, the positive electrode active material layers 13B were compression-molded by means of a roll pressing machine.

In a case of fabricating the negative electrode 14, first, 97 parts by mass of the negative electrode active material (artificial graphite having a median diameter D50 of 10 µm and spacing S of the (002) plane of 0.3360 µm), and 1.5 parts by mass of the negative electrode binder (sodium carboxymethyl cellulose) were mixed with each other to thereby obtain a negative electrode mixture precursor. Thereafter, the negative electrode mixture precursor was put into an aqueous solvent (deionized water), following which 1.5 parts by mass, in terms of solid content, of the negative electrode binder (a styrene-butadiene-rubber dispersion liquid) was put into the aqueous solvent to thereby prepare a paste negative electrode mixture slurry. Thereafter, the negative electrode mixture slurry was applied on both sides of the negative electrode current collector 14A (a band-shaped copper foil having a thickness of 15 µm) by means of a coating apparatus, following which the applied negative electrode mixture slurry was dried to thereby form the negative electrode active material layers 14B. Lastly, the negative electrode active material layers 14B were compression-molded by means of a roll pressing machine.

In the case of fabricating the positive electrode 13 and the negative electrode 14, a mixture ratio (a weight ratio) between the positive electrode active material and the negative electrode active material was adjusted to thereby vary each of the negative electrode potential Ef (mV), the negative electrode potential variation Ev (mV), and the positive electrode potential variation Ew (mV). Each of the negative electrode potential Ef, the negative electrode potential variation Ev, and the positive electrode potential variation Ew in the case where the charge voltage Ec was set to 4.38 V or 4.45 V was as described in Table 1. Here, the maximum discharge capacity was set to 1950 mAh to 2050 mAh both inclusive.

In a case of preparing the electrolytic solution, the electrolyte salt (lithium hexafluorophosphate) was added to a solvent (ethylene carbonate, propylene carbonate, and diethyl carbonate), following which the solvent was stirred. In this case, a mixture ratio (a weight ratio) of ethylene carbonate/propylene carbonate/diethyl carbonate in the solvent was set to 15:15:70, and a content of the electrolyte salt with respect to the solvent was set to 1.2 mol/kg.

In a case of assembling the secondary battery, first, the positive electrode lead 11 including aluminum was welded to the positive electrode current collector 13A, and the negative electrode lead 12 including copper was welded to the negative electrode current collector 14A. Thereafter, the positive electrode 13 and the negative electrode 14 were stacked on each other with the separator 15 (a fine-porous polyethylene film having a thickness of 15 µm) interposed therebetween to thereby obtain a stacked body. Thereafter, the stacked body was wound, following which the protective tape was attached to a surface of the stacked body to thereby obtain a wound body.

Thereafter, the outer package member 20 was folded in such a manner as to sandwich the wound body, following which the outer edges of two sides of the outer package member 20 were thermal fusion bonded to each other. As the outer package member 20, an aluminum laminated film was used in which a surface protective layer (a nylon film having a thickness of 25 µm), a metal layer (an aluminum foil having a thickness of 40 µm), and a fusion-bonding layer (a polypropylene film having a thickness of 30 µm) were stacked in this order. In this case, the sealing film 31 (a polypropylene film having a thickness of 5 µm) was interposed between the outer package member 20 and the positive electrode lead 11, and the sealing film 32 (a polypropylene film having a thickness of 5 µm) was interposed between the outer package member 20 and the negative electrode lead 12.

Lastly, the electrolytic solution was injected into the outer package member 20 and thereafter, the outer edges of one of the remaining sides of the outer package member 20 were thermal fusion bonded to each other in a reduced-pressure environment. Thus, the wound body was impregnated with the electrolytic solution, thereby forming the wound electrode body 10 and sealing the wound electrode body 10 in the outer package member 20. As a result, the laminated secondary battery was completed.

Evaluation of battery characteristics of the secondary batteries revealed the results described in Table 1. A capacity retention characteristic, a high-temperature cyclability characteristic, a high-temperature swelling characteristic, and a low-temperature cyclability characteristic were evaluated here as the battery characteristics.

In a case of examining the capacity retention characteristic, first, the secondary battery was charged and discharged for one cycle in an ambient temperature environment (at a temperature of 23° C.) in order to stabilize a state of the secondary battery. Upon charging, the secondary battery was charged with a constant current of 0.2 C until a battery voltage reached the charge voltage Ec (4.38 V or 4.45 V), and was thereafter charged with a constant voltage of the battery voltage corresponding to the charge voltage Ec until a current reached 0.05 C. Upon discharging, the secondary battery was discharged with a constant current of 0.2 C until a battery voltage reached the discharge voltage Ed (3.00 V). It should be understood that 0.2 C and 0.05 C are values of currents that cause battery capacities (theoretical capacities) to be completely discharged in 5 hours and 20 hours, respectively.

Thereafter, the secondary battery was charged and discharged for another cycle in the same environment and in the above-described charging and discharging conditions to thereby measure a discharge capacity (a discharge capacity before varying the charge voltage Ec). Thereafter, the secondary battery was charged and discharged for another cycle in the same environment and in similar charging and discharging conditions except that the charge voltage Ec was lowered by 10 mV to thereby measure a discharge capacity (a discharge capacity after varying the charge voltage Ec). Lastly, the following was calculated: capacity variation rate (%)=[(discharge capacity before varying charge voltage Ec−discharge capacity after varying charge voltage Ec)/discharge capacity before varying charge voltage Ec]×100.

In a case of examining the high-temperature cyclability characteristic, the state of the secondary battery was stabilized by the above procedures, following which the secondary battery was charged and discharged for one cycle in an ambient temperature environment (at a temperature of 23° C.) to thereby measure a second-cycle discharge capacity. Thereafter, the secondary battery was charged and discharged for another 700 cycles in a high temperature environment (at a temperature of 45° C.) to thereby measure a 702nd-cycle discharge capacity. Lastly, the following was calculated: high-temperature retention rate (%)=(702nd-cycle discharge capacity/second-cycle discharge capacity)×100. Charging and discharging conditions were similar to those for the case of examining the capacity retention characteristic, except that the current at the time of charging was changed to 0.7 C and that the current at the time of discharging was changed to 1 C. It should be understood that 0.7 C and 1 C are values of currents that cause battery capacities (theoretical capacities) to be completely discharged in 10/7 hours and 1 hour, respectively.

In a case of examining the high-temperature swelling characteristic, in the above-described procedures of examining the high-temperature cyclability characteristic, a thickness (a second-cycle thickness) of the secondary battery was measured at the time of measuring the second-cycle discharge capacity, and a thickness (a 702nd-cycle thickness) of the secondary battery was measured at the time of measuring the 702nd-cycle discharge capacity. Thus, the following was calculated: swelling increase rate (%)=[(702nd-cycle thickness−second-cycle thickness)/second-cycle thickness]×100.

In a case of examining the low-temperature cyclability characteristic, the state of the secondary battery was stabilized by the above procedures, following which the secondary battery was charged and discharged for one cycle in an ambient temperature environment (at a temperature of 23° C.) to thereby measure the second-cycle discharge capacity. Thereafter, the secondary battery was charged and discharged for another 100 cycles in a low temperature environment (at a temperature of 0° C.) to thereby measure a 102nd-cycle discharge capacity. Lastly, the following was calculated: low-temperature retention rate (%)=(102nd-cycle discharge capacity/second-cycle discharge capacity)×100. Charging and discharging conditions were similar to those for the case of examining the capacity retention characteristic, except that the current at the time of charging was changed to 0.5 C and that the current at the time of discharging was changed to 0.5 C. It should be understood that 0.5 C is a value of current that causes a battery capacity (a theoretical capacity) to be completely discharged in 2 hours.

TABLE 1

Positive electrode active material: LiCoO$_2$, Negative electrode active material: artificial graphite

| Experiment example | Charge voltage Ec (V) | Negative electrode potential Ef (mV) | Negative electrode potential variation Ev (mV) | Positive electrode potential variation Ew (mV) | Capacity variation rate (%) | High-temperature retention rate (%) | Swelling increase rate (%) | Low-temperature retention rate (%) |
|---|---|---|---|---|---|---|---|---|
| 1-1  | 4.38 | 86 | 1  | 9  | 0.8 | 83 | 12 | 72 |
| 1-2  |      | 80 | 3  | 10 | 0.5 | 86 | 9  | 73 |
| 1-3  |      | 68 | 9  | 11 | 0.5 | 90 | 8  | 73 |
| 1-4  |      | 50 | 17 | 14 | 0.5 | 89 | 8  | 74 |
| 1-5  |      | 19 | 28 | 18 | 0.5 | 89 | 8  | 72 |
| 1-6  | 4.45 | 86 | 1  | <1 | 0.7 | 70 | 14 | 71 |
| 1-7  |      | 80 | 3  | <1 | 0.5 | 72 | 12 | 72 |
| 1-8  |      | 66 | 10 | <1 | 0.5 | 75 | 10 | 72 |
| 1-9  |      | 34 | 23 | 2  | 0.5 | 84 | 10 | 72 |
| 1-10 |      | 19 | 28 | 8  | 0.5 | 83 | 11 | 71 |
| 1-11 | 4.38 | 12 | 15 | 15 | 0.7 | 83 | 8  | 45 |
| 1-12 |      | 87 | <1 | 9  | 1.3 | 78 | 15 | 72 |
| 1-13 |      | 88 | <1 | 9  | 1.4 | 73 | 22 | 70 |
| 1-14 |      | 90 | <1 | 8  | 1.5 | 64 | 35 | 67 |
| 1-15 |      | 91 | <1 | 8  | 1.9 | 60 | 42 | 59 |
| 1-16 | 4.45 | 14 | 18 | 8  | 0.7 | 82 | 12 | 35 |
| 1-17 |      | 87 | <1 | <1 | 1.1 | 75 | 14 | 73 |
| 1-18 |      | 89 | <1 | <1 | 1.5 | 72 | 25 | 73 |
| 1-19 |      | 90 | <1 | <1 | 1.6 | 51 | 45 | 62 |
| 1-20 |      | 92 | <1 | <1 | 1.9 | 47 | 55 | 56 |

As described in Table 1, in the case where the positive electrode 13 included the positive electrode active material (the layered rock-salt lithium-cobalt composite oxide) and the negative electrode 14 included the negative electrode active material (graphite), and where the charge voltage Ec was set to higher than or equal to 4.38 V, each of the capacity variation rate, the high-temperature retention rate, the swelling increase rate, and the low-temperature retention rate varied depending on the negative electrode potential Ef and the negative electrode potential variation Ev.

Specifically, in a case where two configuration conditions, i.e., the negative electrode potential Ef being from 19 mV to 86 mV both inclusive and the negative electrode potential variation Ev being greater than or equal to 1 mV, were satisfied together (Experiment examples 1-1 to 1-10), the capacity variation rate and the swelling increase rate each decreased sufficiently and the high-temperature retention rate and the low-temperature retention rate each increased sufficiently, as compared with a case where the two configuration conditions were not satisfied together (Experiment examples 1-11 to 1-20). More specifically, in the case where the two configuration conditions were satisfied, the capacity variation rate of less than 1%, the high-temperature retention rate of 70% or more, the swelling increase rate of an order of 10% at a maximum, and the low-temperature retention rate of 70% or more were obtained.

Further, in the case where the two configuration conditions were satisfied, the high-temperature retention rate was further increased if the positive electrode potential variation Ew was 2 mV or more.

Experiment Examples 2-1 to 2-6

As described in Table 2, secondary batteries were fabricated following which the battery characteristics of the secondary batteries were examined by similar procedures except that the configuration of the negative electrode 14 (the median diameter D50 (μm) of the negative electrode active material (the artificial graphite)) was changed.

TABLE 2

Positive electrode active material: $LiCoO_2$,
Negative electrode active material:
artificial graphite, Charge voltage Ec = 4.38 V,
Negative electrode potential Ef = 50 mV,
Negative electrode potential variation Ev = 17 mV,
Positive electrode potential variation Ew = 14 mV

| Experiment example | D50 (μm) | Capacity variation rate (%) | High-temperature retention rate (%) | Swelling increase rate (%) | Low-temperature retention rate (%) |
|---|---|---|---|---|---|
| 2-1 | 2 | 0.6 | 45 | 25 | 67 |
| 2-2 | 3.5 | 0.6 | 72 | 14 | 80 |
| 2-3 | 5 | 0.5 | 80 | 11 | 78 |
| 1-4 | 10 | 0.5 | 89 | 8 | 74 |
| 2-4 | 20 | 0.5 | 85 | 9 | 70 |
| 2-5 | 30 | 0.5 | 82 | 12 | 55 |
| 2-6 | 50 | 0.5 | 71 | 15 | 35 |

In a case where the median diameter D50 was within an appropriate range (from 3.5 μm to 30 μm both inclusive) (Experiment examples 1~4 and 2-2 to 2-5), a high high-temperature retention rate and a high low-temperature retention rate were obtained, as compared with a case where the median diameter D50 was outside the appropriate range (Experiment examples 2-1 to 2-6). In particular, in a case where the median diameter D50 was within a range of 5 μm to 20 μm both inclusive (Experiment examples 1-4, 2-3, and 2-4), a further higher high-temperature retention rate was obtained and a further higher low-temperature retention rate was also obtained.

Experiment Examples 3-1 to 3-5

As described in Table 3, secondary batteries were fabricated following which the battery characteristics of the secondary batteries were examined by similar procedures except that the configuration of the negative electrode 14 (the spacing S (nm) of the (002) plane of the negative electrode active material (the artificial graphite)) was changed.

TABLE 3

Positive electrode active material: $LiCoO_2$,
Negative electrode active material:
artificial graphite, Charge voltage Ec = 4.38 V,
Negative electrode potential Ef = 50 mV,
Negative electrode potential variation Ev = 17 mV,
Positive electrode potential variation Ew = 14 mV

| Experiment example | Spacing S (nm) | Capacity variation rate (%) | High-temperature retention rate (%) | Swelling increase rate (%) | Low-temperature retention rate (%) |
|---|---|---|---|---|---|
| 3-1 | 0.3355 | 0.5 | 72 | 15 | 64 |
| 3-2 | 0.3356 | 0.5 | 75 | 13 | 70 |
| 1-4 | 0.3360 | 0.5 | 89 | 8 | 74 |
| 3-3 | 0.3363 | 0.5 | 88 | 9 | 80 |
| 3-4 | 0.3370 | 0.5 | 84 | 10 | 82 |
| 3-5 | 0.3375 | 0.5 | 81 | 13 | 84 |

In a case where the spacing S was within an appropriate range (from 0.3355 nm to 0.3370 nm both inclusive) (Experiment examples 1-4 and 3-1 to 3-4), a high high-temperature retention rate and a high low-temperature retention rate were obtained, as compared with a case where the spacing S was outside the appropriate range (Experiment example 3-5). In particular, in a case where the spacing S was within the range of 0.3356 nm to 0.3363 nm both inclusive (Experiment examples 1-4, 3-2, and 3-3), a further higher high-temperature retention rate was obtained and a further higher low-temperature retention rate was also obtained.

Based upon the results described in Tables 1 to 3, in the case where the positive electrode 13 included the positive electrode active material (the layered rock-salt lithium-cobalt composite oxide) and the negative electrode 14 included the negative electrode active material (the graphite), and where the above-described two configuration conditions (the negative electrode potential Ef and the negative electrode potential variation Ev) were satisfied: the capacity retention characteristic, the high-temperature cyclability characteristic, the high-temperature swelling characteristic, and the low-temperature cyclability characteristic were each improved. Accordingly, superior battery characteristics of the secondary batteries were obtained.

Experiment Examples 4-1 to 4-20

Next, laminated secondary batteries (lithium-ion secondary batteries) illustrated in FIGS. 1 and 2 were fabricated, following which battery characteristics of the secondary batteries were evaluated as described below.

In a case of fabricating the positive electrode 13, first, 96 parts by mass of the positive electrode active material (lithium cobalt oxide ($LiCoO_2$) serving as the layered rock-salt lithium-cobalt composite oxide), 1 part by mass of the positive electrode binder (polyvinylidene difluoride serving as the vinylidene fluoride-based polymer compound), and 3 parts by mass of the positive electrode conductor (graphite) were mixed with each other to thereby obtain a positive electrode mixture (with a content rate of 1.0 wt %). Thereafter, the positive electrode mixture was put into an organic solvent (N-methyl-2-pyrrolidone), following which the organic solvent was stirred to thereby prepare a paste positive electrode mixture slurry. Thereafter, the positive electrode mixture slurry was applied on both sides of the positive electrode current collector 13A (a band-shaped aluminum foil having a thickness of 12 μm) by means of a coating apparatus, following which the applied positive electrode mixture slurry was dried to thereby form the positive electrode active material layers 13B. Lastly, the positive electrode active material layers 13B were compression-molded by means of a roll pressing machine (with an area density of 40 mg/cm² and a volume density of 4.10 g/cm³).

In a case of fabricating the negative electrode 14, first, 97 parts by mass of the negative electrode active material (artificial graphite having a median diameter D50 of 10 μm and spacing S of the (002) plane of 0.3360 μm), and 1.5 parts by mass of the negative electrode binder (sodium carboxymethyl cellulose) were mixed with each other to thereby obtain a negative electrode mixture precursor. Thereafter, the negative electrode mixture precursor was put into an aqueous solvent (deionized water), following which 1.5 parts by mass, in terms of solid content, of the negative electrode binder (a styrene-butadiene-rubber dispersion liquid) was put into the aqueous solvent to thereby prepare a paste negative electrode mixture slurry. Thereafter, the negative electrode mixture slurry was applied on both sides of the negative electrode current collector 14A (a band-shaped copper foil having a thickness of 15 μm) by means of a coating apparatus, following which the applied negative electrode mixture slurry was dried to thereby form the negative electrode active material layers 14B. Lastly, the negative electrode active material layers 14B were compression-molded by means of a roll pressing machine.

In the case of fabricating the positive electrode 13 and the negative electrode 14, a mixture ratio (a weight ratio) between the positive electrode active material and the negative electrode active material was adjusted to thereby vary each of the negative electrode potential Ef (mV) and the negative electrode potential variation Ev (mV). Each of the negative electrode potential Ef and the negative electrode potential variation Ev in the case where the charge voltage Ec was set to 4.38 V or 4.45 V was as described in Table 4. Here, the maximum discharge capacity was set to 1950 mAh to 2050 mAh both inclusive.

In a case of preparing the electrolytic solution, the electrolyte salt (lithium hexafluorophosphate (LiPF$_6$)) was added to a solvent (ethylene carbonate (EC) and propylene carbonate (PC) each serving as the cyclic carbonate ester, diethyl carbonate (DEC) serving as the chain carbonate ester, and propyl propionate (PP) serving as the chain carboxylate ester), following which the solvent was stirred. In this case, a mixture ratio (a weight ratio) of ethylene carbonate/propylene carbonate/diethyl carbonate/propyl propionate in the solvent was set to 5:4:51:40 (with a solvent ratio of 0.1). A content of the electrolyte salt with respect to the solvent was set to 1.2 mol/kg.

In a case of assembling the secondary battery, first, the positive electrode lead 11 including aluminum was welded to the positive electrode current collector 13A, and the negative electrode lead 12 including copper was welded to the negative electrode current collector 14A. Thereafter, the positive electrode 13 and the negative electrode 14 were stacked on each other with the separator 15 (a fine-porous polyethylene film having a thickness of 15 μm) interposed therebetween to thereby obtain a stacked body. Thereafter, the stacked body was wound, following which the protective tape was attached to a surface of the stacked body to thereby obtain a wound body.

Thereafter, the outer package member 20 was folded in such a manner as to sandwich the wound body, following which the outer edges of two sides of the outer package member 20 were thermal fusion bonded to each other. As the outer package member 20, an aluminum laminated film was used in which a surface protective layer (a nylon film having a thickness of 25 μm), a metal layer (an aluminum foil having a thickness of 40 μm), and a fusion-bonding layer (a polypropylene film having a thickness of 30 μm) were stacked in this order. In this case, the sealing film 31 (a polypropylene film having a thickness of 5 μm) was interposed between the outer package member 20 and the positive electrode lead 11, and the sealing film 32 (a polypropylene film having a thickness of 5 μm) was interposed between the outer package member 20 and the negative electrode lead 12.

Lastly, the electrolytic solution was injected into the outer package member 20 and thereafter, the outer edges of one of the remaining sides of the outer package member 20 were thermal fusion bonded to each other in a reduced-pressure environment. Thus, the wound body was impregnated with the electrolytic solution, thereby forming the wound electrode body 10 and sealing the wound electrode body 10 in the outer package member 20. As a result, the laminated secondary battery was completed.

Evaluation of battery characteristics of the secondary batteries revealed the results described in Table 4. A capacity retention characteristic, a high-temperature cyclability characteristic, a high-temperature swelling characteristic, and a low-temperature cyclability characteristic were evaluated here as the battery characteristics.

In a case of examining the capacity retention characteristic, first, the secondary battery was charged and discharged for one cycle in an ambient temperature environment (at a temperature of 23° C.) in order to stabilize a state of the secondary battery. Upon charging, the secondary battery was charged with a constant current of 0.2 C until a battery voltage reached the charge voltage Ec (4.38 V or 4.45 V), and was thereafter charged with a constant voltage of the battery voltage corresponding to the charge voltage Ec until a current reached 0.05 C. Upon discharging, the secondary battery was discharged with a constant current of 0.2 C until a battery voltage reached the discharge voltage Ed (3.00 V). It should be understood that 0.2 C and 0.05 C are values of currents that cause battery capacities (theoretical capacities) to be completely discharged in 5 hours and 20 hours, respectively.

Thereafter, the secondary battery was charged and discharged for another cycle in the same environment and in the above-described charging and discharging conditions to thereby measure a discharge capacity (a discharge capacity before varying the charge voltage Ec). Thereafter, the secondary battery was charged and discharged for another cycle in the same environment and in similar charging and discharging conditions except that the charge voltage Ec was lowered by 10 mV to thereby measure a discharge capacity (a discharge capacity after varying the charge voltage Ec). Lastly, the following was calculated: capacity variation rate (%)=[(discharge capacity before varying charge voltage Ec−discharge capacity after varying charge voltage Ec)/discharge capacity before varying charge voltage Ec]×100.

In a case of examining the high-temperature cyclability characteristic, the state of the secondary battery was stabilized by the above procedures, following which the secondary battery was charged and discharged for one cycle in an ambient temperature environment (at a temperature of 23° C.) to thereby measure a second-cycle discharge capacity. Thereafter, the secondary battery was charged and discharged for another 700 cycles in a high temperature environment (at a temperature of 45° C.) to thereby measure a 702nd-cycle discharge capacity. Lastly, the following was calculated: high-temperature retention rate (%)=(702nd-cycle discharge capacity/second-cycle discharge capacity)×100. Charging and discharging conditions were similar to those for the case of examining the capacity retention characteristic, except that the current at the time of charging was changed to 0.7 C and that the current at the time of discharging was changed to 1 C. It should be understood that 0.7 C and 1 C are values of currents that cause battery capacities (theoretical capacities) to be completely discharged in 10/7 hours and 1 hour, respectively.

In a case of examining the high-temperature swelling characteristic, in the above-described procedures of examining the high-temperature cyclability characteristic, a thickness (a second-cycle thickness) of the secondary battery was measured at the time of measuring the second-cycle discharge capacity, and a thickness (a 702nd-cycle thickness) of the secondary battery was measured at the time of measuring the 702nd-cyle discharge capacity. Thus, the following was calculated: swelling increase rate (%)=[(702nd-cycle thickness−second-cycle thickness)/second-cycle thickness]×100.

In a case of examining the low-temperature cyclability characteristic, the state of the secondary battery was stabilized by the above procedures, following which the secondary battery was charged and discharged for one cycle in an ambient temperature environment (at a temperature of 23° C.) to thereby measure the second-cycle discharge capacity. Thereafter, the secondary battery was charged and discharged for another 100 cycles in a low temperature environment (at a temperature of 0° C.) to thereby measure a 102nd-cycle discharge capacity. Lastly, the following was calculated: low-temperature retention rate (%)=(102nd-cycle discharge capacity/second-cycle discharge capacity)×100. Charging and discharging conditions were similar to those for the case of examining the capacity retention characteristic, except that the current at the time of charging was changed to 0.5 C and that the current at the time of discharging was changed to 0.5 C.

variation rate, the high-temperature retention rate, the swelling increase rate, and the low-temperature retention rate varied depending on the negative electrode potential Ef and the negative electrode potential variation Ev.

Specifically, in a case where two configuration conditions, i.e., the negative electrode potential Ef being from 19 mV to 86 mV both inclusive and the negative electrode potential variation Ev being greater than or equal to 1 mV, were satisfied together (Experiment examples 4-1 to 4-10), the capacity variation rate and the swelling increase rate each decreased and the high-temperature retention rate and the low-temperature retention rate each increased slightly, as compared with a case where the two configuration conditions were not satisfied together (Experiment examples 4-11 to 4-20).

Experiment Examples 5-1 to 5-131

As described in Tables 5 to 10, secondary batteries were fabricated following which the battery characteristics of the secondary batteries were examined by similar procedures except that the configuration of the positive electrode 13 (the area density (mg/cm$^2$), the volume density (g/cm$^3$), and the content rate (wt %)) and the composition of the electrolytic solution (the solvent ratio and the content (mol/kg)) were changed, and that a durability characteristic was newly examined together with the high-temperature cyclability characteristic described above.

As described in Tables 5 to 10, in a case of fabricating the positive electrode 13, a condition at the time of compression molding was changed to thereby vary each of the area density and the volume density, and an addition amount of the positive electrode binder was changed to thereby vary

TABLE 4

Positive electrode active material: LiCoO$_2$, Negative electrode active material: artificial graphite

| Experiment example | Charge voltage Ec (V) | Negative electrode potential Ef (mV) | Negative electrode potential variation Ev (mV) | Capacity variation rate (%) | High-temperature retention rate (%) | Swelling increase rate (%) | Low-temperature retention rate (%) |
|---|---|---|---|---|---|---|---|
| 4-1 | 4.38 | 86 | 1 | 0.8 | 83 | 12 | 72 |
| 4-2 | | 80 | 3 | 0.5 | 86 | 9 | 73 |
| 4-3 | | 68 | 9 | 0.5 | 90 | 8 | 73 |
| 4-4 | | 50 | 17 | 0.5 | 89 | 8 | 74 |
| 4-5 | | 19 | 28 | 0.5 | 89 | 8 | 72 |
| 4-6 | 4.45 | 86 | 1 | 0.7 | 81 | 14 | 71 |
| 4-7 | | 80 | 3 | 0.5 | 82 | 12 | 72 |
| 4-8 | | 66 | 10 | 0.5 | 86 | 10 | 72 |
| 4-9 | | 34 | 23 | 0.5 | 84 | 10 | 81 |
| 4-10 | | 19 | 28 | 0.5 | 83 | 11 | 80 |
| 4-11 | 4.38 | 12 | 15 | 0.7 | 83 | 8 | 45 |
| 4-12 | | 87 | <1 | 1.3 | 78 | 15 | 72 |
| 4-13 | | 88 | <1 | 1.4 | 73 | 22 | 70 |
| 4-14 | | 90 | <1 | 1.5 | 64 | 35 | 67 |
| 4-15 | | 91 | <1 | 1.9 | 60 | 42 | 59 |
| 4-16 | 4.45 | 14 | 18 | 0.7 | 82 | 12 | 35 |
| 4-17 | | 87 | <1 | 1.1 | 75 | 14 | 73 |
| 4-18 | | 89 | <1 | 1.5 | 72 | 25 | 73 |
| 4-19 | | 90 | <1 | 1.6 | 51 | 45 | 62 |
| 4-20 | | 92 | <1 | 1.9 | 47 | 55 | 56 |

As described in Table 4, in the case where the positive electrode 13 included the positive electrode active material (the layered rock-salt lithium-cobalt composite oxide) and the negative electrode 14 included the negative electrode active material (graphite), and where the charge voltage Ec was set to higher than or equal to 4.38 V, each of the capacity the content rate. As also described in Tables 5 to 10, in the case of preparing the electrolytic solution, an addition amount of the cyclic carbonate ester was changed to thereby vary the solvent ratio, and an addition amount of the electrolyte salt was changed to vary the content of the electrolyte salt.

In a case of examining the durability characteristic, a wound body having an elongated shape was fabricated by the above-described procedure, following which a state of the positive electrode active material layer 13B (a portion corresponding to the negative electrode active material layer 14B) in the curved part 10R of an innermost wind was visually observed to thereby determine a state of the positive electrode active material layer 13B.

In this case, a case where the state of the positive electrode active material layer 13B was normal was determined as "A". A case where the positive electrode active material layer 13B was not fractured, but a plurality of pinholes was observed, was determined as "B". A case where the positive electrode active material layer 13B was partially fractured in a width direction (the Y-axis direction), but a width of the fractured portion was less than 50% of a width of the positive electrode active material layer 13B, was determined as "C". A case where the positive electrode active material layer 13B was partially fractured in the width direction and the width of the fractured portion was 50% or more of the width of the positive electrode active material layer 13B, was determined as "D". A case where the positive electrode active material layer 13B was entirely fractured in the width direction and was therefore broken, was determined as "E". A case where peeling off or slipping off of the positive electrode active material layer 13B occurred in the fabrication process and it was therefore not possible to fabricate the positive electrode 13, was determined as "X".

In Tables 5 to 10, a determination result (A to E) of the durability characteristic and an evaluation result (high-temperature retention rate (%)) of the high-temperature cyclability characteristic are written side by side, as written in a lower column: "evaluation result: state determination, high-temperature retention rate". For example, a notation "A, 91%" indicates that the determination result of the durability characteristic is A and the high-temperature retention rate is 91%.

TABLE 5

Charge voltage Ec = 4.38 V, Negative electrode potential Ef = 50 mV,
Negative electrode potential variation Ev = 17 mV
Solvent: EC + DEC + PP, Electrolyte salt: LiPF6, Positive electrode binder: PVDF

| | | | Volume | Content rate = 0.5 wt % | | |
|---|---|---|---|---|---|---|
| Experiment example | Solvent ratio | Content (mol/kg) | density (g/cm$^3$) | Area density = 36 mg/cm$^2$ | Area density = 40 mg/cm$^2$ | Area density = 42 mg/cm$^2$ |
| 5-1 | 0.1 | 1.2 | 4.15 | X, — | X, — | X, — |
| 5-2 | | | 4.10 | X, — | X, — | X, — |
| 5-3 | | | 4.00 | X, — | X, — | X, — |
| 5-4 | | | 3.90 | X, — | X, — | X, — |
| 5-5 | 0.2 | 1.2 | 4.15 | X, — | X, — | X, — |
| 5-6 | | | 4.10 | X, — | X, — | X, — |
| 5-7 | | | 4.00 | X, — | X, — | X, — |
| 5-8 | | | 3.90 | X, — | X, — | X, — |
| 5-9 | 0.5 | 1.2 | 4.15 | X, — | X, — | X, — |
| 5-10 | | | 4.10 | X, — | X, — | X, — |
| 5-11 | | 1.5 | 4.10 | X, — | X, — | X, — |
| 5-12 | | 0.7 | 4.10 | X, — | X, — | X, — |
| 5-13 | | 1.2 | 4.00 | X, — | X, — | X, — |
| 5-14 | | | 3.90 | X, — | X, — | X, — |
| 5-15 | 1.0 | 1.2 | 4.15 | X, — | X, — | X, — |
| 5-16 | | | 4.10 | X, — | X, — | X, — |
| 5-17 | | | 4.00 | X, — | X, — | X, — |
| 5-18 | | | 3.90 | X, — | X, — | X, — |
| 5-19 | 1.2 | 1.2 | 4.15 | X, — | X, — | X, — |
| 5-20 | | | 4.10 | X, — | X, — | X, — |
| 5-21 | | | 4.00 | X, — | X, — | X, — |
| 5-22 | | | 3.90 | X, — | X, — | X, — |

Evaluation result: state determination, high-temperature retention rate

TABLE 6

Charge voltage Ec = 4.38 V, Negative electrode potential Ef = 50 mV,
Negative electrode potential variation Ev = 17 mV
Solvent: EC + DEC + PP, Electrolyte salt: LiPF6, Positive electrode binder: PVDF

| | | | Volume | Content rate = 0.8 wt % | | |
|---|---|---|---|---|---|---|
| Experiment example | Solvent ratio | Content (mol/kg) | density (g/cm$^3$) | Area density = 36 mg/cm$^2$ | Area density = 40 mg/cm$^2$ | Area density = 42 mg/cm$^2$ |
| 5-23 | 0.1 | 1.2 | 4.15 | C, 74% | C, 71% | D, — |
| 4-4 | | | 4.10 | C, 77% | C, 72% | C, 56% |
| 5-24 | | | 4.00 | C, 77% | C, 73% | C, 62% |
| 5-25 | | | 3.90 | C, 79% | C, 75% | C, 65% |
| 5-26 | 0.2 | 1.2 | 4.15 | B, 92% | A, 85% | B, 71% |
| 5-27 | | | 4.10 | A, 91% | A, 86% | B, 73% |
| 5-28 | | | 4.00 | A, 92% | A, 86% | B, 75% |
| 5-29 | | | 3.90 | A, 93% | A, 88% | B, 76% |
| 5-30 | 0.5 | 1.2 | 4.15 | A, 89% | A, 83% | B, 65% |

TABLE 6-continued

Charge voltage Ec = 4.38 V, Negative electrode potential Ef = 50 mV,
Negative electrode potential variation Ev = 17 mV
Solvent: EC + DEC + PP, Electrolyte salt: LiPF6, Positive electrode binder: PVDF

| Experiment example | Solvent ratio | Content (mol/kg) | Volume density (g/cm$^3$) | Content rate = 0.8 wt % | | |
|---|---|---|---|---|---|---|
| | | | | Area density = 36 mg/cm$^2$ | Area density = 40 mg/cm$^2$ | Area density = 42 mg/cm$^2$ |
| 5-31 | | | 4.10 | A, 89% | A, 83% | B, 66% |
| 5-32 | | 1.5 | 4.10 | A, 82% | A, 75% | B, 51% |
| 5-33 | | 0.7 | 4.10 | A, 81% | A, 72% | B, 53% |
| 5-34 | | 1.2 | 4.00 | A, 91% | A, 85% | B, 67% |
| 5-35 | | | 3.90 | A, 92% | A, 85% | B, 69% |
| 5-36 | 1.0 | 1.2 | 4.15 | A, 81% | A, 73% | B, 57% |
| 5-37 | | | 4.10 | A, 82% | A, 74% | B, 58% |
| 5-38 | | | 4.00 | A, 83% | A, 74% | B, 60% |
| 5-39 | | | 3.90 | A, 83% | A, 75% | B, 61% |
| 5-40 | 1.2 | 1.2 | 4.15 | A, 55% | A, 43% | B, 30% |
| 5-41 | | | 4.10 | A, 56% | A, 45% | B, 32% |
| 5-42 | | | 4.00 | A, 58% | A, 44% | B, 35% |
| 5-43 | | | 3.90 | A, 59% | A, 45% | B, 42% |

Evaluation result: state determination, high-temperature retention rate

TABLE 7

Charge voltage Ec = 4.38 V, Negative electrode potential Ef = 50 mV,
Negative electrode potential variation Ev = 17 mV
Solvent: EC + DEC + PP, Electrolyte salt: LiPF6, Positive electrode binder: PVDF

| Experiment example | Solvent ratio | Content (mol/kg) | Volume density (g/cm$^3$) | Content rate = 1.0 wt % | | |
|---|---|---|---|---|---|---|
| | | | | Area density = 36 mg/cm$^2$ | Area density = 40 mg/cm$^2$ | Area density = 42 mg/cm$^2$ |
| 5-44 | 0.1 | 1.2 | 4.15 | C, 72% | C, 65% | D, — |
| 5-45 | | | 4.10 | C, 73% | C, 67% | C, 49% |
| 5-46 | | | 4.00 | C, 73% | C, 68% | C, 52% |
| 5-47 | | | 3.90 | C, 77% | C, 68% | C, 54% |
| 5-48 | 0.2 | 1.2 | 4.15 | B, 91% | B, 84% | C, 69% |
| 5-49 | | | 4.10 | B, 92% | B, 87% | C, 70% |
| 5-50 | | | 4.00 | A, 93% | A, 88% | B, 72% |
| 5-51 | | | 3.90 | A, 93% | A, 89% | B, 75% |
| 5-52 | 0.5 | 1.2 | 4.15 | A, 90% | B, 80% | C, 64% |
| 5-53 | | | 4.10 | A, 88% | A, 82% | B, 65% |
| 5-54 | | 1.5 | 4.10 | A, 79% | B, 72% | C, 56% |
| 5-55 | | 0.7 | 4.10 | A, 80% | A, 71% | C, 56% |
| 5-56 | | 1.2 | 4.00 | A, 92% | A, 83% | B, 66% |
| 5-57 | | | 3.90 | A, 93% | A, 84% | B, 68% |
| 5-58 | 1.0 | 1.2 | 4.15 | A, 82% | B, 72% | C, 56% |
| 5-59 | | | 4.10 | A, 82% | A, 74% | B, 57% |
| 5-60 | | | 4.00 | A, 83% | A, 74% | B, 57% |
| 5-61 | | | 3.90 | A, 84% | A, 75% | B, 58% |
| 5-62 | 1.2 | 1.2 | 4.15 | A, 52% | B, 35% | C, 31% |
| 5-63 | | | 4.10 | A, 53% | A, 37% | B, 30% |
| 5-64 | | | 4.00 | A, 54% | A, 37% | B, 34% |
| 5-65 | | | 3.90 | A, 55% | A, 38% | B, 38% |

Evaluation result: state determination, high-temperature retention rate

TABLE 8

Charge voltage Ec = 4.38 V, Negative electrode potential
Ef = 50 mV, Negative electrode
potential variation Ev = 17 mV
Solvent: EC + DEC + PP, Electrolyte
salt: LiPF$_6$, Positive electrode binder: PVDF

| Experiment example | Solvent ratio | Content (mol/kg) | Volume density (g/cm$^3$) | Content rate = 1.5 wt % | | |
|---|---|---|---|---|---|---|
| | | | | Area density = 36 mg/cm$^2$ | Area density = 40 mg/cm$^2$ | Area density = 42 mg/cm$^2$ |
| 5-66 | 0.1 | 1.2 | 4.15 | C, 73% | D, — | D, — |
| 5-67 | | | 4.10 | C, 73% | D, — | D, — |
| 5-68 | | | 4.00 | C, 74% | C, 66% | D, — |
| 5-69 | | | 3.90 | C, 76% | C, 68% | C, 53% |

TABLE 8-continued

Charge voltage Ec = 4.38 V, Negative electrode potential
Ef = 50 mV, Negative electrode
potential variation Ev = 17 mV
Solvent: EC + DEC + PP, Electrolyte
salt: $LiPF_6$, Positive electrode binder: PVDF Content rate = 1.5 wt %

| Experiment example | Solvent ratio | Content (mol/kg) | Volume density (g/cm³) | Area density = 36 mg/cm² | Area density = 40 mg/cm² | Area density = 42 mg/cm² |
|---|---|---|---|---|---|---|
| 5-70 | 0.2 | 1.2 | 4.15 | B, 89% | C, 83% | C, 54% |
| 5-71 | | | 4.10 | B, 80% | C, 86% | C, 69% |
| 5-72 | | | 4.00 | B, 91% | B, 87% | C, 69% |
| 5-73 | | | 3.90 | A, 91% | B, 87% | C, 71% |
| 5-74 | 0.5 | 1.2 | 4.15 | B, 89% | C, 79% | C, 61% |
| 5-75 | | | 4.10 | A, 90% | B, 81% | C, 62% |
| 5-76 | | 1.5 | 4.10 | A, 77% | B, 72% | C, 55% |
| 5-77 | | 0.7 | 4.10 | A, 75% | B, 71% | C, 54% |
| 5-78 | | 1.2 | 4.00 | A, 91% | B, 80% | C, 67% |
| 5-79 | | | 3.90 | A, 91% | A, 81% | C, 67% |
| 5-80 | 1.0 | 1.2 | 4.15 | B, 79% | B, 68% | C, 54% |
| 5-81 | | | 4.10 | A, 79% | B, 70% | C, 54% |
| 5-82 | | | 4.00 | A, 81% | A, 71% | C, 54% |
| 5-83 | | | 3.90 | A, 82% | A, 72% | C, 55% |
| 5-84 | 1.2 | 1.2 | 4.15 | B, 53% | B, 35% | C, 35% |
| 5-85 | | | 4.10 | A, 53% | B, 38% | C, 34% |
| 5-86 | | | 4.00 | A, 56% | A, 35% | C, 37% |
| 5-87 | | | 3.90 | A, 58% | A, 34% | B, 35% |

Evaluation result: state determination, high-temperature retention rate

TABLE 9

Charge voltage Ec = 4.38 V, Negative electrode potential
Ef = 50 mV, Negative electrode potential variation Ev = 17 mV Solvent:
EC + DEC + PP, Electrolyte salt: $LiPF_6$, Positive electrode binder: PVDF Content rate = 2.5 wt %

| Experiment example | Solvent ratio | Content (mol/kg) | Volume density (g/cm³) | Area density = 36 mg/cm² | Area density = 40 mg/cm² | Area density = 42 mg/cm² |
|---|---|---|---|---|---|---|
| 5-88 | 0.1 | 1.2 | 4.15 | D, — | D, — | D, — |
| 5-89 | | | 4.10 | C, 63% | D, — | D, — |
| 5-90 | | | 4.00 | C, 62% | D, — | D, — |
| 5-91 | | | 3.90 | C, 66% | C, 61% | D, — |
| 5-92 | 0.2 | 1.2 | 4.15 | C, 83% | C, 71% | C, 52% |
| 5-93 | | | 4.10 | C, 84% | C, 72% | C, 57% |
| 5-94 | | | 4.00 | C, 84% | C, 72% | C, 63% |
| 5-95 | | | 3.90 | B, 85% | C, 74% | C, 62% |
| 5-96 | 0.5 | 1.2 | 4.15 | C, 81% | C, 74% | C, 54% |
| 5-97 | | | 4.10 | C, 82% | C, 75% | C, 62% |
| 5-98 | | 1.5 | 4.10 | C, 69% | C, 75% | C, 51% |
| 5-99 | | 0.7 | 4.10 | B, 71% | C, 76% | C, 51% |
| 5-100 | | 1.2 | 4.00 | B, 89% | C, 77% | C, 62% |
| 5-101 | | | 3.90 | B, 87% | B, 77% | C, 62% |
| 5-102 | 1.0 | 1.2 | 4.15 | B, 71% | C, 54% | C, 42% |
| 5-103 | | | 4.10 | B, 72% | C, 55% | C, 45% |
| 5-104 | | | 4.00 | B, 75% | B, 62% | C, 47% |
| 5-105 | | | 3.90 | B, 75% | B, 63% | C, 51% |
| 5-106 | 1.2 | 1.2 | 4.15 | B, 54% | B, 36% | C, 35% |
| 5-107 | | | 4.10 | B, 54% | B, 38% | C, 34% |
| 5-108 | | | 4.00 | B, 56% | B, 38% | C, 36% |
| 5-109 | | | 3.90 | B, 57% | B, 40% | B, 35% |

Evaluation result: state determination, high-temperature retention rate

TABLE 10

Charge voltage Ec = 4.38 V, Negative electrode potential Ef = 50 mV,
Negative electrode potential variation Ev = 17 mV Solvent:
EC + DEC + PP, Electrolyte salt: $LiPF_6$, Positive electrode binder: PVDF Content rate = 3.0 wt %

| Experiment example | Solvent ratio | Content (mol/kg) | Volume density (g/cm³) | Area density = 36 mg/cm² | Area density = 40 mg/cm² | Area density = 42 mg/cm² |
|---|---|---|---|---|---|---|
| 5-110 | 0.1 | 1.2 | 4.15 | E, — | E, — | E, — |
| 5-111 | | | 4.10 | D, — | E, — | E, — |
| 5-112 | | | 4.00 | D, — | E, — | E, — |
| 5-113 | | | 3.90 | D, — | E, — | E, — |
| 5-114 | 0.2 | 1.2 | 4.15 | E, — | E, — | E, — |
| 5-115 | | | 4.10 | D, — | E, — | E, — |
| 5-116 | | | 4.00 | D, — | E, — | E, — |
| 5-117 | | | 3.90 | D, — | E, — | E, — |
| 5-118 | 0.5 | 1.2 | 4.15 | D, — | E, — | E, — |
| 5-119 | | | 4.10 | D, — | E, — | E, — |
| 5-120 | | 1.5 | 4.10 | D, — | E, — | E, — |
| 5-121 | | 0.7 | 4.10 | D, — | E, — | E, — |
| 5-122 | | 1.2 | 4.00 | D, — | E, — | E, — |
| 5-123 | | | 3.90 | D, — | E, — | E, — |
| 5-124 | 1.0 | 1.2 | 4.15 | D, — | E, — | E, — |
| 5-125 | | | 4.10 | D, — | E, — | E, — |
| 5-126 | | | 4.00 | D, — | E, — | E, — |
| 5-127 | | | 3.90 | D, — | E, — | E, — |
| 5-128 | 1.2 | 1.2 | 4.15 | E, — | E, — | E, — |
| 5-129 | | | 4.10 | D, — | E, — | E, — |
| 5-130 | | | 4.00 | D, — | E, — | E, — |
| 5-131 | | | 3.90 | D, — | E, — | E, — |

Evaluation result: state determination, high-temperature retention rate

In the case where the two configuration conditions (the negative electrode potential Ef and the negative electrode potential variation Ev) were satisfied (Experiment examples 5-1 to 5-131), the state of the positive electrode active material layer 13B and the high-temperature retention rate each varied depending on the configuration of the positive electrode 13 (the area density, the volume density, and the content rate) and the composition of the electrolytic solution (the solvent ratio and the content).

Specifically, in order to increase an energy density, three configuration conditions, i.e., the area density being greater than or equal to 36 mg/cm², the volume density being greater than or equal to 3.90 g/cm³, and the content being from 0.7 mol/kg to 1.2 mol/kg both inclusive, were satisfied. In this case, if two conditions, i.e., the solvent ratio being from 0.2 to 1 both inclusive and the content rate being from 0.8 wt % to 2.5 wt % both inclusive, were satisfied (for example, Experiment examples 5-26 to 5-39), a high high-temperature retention rate was obtained while securing the state of the positive electrode active material layer 13B as compared with a case where the two configuration conditions were not satisfied (for example, Experiment examples 4-4, 5-1 to 5-25, and 5-40 to 5-43).

Experiment Examples 6-1 to 6-10

As described in Table 11, secondary batteries were fabricated following which the battery characteristics of the secondary batteries were examined by similar procedures except that the configuration of the positive electrode binder (the kind and the copolymerization amount (wt %)) was changed.

In the case of fabricating the positive electrode 13, newly added as the positive electrode binder were: a copolymer (VDF/TFE) of vinylidene fluoride and tetrafluoroethylene, a copolymer (VDF/HFP) of vinylidene fluoride and hexafluoropropylene, and a copolymer (VDF/TFE/HFP) of vinylidene fluoride, tetrafluoroethylene, and hexafluoropropylene. In this case, the respective copolymerization amounts of VDF and HFP were set as described in Table 11.

TABLE 11

Charge voltage Ec = 4.38 V, Negative electrode potential Ef = 50 mV,
Negative electrode potential variation Ev = 17 mV

| Experiment example | Positive electrode binder Kind | Copolymerization amount (wt %) | Solvent ratio | Electrolyte salt Kind | Content (mol/kg) | Volume density (g/cm$^3$) | Content rate = 1.0 wt % Area density = 42 mg/cm$^2$ |
|---|---|---|---|---|---|---|---|
| 5-52 | PVDF | — | 0.5 | LiPF$_6$ | 1.2 | 4.10 | C, 64% |
| 6-1 | VDF/TFE | 0.1 | | | | | B, 67% |
| 6-2 | | 1 | | | | | B, 68% |
| 6-3 | | 5 | | | | | B, 68% |
| 6-4 | | 10 | | | | | B, 62% |
| 6-5 | | 20 | | | | | A, 61% |
| 6-6 | VDF/HFP | 0.2 | | | | | B, 64% |
| 6-7 | | 1 | | | | | B, 62% |
| 6-8 | | 5 | | | | | B, 61% |
| 6-9 | VDF/TFE/HFP | 10/0.5 | | | | | B, 65% |
| 6-10 | VDF/TFE/HFP | 10/5 | | | | | A, 64% |

Similar results were obtained also in the case of changing the configuration of the positive electrode binder (the kind of the copolymerization amount) (Experiment examples 6-1 to 6-10). In other words, a high high-temperature retention rate was obtained while securing the state of the positive electrode active material layer 13B even if the configuration of the positive electrode binder was changed.

In particular, usage of the copolymer as the positive electrode binder prevented the positive electrode active material layer 13B from being easily fractured. In this case, the positive electrode active material layer 13B was sufficiently prevented from being easily fractured if the copolymerization amount of TFE was from 0.1 wt % to 20 wt % both inclusive and the copolymerization amount of HFP was from 0.2 wt % to 5 wt % both inclusive.

Experiment Examples 7-1 to 7-8

As described in Table 12, secondary batteries were fabricated following which the battery characteristics of the secondary batteries were examined by similar procedures except that the composition of the electrolytic solution (the kind of solvent and the kind of electrolyte salt) was changed.

In a case of preparing the electrolytic solution, new materials were used as the solvent, and a new material as used as the electrolyte salt. Specifically: dimethyl carbonate (DMC) was used as the chain carbonate ester; ethyl propionate (EP) and methyl propionate (MP) were used as the chain carboxylate ester; and lithium tetrafluoroborate (LiBF$_4$) was used as the electrolyte salt.

TABLE 12

Charge voltage Ec = 4.38 V, Negative electrode potential Ef = 50 mV,
Negative electrode potential variation Ev = 17 mV

| Experiment example | Solvent Cyclic carbonate ester | Solvent Chain carbonate ester | Solvent Chain carboxylate ester | Solvent ratio | Electrolyte salt Kind | Content (mol/kg) | Volume density (g/cm$^3$) | Content rate = 1.0 wt % Area density = 42 mg/cm$^2$ |
|---|---|---|---|---|---|---|---|---|
| 5-53 | EC + PC | DEC | PP | 0.5 | LiPF$_6$ | 1.2 | 4.10 | A, 82% |
| 7-1 | PC | DEC | PP | | | | | A, 65% |
| 7-2 | EC | DEC | PP | | | | | A, 68% |
| 7-3 | EC + PC | DMC | PP | | | | | A, 63% |
| 7-4 | EC + PC | DEC | EP | | | | | A, 88% |
| 7-5 | EC + PC | DEC | MP | | | | | A, 62% |
| 7-6 | EC + PC | — | PP | | | | | A, 83% |
| 7-7 | EC + PC | DEC | — | | | | | A, 72% |
| 7-8 | EC + PC | DEC | PP | 0.5 | LiBF$_4$ | 1.2 | 4.10 | A, 61% |

Similar results were obtained also in the case of changing the composition of the electrolytic solution (Experiment examples 7-1 to 7-8). In other words, a high high-temperature retention rate was obtained while securing the state of the positive electrode active material layer 13B even if the composition of the electrolytic solution was changed.

Experiment Examples 8-1 to 8-6

As described in Table 13, secondary batteries were fabricated following which the battery characteristics of the secondary batteries were examined by similar procedures except that the configuration of the negative electrode 14 (the median diameter D50 (μm) of the negative electrode active material (artificial graphite)) was changed, and that a low-temperature cyclability characteristic was newly evaluated.

TABLE 13

Charge voltage Ec = 4.38 V,
Negative electrode potential Ef = 50 mV,
Negative electrode potential variation Ev = 17 mV,
Solvent ratio = 0.2, Content = 1.2 mol/kg,
Volume density = 4.10 g/cm$^3$,
Content rate = 1.0 wt %, Area density = 40 mg/cm$^2$

| Experiment example | D50 (m) | Content rate = 1.0 wt % Area density = 40 mg/cm$^2$ | Low-temperature retention rate (%) |
|---|---|---|---|
| 8-1 | 2 | A, 52% | 67 |
| 8-2 | 3.5 | A, 64% | 75 |
| 8-3 | 5 | A, 75% | 72 |
| 5-53 | 10 | A, 82% | 73 |
| 8-4 | 20 | A, 81% | 71 |
| 8-5 | 30 | A, 77% | 51 |
| 8-6 | 50 | A, 69% | 32 |

In a case where the median diameter D50 was within an appropriate range (from 3.5 μm to 30 μm both inclusive) (Experiment examples 5-53 and 8-2 to 8-5), the high-temperature retention rate increased and the low-temperature retention rate increased as compared with a case where the median diameter D50 was outside the appropriate range (Experiment examples 8-1 and 8-6). In particular, in a case where the median diameter D50 was from 5 μm to 25 μm both inclusive (Experiment examples 5-53, 8-3, and 8-4), a high low-temperature retention rate was obtained and a high high-temperature retention rate was also obtained.

Experiment Examples 9-1 to 9-5

As described in Table 14, secondary batteries were fabricated following which the battery characteristics of the secondary batteries were examined by similar procedures except that the configuration of the negative electrode 14 (the spacing S (nm) of the (002) plane of the negative electrode active material (the artificial graphite)) was changed.

TABLE 14

Charge voltage Ec = 4.38 V,
Negative electrode potential Ef = 50 mV,
Negative electrode potential variation Ev = 17 mV,
Solvent ratio = 0.2, Content = 1.2 mol/kg,
Volume density = 4.10 g/cm$^3$,
Content rate = 1.0 wt %, Area density = 40 mg/cm$^2$

| Experiment example | Spacing S (nm) | Content rate = 1.0 wt % Area density = 40 mg/cm$^2$ | Low-temperature retention rate (%) |
|---|---|---|---|
| 9-1 | 0.3355 | A, 75% | 63 |
| 9-2 | 0.3356 | A, 81% | 71 |
| 5-53 | 0.3360 | A, 82% | 73 |
| 9-3 | 0.3363 | A, 80% | 80 |
| 9-4 | 0.3370 | A, 73% | 82 |
| 9-5 | 0.3375 | A, 61% | 84 |

In a case where the spacing S was within an appropriate range (from 0.3355 nm to 0.3370 nm both inclusive) (Experiment examples 5-53 and 9-1 to 9-4), the high-temperature retention rate increased as compared with a case where the spacing S was outside the appropriate range (Experiment example 9-5). In particular, in a case where the spacing S was within the range of 0.3356 nm to 0.3363 nm (Experiment examples 5-53, 9-2, and 9-3), the high-temperature retention rate further increased while obtaining a high low-temperature retention rate.

Based upon the results described in Tables 4 to 14, in the case where the positive electrode 13 included the positive electrode active material (the layered rock-salt lithium-cobalt composite oxide) and the positive electrode binder (the vinylidene fluoride-based polymer compound), the negative electrode 14 included the negative electrode active material (graphite), and the electrolytic solution included the solvent (which included the cyclic carbonate ester and the chain carbonate ester, included the cyclic carbonate ester and the chain carboxylate ester, or included the cyclic carbonate ester, the chain carbonate ester, and the chain carboxylate ester), and where the above-described seven configuration conditions (the negative electrode potential Ef, the negative electrode potential variation Ev, the area density, the volume density, the content rate, the solvent ratio, and the content) were satisfied: the capacity retention characteristic, the high-temperature cyclability characteristic, the high-temperature swelling characteristic, the low-temperature cyclability characteristic, and the durability characteristic were each improved. Accordingly, superior battery characteristics of the secondary batteries were obtained.

Experiment Examples 10-1 to 10-20

Next, laminated secondary batteries (lithium-ion secondary batteries) illustrated in FIGS. 1 and 2 were fabricated, following which battery characteristics of the secondary batteries were evaluated as described below.

In a case of fabricating the positive electrode 13, first, 91 parts by mass of the positive electrode active material (lithium cobalt oxide (LiCoO$_2$) serving as the layered rock-salt lithium-cobalt composite oxide), 3 parts by mass of the positive electrode binder (polyvinylidene difluoride), and 6 parts by mass of the positive electrode conductor (graphite) were mixed with each other to thereby obtain a positive electrode mixture. Thereafter, the positive electrode mixture was put into an organic solvent (N-methyl-2-pyrrolidone), following which the organic solvent was stirred to thereby prepare a paste positive electrode mixture slurry. Thereafter, the positive electrode mixture slurry was applied on both sides of the positive electrode current collector 13A (a band-shaped aluminum foil having a thickness of 12 µm) by means of a coating apparatus, following which the applied positive electrode mixture slurry was dried to thereby form the positive electrode active material layers 13B. Lastly, the positive electrode active material layers 13B were compression-molded by means of a roll pressing machine.

In a case of fabricating the negative electrode 14, first, 97 parts by mass of the negative electrode active material particles (artificial graphite having a median diameter D50A of 10 µm and spacing S of the (002) plane of 0.3360 nm) and 1.5 parts by mass of the negative electrode binder (sodium carboxymethyl cellulose) were mixed with each other to thereby obtain a negative electrode mixture precursor. Thereafter, the negative electrode mixture precursor was put into an aqueous solvent (deionized water), following which 1.5 parts by mass, in terms of solid content, of the negative electrode binder (a styrene-butadiene-rubber dispersion liquid) was put into the aqueous solvent to thereby prepare a paste negative electrode mixture slurry. Thereafter, the negative electrode mixture slurry was applied on both sides of the negative electrode current collector 14A (a band-shaped copper foil having a thickness of 15 µm) by means of a coating apparatus, following which the applied negative electrode mixture slurry was dried to thereby form the negative electrode active material layers 14B. Lastly, the negative electrode active material layers 14B were compression-molded by means of a roll pressing machine (with a volume density of 1.6 g/cm$^3$ and an integrated intensity ratio of 568).

In the case of fabricating the positive electrode 13 and the negative electrode 14, a mixture ratio (a weight ratio) between the positive electrode active material and the negative electrode active material was adjusted to thereby vary each of the negative electrode potential Ef (mV) and the negative electrode potential variation Ev (mV). Each of the negative electrode potential Ef and the negative electrode potential variation Ev in the case where the charge voltage Ec was set to 4.38 V or 4.45 V was as described in Table 15. Here, the maximum discharge capacity was set to 1950 mAh to 2050 mAh both inclusive.

In a case of preparing the electrolytic solution, the electrolyte salt (lithium hexafluorophosphate) was added to a solvent (ethylene carbonate, propylene carbonate, and diethyl carbonate), following which the solvent was stirred. In this case, a mixture ratio (a weight ratio) of ethylene carbonate/propylene carbonate/diethyl carbonate in the solvent was set to 15:15:70, and a content of the electrolyte salt with respect to the solvent was set to 1.2 mol/kg.

In a case of assembling the secondary battery, first, the positive electrode lead 11 including aluminum was welded to the positive electrode current collector 13A, and the negative electrode lead 12 including copper was welded to the negative electrode current collector 14A. Thereafter, the positive electrode 13 and the negative electrode 14 were stacked on each other with the separator 15 (a fine-porous polyethylene film having a thickness of 15 µm) interposed therebetween to thereby obtain a stacked body. Thereafter, the stacked body was wound, following which the protective tape was attached to a surface of the stacked body to thereby obtain a wound body.

Thereafter, the outer package member 20 was folded in such a manner as to sandwich the wound body, following which the outer edges of two sides of the outer package member 20 were thermal fusion bonded to each other. As the outer package member 20, an aluminum laminated film was used in which a surface protective layer (a nylon film having a thickness of 25 µm), a metal layer (an aluminum foil having a thickness of 40 µm), and a fusion-bonding layer (a polypropylene film having a thickness of 30 µm) were stacked in this order. In this case, the sealing film 31 (a polypropylene film having a thickness of 5 µm) was interposed between the outer package member 20 and the positive electrode lead 11, and the sealing film 32 (a polypropylene film having a thickness of 5 µm) was interposed between the outer package member 20 and the negative electrode lead 12.

Lastly, the electrolytic solution was injected into the outer package member 20 and thereafter, the outer edges of one of the remaining sides of the outer package member 20 were thermal fusion bonded to each other in a reduced-pressure environment. Thus, the wound body was impregnated with the electrolytic solution, thereby forming the wound electrode body 10 and sealing the wound electrode body 10 in the outer package member 20. As a result, the laminated secondary battery was completed.

Evaluation of battery characteristics of the secondary batteries revealed the results described in Table 15. A capacity retention characteristic, a high-temperature cyclability characteristic, a high-temperature swelling characteristic, and a low-temperature cyclability characteristic were evaluated here as the battery characteristics.

In a case of examining the capacity retention characteristic, first, the secondary battery was charged and discharged for one cycle in an ambient temperature environment (at a temperature of 23° C.) in order to stabilize a state of the secondary battery. Upon charging, the secondary battery was charged with a constant current of 0.2 C until a battery voltage reached the charge voltage Ec (4.38 V or 4.45 V), and was thereafter charged with a constant voltage of the battery voltage corresponding to the charge voltage Ec until a current reached 0.05 C. Upon discharging, the secondary battery was discharged with a constant current of 0.2 C until a battery voltage reached the discharge voltage Ed (3.00 V). It should be understood that 0.2 C and 0.05 C are values of currents that cause battery capacities (theoretical capacities) to be completely discharged in 5 hours and 20 hours, respectively.

Thereafter, the secondary battery was charged and discharged for another cycle in the same environment and in the above-described charging and discharging conditions to thereby measure a discharge capacity (a discharge capacity before varying the charge voltage Ec). Thereafter, the secondary battery was charged and discharged for another cycle in the same environment and in similar charging and discharging conditions except that the charge voltage Ec was lowered by 10 mV to thereby measure a discharge capacity (a discharge capacity after varying the charge voltage Ec). Lastly, the following was calculated: capacity variation rate (%)=[(discharge capacity before varying charge voltage Ec−discharge capacity after varying charge voltage Ec)/discharge capacity before varying charge voltage Ec]×100.

In a case of examining the high-temperature cyclability characteristic, the state of the secondary battery was stabilized by the above procedures, following which the secondary battery was charged and discharged for one cycle in an ambient temperature environment (at a temperature of 23° C.) to thereby measure a second-cycle discharge capacity. Thereafter, the secondary battery was charged and discharged for another 700 cycles in a high temperature environment (at a temperature of 45° C.) to thereby measure a 702nd-cycle discharge capacity. Lastly, the following was calculated: high-temperature retention rate (%)=(702nd-cycle discharge capacity/second-cycle discharge capacity)× 100. Charging and discharging conditions were similar to those for the case of examining the capacity retention characteristic, except that the current at the time of charging was changed to 0.7 C and that the current at the time of discharging was changed to 1 C. It should be understood that 0.7 C and 1 C are values of currents that cause battery capacities (theoretical capacities) to be completely discharged in 10/7 hours and 1 hour, respectively. In a case of examining the high-temperature swelling characteristic, in the above-described procedures of examining the high-temperature cyclability characteristic, a thickness (a second-cycle thickness) of the secondary battery was measured at the time of measuring the second-cycle discharge capacity, and a thickness (a 702nd-cycle thickness) of the secondary battery was measured at the time of measuring the 702nd-cycle discharge capacity. Thus, the following was calculated: swelling increase rate (%)=[(702nd-cycle thickness−second-cycle thickness)/second-cycle thickness]×100.

In a case of examining the low-temperature cyclability characteristic, the state of the secondary battery was stabilized by the above procedures, following which the secondary battery was charged and discharged for one cycle in an ambient temperature environment (at a temperature of 23° C.) to thereby measure the second-cycle discharge capacity. Thereafter, the secondary battery was charged and discharged for another 100 cycles in a low temperature environment (at a temperature of 0° C.) to thereby measure a 102nd-cycle discharge capacity. Lastly, the following was calculated: low-temperature retention rate (%)=(102nd-cycle discharge capacity/second-cycle discharge capacity)× 100. Charging and discharging conditions were similar to those for the case of examining the capacity retention characteristic, except that the current at the time of charging was changed to 0.5 C and that the current at the time of discharging was changed to 0.5 C.

the negative electrode 14 included the negative electrode active material particles (graphite), and where the charge voltage Ec was set to higher than or equal to 4.38 V, each of the capacity variation rate, the high-temperature retention rate, the swelling increase rate, and the low-temperature retention rate varied depending on the negative electrode potential Ef and the negative electrode potential variation Ev.

Specifically, in a case where two configuration conditions, i.e., the negative electrode potential Ef being from 19 mV to 86 mV both inclusive and the negative electrode potential variation Ev being greater than or equal to 1 mV, were satisfied together (Experiment examples 10-1 to 10-10), the capacity variation rate and the swelling increase rate each decreased and the high-temperature retention rate and the low-temperature retention rate each increased slightly, as compared with a case where the two configuration conditions were not satisfied together (Experiment examples 10-11 to 10-20).

Experiment Examples 11-1 to 11-16

As described in Table 16, secondary batteries were fabricated following which the battery characteristics of the secondary batteries were examined by similar procedures except that the configuration of the negative electrode 14 (the kind of the negative electrode active material and presence or absence of coverage) was changed.

As described in Table 16, in a case of fabricating the negative electrode 14, other artificial graphite and spherical natural graphite whose integrated intensity ratios were different from each other were newly used, and the median diameter D50A (μm) and the volume density (g/cm$^3$) were varied. Further, the second negative electrode active material particles (silicon oxide (SiO) serving as the silicon-containing material) were added to the first negative electrode active material particles. In this case, as described in Table 16, the median diameter D50B and the content rate (wt %) were varied.

TABLE 15

Positive electrode active material: LiCoO$_2$, Negative electrode active material: artificial graphite

| Experiment example | Charge voltage Ec (V) | Negative electrode potential Ef (mV) | Negative electrode potential variation Ev (mV) | Capacity variation rate (%) | High-temperature retention rate (%) | Swelling increase rate (%) | Low-temperature retention rate (%) |
|---|---|---|---|---|---|---|---|
| 10-1 | 4.38 | 86 | 1 | 0.8 | 83 | 12 | 72 |
| 10-2 | | 80 | 3 | 0.5 | 86 | 9 | 73 |
| 10-3 | | 68 | 9 | 0.5 | 90 | 8 | 73 |
| 10-4 | | 50 | 17 | 0.5 | 89 | 8 | 74 |
| 10-5 | | 19 | 28 | 0.5 | 89 | 8 | 72 |
| 10-6 | 4.45 | 86 | 1 | 0.7 | 81 | 14 | 71 |
| 10-7 | | 80 | 3 | 0.5 | 82 | 12 | 72 |
| 10-8 | | 66 | 10 | 0.5 | 86 | 10 | 72 |
| 10-9 | | 34 | 23 | 0.5 | 84 | 10 | 81 |
| 10-10 | | 19 | 28 | 0.5 | 83 | 11 | 80 |
| 10-11 | 4.38 | 12 | 15 | 0.7 | 83 | 8 | 45 |
| 10-12 | | 87 | <1 | 1.3 | 78 | 15 | 72 |
| 10-13 | | 88 | <1 | 1.4 | 73 | 22 | 70 |
| 10-14 | | 90 | <1 | 1.5 | 64 | 35 | 67 |
| 10-15 | | 91 | <1 | 1.9 | 60 | 42 | 59 |
| 10-16 | 4.45 | 14 | 18 | 0.7 | 82 | 12 | 35 |
| 10-17 | | 87 | <1 | 1.1 | 75 | 14 | 73 |
| 10-18 | | 89 | <1 | 1.5 | 72 | 25 | 73 |
| 10-19 | | 90 | <1 | 1.6 | 51 | 45 | 62 |
| 10-20 | | 92 | <1 | 1.9 | 47 | 55 | 56 |

As described in Table 15, in the case where the positive electrode 13 included the positive electrode active material (the layered rock-salt lithium-cobalt composite oxide) and The column of "Coverage" provided in Table 16 indicates the presence or absence of the coverage on the surfaces of the second negative electrode active material particles with an electrically conductive material (graphite). In a case where the electrically conductive material was used to cover the surfaces of the second negative electrode active material particles, graphite was deposited on the surfaces of the second negative electrode active material particles by the CVD method using graphite as a carbon source.

Further, in a case where the second negative electrode active material particles were used (Experiment example 11-16), the high-temperature retention rate and the low-temperature retention rate each increased and the swelling increase rate decreased, as compared with a case where the second negative electrode active material particles were not used (Experiment example 11-7). Such a tendency was obtained in a similar manner also in a case where the second negative electrode active material particles were used simi-

TABLE 16

Charge voltage Ec = 4.38 V, Negative electrode potential Ef = 50 mV, Negative electrode potential variation Ev = 17 mV

| Experiment example | First negative electrode active material particles Kind | D50A (μm) | Second negative electrode active material particles Kind | D50B (μm) | Content rate (mass %) | Coverage | Negative electrode active material layer Volume density (g/cm$^3$) | Capacity Integrated intensity ratio | High-temperature variation rate (%) | Swelling retention rate (%) | Low-temperature increase rate (%) | retention rate (%) |
|---|---|---|---|---|---|---|---|---|---|---|---|---|
| 10-4 | Artificial graphite | 10 | — | — | — | Absent | 1.6 | 568 | 0.5 | 89 | 8 | 74 |
| 11-1 | Spherical natural graphite | 10 | — | — | — | Absent | 1.6 | 793 | 0.5 | 73 | 12 | 55 |
| 11-2 | Artificial graphite | 10 | — | — | — | Absent | 1.6 | 345 | 0.5 | 92 | 8 | 79 |
| 11-3 | Artificial graphite | 20 | — | — | — | Absent | 1.6 | 389 | 0.5 | 88 | 8 | 77 |
| 11-4 | Artificial graphite | 5 | — | — | — | Absent | 1.6 | 312 | 0.6 | 87 | 10 | 81 |
| 11-5 | Artificial graphite | 1 | — | — | — | Absent | 1.6 | 234 | 0.5 | 90 | 8 | 79 |
| 11-6 | Artificial graphite | 10 | — | — | — | Absent | 1.7 | 417 | 0.5 | 88 | 8 | 76 |
| 11-7 | Artificial graphite | 10 | — | — | — | Absent | 1.8 | 489 | 0.5 | 88 | 10 | 75 |
| 11-8 | Artificial graphite | 20 | SiO | 10 | 1.5 | Present | 1.6 | 384 | 0.5 | 85 | 11 | 80 |
| 11-9 | Artificial graphite | 10 | SiO | 5 | 1.5 | Present | 1.6 | 343 | 0.5 | 81 | 12 | 82 |
| 11-10 | Artificial graphite | 5 | SiO | 1 | 1.5 | Present | 1.6 | 307 | 0.5 | 85 | 12 | 84 |
| 11-11 | Artificial graphite | 10 | SiO | 5 | 5 | Present | 1.6 | 339 | 0.5 | 91 | 12 | 84 |
| 11-12 | Artificial graphite | 10 | SiO | 5 | 3 | Present | 1.6 | 341 | 0.5 | 83 | 15 | 87 |
| 11-13 | Artificial graphite | 10 | SiO | 5 | 1 | Present | 1.6 | 343 | 0.5 | 85 | 14 | 84 |
| 11-14 | Artificial graphite | 10 | SiO | 5 | 0.5 | Present | 1.6 | 344 | 0.5 | 88 | 11 | 82 |
| 11-15 | Artificial graphite | 10 | SiO | 5 | 0.1 | Present | 1.6 | 346 | 0.5 | 89 | 10 | 81 |
| 11-16 | Artificial graphite | 10 | SiO | 5 | 1.5 | Absent | 1.5 | 342 | 0.5 | 89 | 9 | 79 |

In the case where the two configuration conditions (the negative electrode potential Ef and the negative electrode potential variation Ev) were satisfied (Experiment examples 11-1 to 11-16), the capacity variation rate, the high-temperature retention rate, the swelling increase rate, and the low-temperature retention rate each varied depending on the configuration of the negative electrode 14.

Specifically, if the volume density was set to greater than or equal to 1.5 g/cm$^3$ in order to increase the energy density, in a case where two configuration conditions, i.e., the median diameter D50A being less than or equal to 20 μm and the integrated intensity ratio being less than or equal to 500, were satisfied together (Experiment examples 11-2 to 11-7), the low-temperature retention rate increased while securing substantially equal capacity variation rate, high-temperature retention rate, and swelling increase rate, as compared with a case where the two configuration conditions were not satisfied together (Experiment examples 10-4 and 11-1).

larly (Experiment examples 11-8 to 11-15). In particular, in the case where the second negative electrode active material particles were used, and where the median diameter D50B was from 1 μm to 10 μm both inclusive and the content rate was from 0.1 wt % to 5 wt % both inclusive, a high high-temperature retention rate and a high low-temperature retention rate were obtained while suppressing each of the capacity variation rate and the swelling increase rate.

Still further, in a case where the second negative electrode active material particles were covered (Experiment example 11-9), the low-temperature retention rate further increased, as compared with a case where the second negative electrode active material particles were not covered (Experiment example 11-16).

Experiment Examples 12-1 to 12-5

As described in Table 17, secondary batteries were fabricated following which the battery characteristics of the secondary batteries were examined by similar procedures except that the configuration of the negative electrode 14 (the spacing S (nm) of the (002) plane of the negative electrode active material (artificial graphite)) was changed, and that a battery capacity cyclability characteristic was newly evaluated.

TABLE 17

Charge voltage Ec = 4.38 V, Negative electrode potential Ef = 50 mV, Negative electrode potential variation Ev = 17 mV, D50A = 10 μm, Volume density = 1.6 g/cm³, Integrated intensity ratio = 345

| Experiment example | Spacing S (nm) | Capacity variation rate (%) | High-temperature retention rate (%) | Swelling increase rate (%) | Low-temperature retention rate (%) |
|---|---|---|---|---|---|
| 12-1 | 0.3355 | 0.5 | 72 | 15 | 63 |
| 12-2 | 0.3356 | 0.5 | 75 | 13 | 78 |
| 11-2 | 0.3360 | 0.5 | 92 | 8 | 79 |
| 12-3 | 0.3363 | 0.5 | 88 | 9 | 81 |
| 12-4 | 0.3370 | 0.5 | 84 | 10 | 84 |
| 12-5 | 0.3375 | 0.5 | 81 | 13 | 87 |

In a case where the spacing S was within an appropriate range (from 0.3355 nm to 0.3370 nm both inclusive) (Experiment examples 11-2 and 12-1 to 12-4), a high high-temperature retention rate and a high low-temperature retention rate were obtained while suppressing the swelling increase rate, as compared with a case where the spacing S was outside the appropriate range (Experiment example 12-5). In particular, in a case where the spacing S was within the range of 0.3356 nm to 0.3363 nm (Experiment examples 11-2, 12-2, and 12-3), a further higher high-temperature retention rate and a further higher low-temperature retention rate were obtained while further suppressing the swelling increase rate.

Based upon the results described in Tables 15 to 17, in the case where the positive electrode 13 included the positive electrode active material (the layered rock-salt lithium-cobalt composite oxide) and the negative electrode 14 included the first negative electrode active material particles (graphite), and where the above-described five configuration conditions (the negative electrode potential Ef, the negative electrode potential variation Ev, the median diameter D50A, the volume density, and the integrated intensity ratio) were satisfied: the capacity retention characteristic, the high-temperature cyclability characteristic, the high-temperature swelling characteristic, and the low-temperature cyclability characteristic were each improved. Accordingly, superior battery characteristics of the secondary batteries were obtained.

Experiment Examples 13-1 to 13-20

Next, laminated secondary batteries (lithium-ion secondary batteries) illustrated in FIGS. 1 and 2 were fabricated, following which battery characteristics of the secondary batteries were evaluated as described below.

[Fabrication of Secondary Battery]

In a case of fabricating the positive electrode 13, first, 91 parts by mass of the positive electrode active material (lithium cobalt oxide ($LiCoO_2$) serving as the layered rock-salt lithium-cobalt composite oxide), 3 parts by mass of the positive electrode binder (polyvinylidene difluoride), and 6 parts by mass of the positive electrode conductor (graphite) were mixed with each other to thereby obtain a positive electrode mixture. Thereafter, the positive electrode mixture was put into an organic solvent (N-methyl-2-pyrrolidone), following which the organic solvent was stirred to thereby prepare a paste positive electrode mixture slurry. Thereafter, the positive electrode mixture slurry was applied on both sides of the positive electrode current collector 13A (a band-shaped aluminum foil having a thickness of 12 μm) by means of a coating apparatus, following which the applied positive electrode mixture slurry was dried to thereby form the positive electrode active material layers 13B. Lastly, the positive electrode active material layers 13B were compression-molded by means of a roll pressing machine.

In a case of forming the positive electrode active material layer 13B, the area density was set to 42.9 mg/m² and the volume density was set to 4.2 g/cm³. A piercing test was performed using the positive electrode 13, and the piercing strength was 0.8 N; therefore, the degree of durability was 225.

In a case of fabricating the negative electrode 14, first, 97 parts by mass of the negative electrode active material (artificial graphite) and 1.5 parts by mass of the negative electrode binder (sodium carboxymethyl cellulose) were mixed with each other to thereby obtain a negative electrode mixture precursor. Thereafter, the negative electrode mixture precursor was put into an aqueous solvent (deionized water), following which 1.5 parts by mass, in terms of solid content, of the negative electrode binder (a styrene-butadiene-rubber dispersion liquid) was put into the aqueous solvent to thereby prepare a paste negative electrode mixture slurry. Thereafter, the negative electrode mixture slurry was applied on both sides of the negative electrode current collector 14A (a band-shaped copper foil having a thickness of 15 μm) by means of a coating apparatus, following which the applied negative electrode mixture slurry was dried to thereby form the negative electrode active material layers 14B. Lastly, the negative electrode active material layers 14B were compression-molded by means of a roll pressing machine.

In the case of fabricating the positive electrode 13 and the negative electrode 14, a mixture ratio (a weight ratio) between the positive electrode active material and the negative electrode active material was adjusted to thereby vary each of the negative electrode potential Ef (mV) and the negative electrode potential variation Ev (mV). Each of the negative electrode potential Ef and the negative electrode potential variation Ev in the case where the charge voltage Ec was set to 4.38 V or 4.45 V was as described in Table 18. Here, the maximum discharge capacity was set to 1950 mAh to 2050 mAh both inclusive.

In a case of preparing the electrolytic solution, the electrolyte salt (lithium hexafluorophosphate) was added to a solvent (ethylene carbonate, propylene carbonate, and diethyl carbonate), following which the solvent was stirred. In this case, a mixture ratio (a weight ratio) of ethylene carbonate/propylene carbonate/diethyl carbonate in the solvent was set to 15:15:70, and a content of the electrolyte salt with respect to the solvent was set to 1.2 mol/kg.

In a case of assembling the secondary battery, first, the positive electrode lead 11 including aluminum was welded to the positive electrode current collector 13A, and the negative electrode lead 12 including copper was welded to the negative electrode current collector 14A. Thereafter, the positive electrode 13 and the negative electrode 14 were stacked on each other with the separator 15 (a fine-porous polyethylene film having a thickness of 15 μm) interposed therebetween to thereby obtain a stacked body. Thereafter, the stacked body was wound, following which the protective tape was attached to a surface of the stacked body to thereby obtain a wound body.

Thereafter, the outer package member 20 was folded in such a manner as to sandwich the wound body, following which the outer edges of two sides of the outer package member 20 were thermal fusion bonded to each other. As the outer package member 20, an aluminum laminated film was used in which a surface protective layer (a nylon film having a thickness of 25 μm), a metal layer (an aluminum foil having a thickness of 40 μm), and a fusion-bonding layer (a polypropylene film having a thickness of 30 μm) were stacked in this order. In this case, the sealing film 31 (a polypropylene film having a thickness of 5 μm) was interposed between the outer package member 20 and the positive electrode lead 11, and the sealing film 32 (a polypropylene film having a thickness of 5 μm) was interposed between the outer package member 20 and the negative electrode lead 12.

Lastly, the electrolytic solution was injected into the outer package member 20 and thereafter, the outer edges of one of the remaining sides of the outer package member 20 were thermal fusion bonded to each other in a reduced-pressure environment. Thus, the wound body was impregnated with the electrolytic solution, thereby forming the wound electrode body 10 and sealing the wound electrode body 10 in the outer package member 20. As a result, the laminated secondary battery was completed.

Evaluation of battery characteristics of the secondary batteries revealed the results described in Table 18. A capacity retention characteristic, a high-temperature cyclability characteristic, a high-temperature swelling characteristic, and a crack durability were evaluated here as the battery characteristics.

In a case of examining the capacity retention characteristic, first, the secondary battery was charged and discharged for one cycle in an ambient temperature environment (at a temperature of 23° C.) in order to stabilize a state of the secondary battery. Upon charging, the secondary battery was charged with a constant current of 0.2 C until a battery voltage reached the charge voltage Ec (4.38 V or 4.45 V), and was thereafter charged with a constant voltage of the battery voltage corresponding to the charge voltage Ec until a current reached 0.05 C. Upon discharging, the secondary battery was discharged with a constant current of 0.2 C until a battery voltage reached the discharge voltage Ed (3.00 V). It should be understood that 0.2 C and 0.05 C are values of currents that cause battery capacities (theoretical capacities) to be completely discharged in 5 hours and 20 hours, respectively.

Thereafter, the secondary battery was charged and discharged for another cycle in the same environment and in the above-described charging and discharging conditions to thereby measure a discharge capacity (a discharge capacity before varying the charge voltage Ec). Thereafter, the secondary battery was charged and discharged for another cycle in the same environment and in similar charging and discharging conditions except that the charge voltage Ec was lowered by 10 mV to thereby measure a discharge capacity (a discharge capacity after varying the charge voltage Ec). Lastly, the following was calculated: capacity variation rate (%)=[(discharge capacity before varying charge voltage Ec−discharge capacity after varying charge voltage Ec)/discharge capacity before varying charge voltage Ec]×100.

In a case of examining the high-temperature cyclability characteristic, the state of the secondary battery was stabilized by the above procedures, following which the secondary battery was charged and discharged for one cycle in an ambient temperature environment (at a temperature of 23° C.) to thereby measure a second-cycle discharge capacity. Thereafter, the secondary battery was charged and discharged for another 700 cycles in a high temperature environment (at a temperature of 45° C.) to thereby measure a 702nd-cycle discharge capacity. Lastly, the following was calculated: high-temperature retention rate (%)=(702nd-cycle discharge capacity/second-cycle discharge capacity)×100. Charging and discharging conditions were similar to those for the case of examining the capacity retention characteristic, except that the current at the time of charging was changed to 0.7 C and that the current at the time of discharging was changed to 1 C. It should be understood that 0.7 C and 1 C are values of currents that cause battery capacities (theoretical capacities) to be completely discharged in 10/7 hours and 1 hour, respectively.

In a case of examining the high-temperature swelling characteristic, in the above-described procedures of examining the high-temperature cyclability characteristic, a thickness (a second-cycle thickness) of the secondary battery was measured at the time of measuring the second-cycle discharge capacity, and a thickness (a 702nd-cycle thickness) of the secondary battery was measured at the time of measuring the 702nd-cycle discharge capacity. Thus, the following was calculated: swelling increase rate (%)=[(702nd-cycle thickness−second-cycle thickness)/second-cycle thickness]×100.

In a case of examining the crack durability, after the examination of the above-described high-temperature cyclability characteristic, the secondary battery was disassembled to thereby collect the positive electrode 13. Thereafter, a state of the positive electrode 13 (the positive electrode active material layer 13B) in a region corresponding to the curved part 10R was confirmed by visual observation, to thereby examine the crack occurrence.

TABLE 18

Positive electrode active material: LiCoO$_2$, Negative electrode active material: artificial graphite

| Experiment example | Charge voltage Ec (V) | Negative electrode potential Ef (mV) | Negative electrode potential variation Ev (mV) | Capacity variation rate (%) | High-temperature retention rate (%) | Swelling increase rate (%) | Crack occurrence |
|---|---|---|---|---|---|---|---|
| 13-1 | 4.38 | 86 | 1 | 2.0 | 61 | 28 | Yes |
| 13-2 |  | 80 | 3 | 1.6 | 63 | 26 | Yes |
| 13-3 |  | 68 | 9 | 1.2 | 65 | 25 | Yes |
| 13-4 |  | 50 | 17 | 0.8 | 68 | 24 | Yes |
| 13-5 |  | 19 | 28 | 0.6 | 71 | 24 | Yes |

TABLE 18-continued

Positive electrode active material: LiCoO₂, Negative
electrode active material: artificial graphite

| Experiment example | Charge voltage Ec (V) | Negative electrode potential Ef (mV) | Negative electrode potential variation Ev (mV) | Capacity variation rate (%) | High-temperature retention rate (%) | Swelling increase rate (%) | Crack occurrence |
|---|---|---|---|---|---|---|---|
| 13-6 | 4.45 | 86 | 1 | 1.0 | 47 | 39 | Yes |
| 13-7 | | 80 | 3 | 0.9 | 50 | 38 | Yes |
| 13-8 | | 66 | 10 | 0.8 | 52 | 36 | Yes |
| 13-9 | | 34 | 23 | 0.7 | 63 | 26 | Yes |
| 13-10 | | 19 | 28 | 0.7 | 64 | 25 | Yes |
| 13-11 | 4.38 | 12 | 15 | 0.7 | 58 | 25 | Yes |
| 13-12 | | 87 | <1 | 2.1 | 60 | 29 | Yes |
| 13-13 | | 88 | <1 | 2.2 | 59 | 28 | Yes |
| 13-14 | | 90 | <1 | 2.3 | 56 | 27 | Yes |
| 13-15 | | 91 | <1 | 2.5 | 50 | 38 | Yes |
| 13-16 | 4.45 | 14 | 18 | 0.6 | 33 | 57 | Yes |
| 13-17 | | 87 | <1 | 1.1 | 35 | 59 | Yes |
| 13-18 | | 89 | <1 | 1.2 | 34 | 58 | Yes |
| 13-19 | | 90 | <1 | 1.5 | 32 | 57 | Yes |
| 13-20 | | 92 | <1 | 1.7 | 29 | 62 | Yes |

As described in Table 18, in the case where the positive electrode 13 included the positive electrode active material (the layered rock-salt lithium-cobalt composite oxide) and the negative electrode 14 included the negative electrode active material (graphite), and where the charge voltage Ec is set to higher than or equal to 4.38 V, each of the capacity variation rate, the high-temperature retention rate, and the swelling increase rate varied depending on the negative electrode potential Ef and the negative electrode potential variation Ev.

Specifically, in a case where two configuration conditions, i.e., the negative electrode potential Ef being from 19 mV to 86 mV both inclusive and the negative electrode potential variation Ev being greater than or equal to 1 mV, were satisfied together (Experiment examples 13-1 to 13-10), the capacity variation rate and the swelling increase rate each decreased slightly in some cases and the high-temperature retention rate decreased slightly in some cases, as compared with a case where the two configuration conditions were not satisfied together (Experiment examples 13-11 to 13-20). However, each of the capacity variation rate, the high-temperature retention rate, and the swelling increase rate obtained in a case where only the two configuration conditions were satisfied was not satisfactory.

In addition, in the case where only the two configuration conditions (the negative electrode potential Ef and the negative electrode potential variation Ev) were satisfied, the crack occurred.

Experiment Examples 14-1 to 14-35

As described in Tables 19 and 20, secondary batteries were fabricated following which the battery characteristics of the secondary batteries were examined by similar procedures except that the degree of durability was changed. In this case, the area density and the volume density of the positive electrode active material layer 13B were each changed and the piercing strength of the positive electrode 13 was changed depending on a thickness of the positive electrode current collector 13A, to thereby vary the degree of durability. The thickness of the positive electrode current collector 13A was varied in a range from 12 μm to 18 μm both inclusive.

TABLE 19

Charge voltage Ec = 4.38 V, Negative electrode potential Ef = 50 mV,
Negative electrode potential variation Ev = 17 mV

| Experiment example | Area density (mg/cm²) | Volume density (g/cm³) | Piercing strength (N) | Degree of durability | Capacity variation rate (%) | High-temperature retention rate (%) | Swelling increase rate (%) | Crack occurrence |
|---|---|---|---|---|---|---|---|---|
| 13-4 | 42.9 | 4.2 | 0.8 | 225 | 0.8 | 68.0 | 24.0 | Yes |
| 14-1 | 40.0 | 4.2 | 0.8 | 210 | 0.8 | 68.6 | 23.6 | Yes |
| 14-2 | 38.1 | 4.2 | 0.8 | 200 | 0.8 | 68.9 | 23.8 | No |
| 14-3 | 35.0 | 4.2 | 0.8 | 184 | 0.8 | 69.1 | 23.6 | No |
| 14-4 | 32.0 | 4.2 | 0.8 | 168 | 0.8 | 69.6 | 23.6 | No |
| 14-5 | 26.7 | 4.2 | 0.8 | 140 | 0.8 | 69.4 | 23.5 | No |
| 14-6 | 20.0 | 4.2 | 0.8 | 105 | 0.8 | 70.2 | 23.4 | No |
| 14-7 | 45.0 | 4.0 | 0.8 | 225 | 0.8 | 67.9 | 23.1 | Yes |
| 14-8 | 42.0 | 4.0 | 0.8 | 210 | 0.8 | 68.8 | 23.2 | Yes |
| 14-9 | 40.0 | 4.0 | 0.8 | 200 | 0.8 | 69.1 | 23.5 | No |
| 14-10 | 38.8 | 4.0 | 0.8 | 194 | 0.8 | 68.6 | 23.6 | No |
| 14-11 | 36.8 | 4.0 | 0.8 | 184 | 0.8 | 68.2 | 23.8 | No |
| 14-12 | 44.2 | 3.8 | 0.8 | 210 | 0.8 | 68.8 | 23.3 | Yes |
| 14-13 | 42.1 | 3.8 | 0.8 | 200 | 0.8 | 68.3 | 23.5 | No |

TABLE 19-continued

Charge voltage Ec = 4.38 V, Negative electrode potential Ef = 50 mV,
Negative electrode potential variation Ev = 17 mV

| Experiment example | Area density (mg/cm$^2$) | Volume density (g/cm$^3$) | Piercing strength (N) | Degree of dura- bility | Capacity variation rate (%) | High- temperature retention rate (%) | Swelling increase rate (%) | Crack occurrence |
|---|---|---|---|---|---|---|---|---|
| 14-14 | 40.8 | 3.8 | 0.8 | 194 | 0.8 | 68.3 | 23.2 | No |
| 14-15 | 38.7 | 3.8 | 0.8 | 184 | 0.8 | 69.0 | 23.7 | No |
| 14-16 | 44.3 | 3.5 | 0.8 | 194 | 0.8 | 68.0 | 22.9 | No |
| 14-17 | 42.1 | 3.5 | 0.8 | 184 | 0.8 | 68.8 | 23.3 | No |
| 14-18 | 44.2 | 4.3 | 0.9 | 211 | 0.8 | 68.8 | 23.3 | Yes |
| 14-19 | 42.1 | 4.3 | 0.9 | 201 | 0.8 | 68.8 | 23.4 | Yes |
| 14-20 | 45.0 | 4.2 | 0.9 | 210 | 0.8 | 68.6 | 23.0 | Yes |
| 14-21 | 42.9 | 4.2 | 0.9 | 200 | 0.8 | 68.3 | 23.1 | No |
| 14-22 | 41.6 | 4.2 | 0.9 | 194 | 0.8 | 68.3 | 23.4 | No |
| 14-23 | 39.4 | 4.2 | 0.9 | 184 | 0.8 | 68.9 | 23.5 | No |

TABLE 20

Charge voltage Ec = 4.38 V, Negative electrode potential Ef = 50 mV,
Negative electrode potential variation Ev = 17 mV

| Experi- ment example | Area density (mg/cm$^2$) | Volume density (g/cm$^3$) | Piercing strength (N) | Degree of dura- bility | Capacity variation rate (%) | High- temperature retention rate (%) | Swelling increase rate (%) | Crack occur- rence |
|---|---|---|---|---|---|---|---|---|
| 14-24 | 45.0 | 4.0 | 0.9 | 200 | 0.8 | 68.1 | 23.2 | No |
| 14-25 | 43.7 | 4.0 | 0.9 | 194 | 0.8 | 68.7 | 23.1 | No |
| 14-26 | 41.4 | 4.0 | 0.9 | 184 | 0.8 | 69.0 | 23.5 | No |
| 14-27 | 49.3 | 4.3 | 1.0 | 212 | 0.8 | 65.6 | 24.1 | Yes |
| 14-28 | 47.0 | 4.3 | 1.0 | 202 | 0.8 | 66.6 | 23.9 | Yes |
| 14-29 | 44.7 | 4.3 | 1.0 | 192 | 0.8 | 68.2 | 22.9 | No |
| 14-30 | 42.8 | 4.3 | 1.0 | 184 | 0.8 | 68.5 | 23.3 | No |
| 14-31 | 39.5 | 4.3 | 1.0 | 170 | 0.8 | 68.9 | 23.5 | No |
| 14-32 | 50.0 | 4.3 | 1.2 | 179 | 0.8 | 64.9 | 23.9 | No |
| 14-33 | 44.9 | 4.3 | 1.2 | 161 | 0.8 | 68.7 | 23.0 | No |
| 14-34 | 43.3 | 4.3 | 1.2 | 155 | 0.8 | 68.3 | 23.0 | No |
| 14-35 | 39.9 | 4.3 | 1.2 | 143 | 0.8 | 68.7 | 23.3 | No |

In the case where the two configuration conditions (the negative electrode potential Ef and the negative electrode potential variation Ev) were satisfied (Experiment examples 13-4 and 14-1 to 14-35), the crack occurrence state varied depending on the degree of durability.

Specifically, in a case where a configuration condition, i.e., the degree of durability being less than or equal to 200, was further satisfied (for example, Experiment examples 14-2 to 14-6): no crack occurred, the capacity variation rate and the swelling increase rate each decreased sufficiently, and the high-temperature retention rate increased sufficiently, as compared with a case where the configuration condition was not satisfied (for example, Experiment examples 13-4 and 14-1). In particular, in a case where the degree of durability was less than or equal to 200, occurrence of the crack was prevented stably if the area density was from 20.0 mg/cm$^2$ to 50.0 mg/cm$^2$ both inclusive and the volume density was from 3.5 g/cm$^3$ to 4.3 g/cm$^3$ both inclusive.

Based upon the results described in Tables 18 to 20, in the case where the wound electrode body 10 had an elongated shape, the positive electrode 13 included the positive electrode active material (the layered rock-salt lithium-cobalt composite oxide), and the negative electrode 14 included the negative electrode active material (graphite), and where the above-described three configuration conditions (the negative electrode potential Ef, the negative electrode potential varia- tion Ev, and the degree of durability) were satisfied: the capacity retention characteristic, the high-temperature cyclability characteristic, and the high-temperature swelling characteristic were each improved while securing the crack durability. Accordingly, superior battery characteristics of the secondary batteries were obtained.

Experiment Examples 15-1 to 15-20

Next, laminated secondary batteries (lithium-ion secondary batteries) illustrated in FIGS. 1 and 2 were fabricated, following which battery characteristics of the secondary batteries were evaluated as described below.

In a case of fabricating the positive electrode 13, first, 91 parts by mass of the positive electrode active material (lithium cobalt oxide (LiCoO$_2$) serving as the layered rock-salt lithium-cobalt composite oxide), 3 parts by mass of the positive electrode binder (polyvinylidene difluoride), and 6 parts by mass of the positive electrode conductor (graphite) were mixed with each other to thereby obtain a positive electrode mixture. Thereafter, the positive electrode mixture was put into an organic solvent (N-methyl-2-pyrrolidone), following which the organic solvent was stirred to thereby prepare a paste positive electrode mixture slurry. Thereafter, the positive electrode mixture slurry was applied on both sides of the positive electrode current collector 13A (a band-shaped aluminum foil having a thickness of 12 μm) by means of a coating apparatus, following which the applied positive electrode mixture slurry was dried to thereby form the positive electrode active material layers 13B. Lastly, the positive electrode active material layers 13B were compression-molded by means of a roll pressing machine.

In a case of fabricating the negative electrode 14, first, 97 parts by mass of the negative electrode active material (artificial graphite), and 1.5 parts by mass of the negative electrode binder (sodium carboxymethyl cellulose) were mixed with each other to thereby obtain a negative electrode mixture precursor. Thereafter, the negative electrode mixture precursor was put into an aqueous solvent (deionized water), following which 1.5 parts by mass, in terms of solid content, of the negative electrode binder (a styrene-butadiene-rubber dispersion liquid) was put into the aqueous solvent to thereby prepare a paste negative electrode mixture slurry. Thereafter, the negative electrode mixture slurry was applied on both sides of the negative electrode current collector 14A (a band-shaped copper foil having a thickness of 15 μm) by means of a coating apparatus, following which the applied negative electrode mixture slurry was dried to thereby form the negative electrode active material layers 14B. Lastly, the negative electrode active material layers 14B were compression-molded by means of a roll pressing machine.

In the case of fabricating the positive electrode 13 and the negative electrode 14, a mixture ratio (a weight ratio) between the positive electrode active material and the negative electrode active material was adjusted to thereby vary each of the negative electrode potential Ef (mV) and the negative electrode potential variation Ev (mV). Each of the negative electrode potential Ef and the negative electrode potential variation Ev in the case where the charge voltage Ec was set to 4.38 V or 4.45 V was as described in Table 21. Here, the maximum discharge capacity was set to 1950 mAh to 2050 mAh both inclusive.

In a case of preparing the electrolytic solution, the electrolyte salt (lithium hexafluorophosphate) was added to a solvent (ethylene carbonate, propylene carbonate, and diethyl carbonate), following which the solvent was stirred. In this case, a mixture ratio (a weight ratio) of ethylene carbonate/propylene carbonate/diethyl carbonate in the solvent was set to 15:15:70, and a content of the electrolyte salt with respect to the solvent was set to 1.2 mol/kg.

In a case of assembling the secondary battery, first, the positive electrode lead 11 including aluminum was welded to the positive electrode current collector 13A, and the negative electrode lead 12 including copper was welded to the negative electrode current collector 14A. Thereafter, the positive electrode 13 and the negative electrode 14 were stacked on each other with the separator 15 (a fine-porous polyethylene film having a thickness of 15 μm) interposed therebetween to thereby obtain a stacked body. Thereafter, the stacked body was wound, following which the protective tape was attached to a surface of the stacked body to thereby obtain a wound body.

Thereafter, the outer package member 20 was folded in such a manner as to sandwich the wound body, following which the outer edges of two sides of the outer package member 20 were thermal fusion bonded to each other. As the outer package member 20, an aluminum laminated film was used in which a surface protective layer (a nylon film having a thickness of 25 μm), a metal layer (an aluminum foil having a thickness of 40 μm), and a fusion-bonding layer (a polypropylene film having a thickness of 30 μm) were stacked in this order. In this case, the sealing film 31 (a polypropylene film having a thickness of 5 μm) was interposed between the outer package member 20 and the positive electrode lead 11, and the sealing film 32 (a polypropylene film having a thickness of 5 μm) was interposed between the outer package member 20 and the negative electrode lead 12.

Lastly, the electrolytic solution was injected into the outer package member 20 and thereafter, the outer edges of one of the remaining sides of the outer package member 20 were thermal fusion bonded to each other in a reduced-pressure environment. Thus, the wound body was impregnated with the electrolytic solution, thereby forming the wound electrode body 10 and sealing the wound electrode body 10 in the outer package member 20. As a result, the laminated secondary battery was completed.

In the case of fabricating the secondary battery, the secondary battery was not hot-pressed. The completed secondary battery was disassembled to thereby calculate the adhesive strengths FC and FA (mN/mm). The adhesive strengths FC and FA were 4 mN/mm.

Evaluation of battery characteristics of the secondary batteries revealed the results described in Table 21. A capacity retention characteristic, a high-temperature cyclability characteristic, and a high-temperature swelling characteristic were evaluated here as the battery characteristics.

In a case of examining the capacity retention characteristic, first, the secondary battery was charged and discharged for one cycle in an ambient temperature environment (at a temperature of 23° C.) in order to stabilize a state of the secondary battery. Upon charging, the secondary battery was charged with a constant current of 0.2 C until a battery voltage reached the charge voltage Ec (4.38 V or 4.45 V), and was thereafter charged with a constant voltage of the battery voltage corresponding to the charge voltage Ec until a current reached 0.05 C. Upon discharging, the secondary battery was discharged with a constant current of 0.2 C until a battery voltage reached the discharge voltage Ed (3.00 V). It should be understood that 0.2 C and 0.05 C are values of currents that cause battery capacities (theoretical capacities) to be completely discharged in 5 hours and 20 hours, respectively.

Thereafter, the secondary battery was charged and discharged for another cycle in the same environment and in the above-described charging and discharging conditions to thereby measure a discharge capacity (a discharge capacity before varying the charge voltage Ec). Thereafter, the secondary battery was charged and discharged for another cycle in the same environment and in similar charging and discharging conditions except that the charge voltage Ec was lowered by 10 mV to thereby measure a discharge capacity (a discharge capacity after varying the charge voltage Ec). Lastly, the following was calculated: capacity variation rate (%)=[(discharge capacity before varying charge voltage Ec−discharge capacity after varying charge voltage Ec)/ discharge capacity before varying charge voltage Ec]×100.

In a case of examining the high-temperature cyclability characteristic, the state of the secondary battery was stabilized by the above procedures, following which the secondary battery was charged and discharged for one cycle in an ambient temperature environment (at a temperature of 23° C.) to thereby measure a second-cycle discharge capacity. Thereafter, the secondary battery was charged and discharged for another 700 cycles in a high temperature environment (at a temperature of 45° C.) to thereby measure a 702nd-cycle discharge capacity. Lastly, the following was calculated: high-temperature retention rate (%)=(702nd-cycle discharge capacity/second-cycle discharge capacity)× 100. Charging and discharging conditions were similar to those for the case of examining the capacity retention characteristic, except that the current at the time of charging was changed to 0.7 C and that the current at the time of discharging was changed to 1 C. It should be understood that 0.7 C and 1 C are values of currents that cause battery capacities (theoretical capacities) to be completely discharged in 10/7 hours and 1 hour, respectively.

In a case of examining the high-temperature swelling characteristic, in the above-described procedures of examining the high-temperature cyclability characteristic, a thickness (a second-cycle thickness) of the secondary battery was measured at the time of measuring the second-cycle discharge capacity, and a thickness (a 702nd-cycle thickness) of the secondary battery was measured at the time of measuring the 702nd-cycle discharge capacity. Thus, the following was calculated: swelling increase rate (%)=[(702nd-cycle thickness−second-cycle thickness)/second-cycle thickness]×100.

TABLE 21

Positive electrode active material: $LiCoO_2$, Negative electrode active material: artificial graphite

| Experiment example | Charge voltage Ec (V) | Negative electrode potential Ef (mV) | Negative electrode potential variation Ev (mV) | Capacity variation rate (%) | High-temperature retention rate (%) | Swelling increase rate (%) |
|---|---|---|---|---|---|---|
| 15-1 | 4.38 | 86 | 1 | 2.0 | 61.0 | 28.0 |
| 15-2 | | 80 | 3 | 1.6 | 63.0 | 26.0 |
| 15-3 | | 68 | 9 | 1.2 | 65.0 | 25.0 |
| 15-4 | | 50 | 17 | 0.8 | 68.0 | 24.0 |
| 15-5 | | 19 | 28 | 0.6 | 71.0 | 24.0 |
| 15-6 | 4.45 | 86 | 1 | 1.0 | 47.0 | 39.0 |
| 15-7 | | 80 | 3 | 0.9 | 50.0 | 38.0 |
| 15-8 | | 66 | 10 | 0.8 | 52.0 | 36.0 |
| 15-9 | | 34 | 23 | 0.7 | 63.0 | 26.0 |
| 15-10 | | 19 | 28 | 0.7 | 64.0 | 25.0 |
| 15-11 | 4.38 | 12 | 15 | 0.7 | 58.0 | 25.0 |
| 15-12 | | 87 | <1 | 2.1 | 60.0 | 29.0 |
| 15-13 | | 88 | <1 | 2.2 | 59.0 | 28.0 |
| 15-14 | | 90 | <1 | 2.3 | 56.0 | 27.0 |
| 15-15 | | 91 | <1 | 2.5 | 50.0 | 38.0 |
| 15-16 | 4.45 | 14 | 18 | 0.6 | 33.0 | 57.0 |
| 15-17 | | 87 | <1 | 1.1 | 35.0 | 59.0 |
| 15-18 | | 89 | <1 | 1.2 | 34.0 | 58.0 |
| 15-19 | | 90 | <1 | 1.5 | 32.0 | 57.0 |
| 15-20 | | 92 | <1 | 1.7 | 29.0 | 62.0 |

As described in Table 21, in the case where the positive electrode 13 included the positive electrode active material (the layered rock-salt lithium-cobalt composite oxide) and the negative electrode 14 included the negative electrode active material (graphite), and where the charge voltage Ec was set to higher than or equal to 4.38 V, each of the capacity variation rate, the high-temperature retention rate, and the swelling increase rate varied depending on the negative electrode potential Ef and the negative electrode potential variation Ev.

Specifically, in a case where two configuration conditions, i.e., the negative electrode potential Ef being from 19 mV to 86 mV both inclusive and the negative electrode potential variation Ev being greater than or equal to 1 mV, were satisfied together (Experiment examples 15-1 to 15-10), the capacity variation rate and the swelling increase rate each decreased slightly in some cases and the high-temperature retention rate increased slightly in some cases, as compared with a case where the two configuration conditions were not satisfied together (Experiment examples 15-11 to 15-20). However, each of the capacity variation rate, the high-temperature retention rate, and the swelling increase rate obtained in a case where only the two configuration conditions were satisfied was not satisfactory.

Experiment Examples 16-1 to 16-19

As described in Table 22, in the case where the two configuration conditions (the negative electrode potential Ef and the negative electrode potential variation Ev) were satisfied, secondary batteries were fabricated following which the battery characteristics of the secondary batteries were examined by similar procedures except that the adhesive strength FC and the adhesive strength FA were each changed, and that the low-temperature cyclability characteristic was newly examined.

In the case of fabricating the secondary battery, the separator 15 including the base layer 15A and the polymer compound layer 15B was used, and the secondary battery having been assembled was applied with pressure and heated using a hot press machine while performing initial-cycle charging. Charging conditions were set to those similar to the charging conditions in the case of examining the capacity retention characteristic. In this case, a temperature (of 40° C. to 90° C.) and a pressure (of 5 kgf/cm² to 50 kgf/cm²) at the time of hot pressing were adjusted to thereby vary the adhesive strength FC and the change adhesive strength FA as described in Table 22. With increase in the temperature and the pressure, the adhesive strength FC and the adhesive strength FA tended to increase.

In a case of fabricating the separator 15 including the base layer 15A and the polymer compound layer 15B, first, a polymer compound (polyvinylidene difluoride) was added to an organic solvent (N-methyl-2-pyrrolidone), following which the organic solvent was stirred to thereby prepare a precursor solution. In this case, a concentration of the polymer compound in the precursor solution was set to 20 wt %. Thereafter, the precursor solution was applied on one side of the base layer 15A (a fine-porous polyethylene film having a thickness of 12 μm), following which the precursor solution was dried to thereby form the polymer compound layer 15B (the positive electrode-side polymer compound layer 15BX). Lastly, the precursor solution was applied on the other side of the base layer 15A, following which the precursor solution was dried to thereby form the polymer compound layer 15B (the negative electrode-side polymer compound layer 15BY).

In order to vary only one of the adhesive strengths FC and FA, the respective forming amounts of the positive electrode-side polymer compound layer 15BX and the negative electrode-side polymer compound layer 15BY were appropriately adjusted.

In a case of examining the low-temperature cyclability characteristic, the state of the secondary battery was stabilized by the above procedures, following which the secondary battery was charged and discharged for one cycle in an ambient temperature environment (at a temperature of 23° C.) to thereby measure the second-cycle discharge capacity. Thereafter, the secondary battery was charged and discharged for another 100 cycles in a low temperature environment (at a temperature of 0° C.) to thereby measure a 102nd-cycle discharge capacity. Lastly, the following was calculated: low-temperature retention rate (%)=(102nd-cycle discharge capacity/second-cycle discharge capacity)×100. Charging and discharging conditions were similar to those for the case of examining the capacity retention characteristic, except that the current at the time of charging was changed to 0.5 C and that the current at the time of discharging was changed to 0.5 C.

TABLE 22

Charge voltage Ec = 4.38 V, Negative electrode potential Ef = 50 mV, Negative electrode potential variation Ev = 17 mV

| Experiment example | Positive electrode Adhesive strength FC (mN/mm) | Negative electrode Adhesive strength FA (mN/mm) | Capacity variation rate (%) | High-temperature retention rate (%) | Swelling increase rate (%) | Low-temperature retention rate (%) |
|---|---|---|---|---|---|---|
| 15-4 | 4 | 4 | 0.8 | 68.0 | 24.0 | 38.9 |
| 16-1 | 5 | 5 | 0.8 | 78.6 | 8.4 | 77.1 |
| 16-2 | 10 | 10 | 0.8 | 82.0 | 7.4 | 80.6 |
| 16-3 | 20 | 20 | 0.8 | 86.1 | 7.2 | 82.6 |
| 16-4 | 35 | 40 | 0.8 | 84.8 | 7.6 | 82.0 |
| 16-5 | 50 | 70 | 0.8 | 82.7 | 8.0 | 80.8 |
| 16-6 | 100 | 100 | 0.8 | 81.3 | 9.2 | 79.5 |
| 16-7 | 110 | 110 | 0.8 | 63.1 | 18.7 | 66.9 |
| 16-8 | 4 | 5 | 0.8 | 74.9 | 12.2 | 68.5 |
| 16-9 | 4 | 10 | 0.8 | 74.5 | 12.0 | 74.7 |
| 16-10 | 4 | 20 | 0.8 | 75.6 | 10.4 | 77.7 |
| 16-11 | 4 | 40 | 0.8 | 76.3 | 11.3 | 78.7 |
| 16-12 | 4 | 70 | 0.8 | 76.7 | 10.8 | 76.1 |
| 16-13 | 4 | 100 | 0.8 | 75.2 | 11.6 | 75.1 |
| 16-14 | 110 | 5 | 0.8 | 75.8 | 12.6 | 70.5 |
| 16-15 | 110 | 10 | 0.8 | 76.2 | 10.9 | 73.6 |
| 16-16 | 110 | 20 | 0.8 | 77.7 | 10.3 | 76.3 |
| 16-17 | 110 | 40 | 0.8 | 78.2 | 11.3 | 77.9 |
| 16-18 | 110 | 70 | 0.8 | 75.9 | 11.8 | 76.9 |
| 16-19 | 110 | 100 | 0.8 | 72.7 | 12.6 | 73.0 |

In the case where the two configuration conditions (the negative electrode potential Ef and the negative electrode potential variation Ev) were satisfied (Experiment examples 15-4 and 16-1 to 16-19), the capacity variation rate, the high-temperature retention rate, the swelling increase rate, and the low-temperature retention rate each varied depending on the adhesive strengths FC and FA.

Specifically, in a case where a configuration condition, i.e., each of the adhesive strengths FC and FA being from 5 mN/mm to 100 mN/mm both inclusive, was satisfied (Experiment examples 16-1 to 16-6): the high-temperature retention rate and the low-temperature retention rate each increased sufficiently, and the capacity variation rate and the swelling increase rate each decreased sufficiently, as compared with a case where the configuration condition was not satisfied (Experiment examples 15-4, 16-1, and 16-7).

Further, also in a case where a configuration condition, i.e., only the adhesive strength FA being from 5 mN/mm to 100 mN/mm both inclusive, was satisfied (Experiment examples 16-8 to 16-19): the high-temperature retention rate and the low-temperature retention rate each increased sufficiently, and the capacity variation rate and the swelling increase rate each decreased sufficiently, as compared with a case where the configuration condition was not satisfied for both of the adhesive strengths FC and FA (Experiment examples 15-4, 16-1, and 16-7).

However, in the case where the configuration condition was satisfied for both of the adhesive strengths FC and FA, the high-temperature retention rate and the low-temperature retention rate each further increased and the capacity variation rate and the swelling increase rate each further decreased, as compared with the case where the configuration condition was satisfied for only the adhesive strength FA.

In particular, in a case where three configuration conditions (the negative electrode potential Ef, the negative electrode potential variation Ev, and the adhesive strength FA) were satisfied, if the adhesive strength FA was from 10 mN/mm to 40 mN/mm both inclusive, the high-temperature retention rate and the low-temperature retention rate each further increased and the swelling increase rate further decreased. In addition, also in a case where four configuration conditions (the negative electrode potential Ef, the negative electrode potential variation Ev, and the adhesive strengths FC and FA) were satisfied, similar tendencies were obtained.

Based upon the results described in Tables 21 and 22, in the case where the positive electrode 13 included the positive electrode active material (the layered rock-salt lithium-cobalt composite oxide), the negative electrode 14 included the negative electrode active material (graphite), and the separator 15 was adhered to the negative electrode active material layer 14B, and where the above-described three configuration conditions (the negative electrode potential Ef, the negative electrode potential variation Ev, and the adhesive strength FA) were satisfied: the capacity retention characteristic, the high-temperature cyclability characteristic, and the high-temperature swelling characteristic were each improved. Accordingly, superior battery characteristics of the secondary batteries were obtained.

Experiment Examples 17-1 to 17-20

Lastly, laminated secondary batteries (lithium-ion secondary batteries) illustrated in FIGS. 1 and 2 were fabricated, following which battery characteristics of the secondary batteries were evaluated as described below.

In a case of fabricating the positive electrode 13, first, 91 parts by mass of the positive electrode active material (lithium cobalt oxide ($LiCoO_2$) serving as the layered rock-salt lithium-cobalt composite oxide), 3 parts by mass of the positive electrode binder (polyvinylidene difluoride), and 6 parts by mass of the positive electrode conductor (graphite) were mixed with each other to thereby obtain a positive electrode mixture. Thereafter, the positive electrode mixture was put into an organic solvent (N-methyl-2-pyrrolidone), following which the organic solvent was stirred to thereby prepare a paste positive electrode mixture slurry. Thereafter, the positive electrode mixture slurry was applied on both sides of the positive electrode current collector 13A (a band-shaped aluminum foil having a thickness of 12 μm) by means of a coating apparatus, following which the applied positive electrode mixture slurry was dried to thereby form the positive electrode active material layers 13B. Lastly, the positive electrode active material layers 13B were compression-molded by means of a roll pressing machine.

In a case of fabricating the negative electrode 14, first, 97 parts by mass of the negative electrode active material (artificial graphite having a median diameter D50 of 10 μm and spacing S of the (002) plane of 0.3360 μm), and 1.5 parts by mass of the negative electrode binder (sodium carboxymethyl cellulose) were mixed with each other to thereby obtain a negative electrode mixture precursor. Thereafter, the negative electrode mixture precursor was put into an aqueous solvent (deionized water), following which 1.5 parts by mass, in terms of solid content, of the negative electrode binder (a styrene-butadiene-rubber dispersion liquid) was put into the aqueous solvent to thereby prepare a paste negative electrode mixture slurry. Thereafter, the negative electrode mixture slurry was applied on both sides of the negative electrode current collector 14A (a band-shaped copper foil having a thickness of 15 μm) by means of a coating apparatus, following which the applied negative electrode mixture slurry was dried to thereby form the negative electrode active material layers 14B. Lastly, the negative electrode active material layers 14B were compression-molded by means of a roll pressing machine.

In the case of fabricating the positive electrode 13 and the negative electrode 14, a mixture ratio (a weight ratio) between the positive electrode active material and the negative electrode active material was adjusted to thereby vary each of the negative electrode potential Ef (mV) and the negative electrode potential variation Ev (mV). Each of the negative electrode potential Ef and the negative electrode potential variation Ev in the case where the charge voltage Ec was set to 4.38 V or 4.45 V was as described in Table 23. Here, the maximum discharge capacity was set to 1950 mAh to 2050 mAh both inclusive.

In a case of preparing the electrolytic solution, the electrolyte salt (lithium hexafluorophosphate) was added to a solvent (carbonate ester), following which the solvent was stirred. In this case, the cyclic carbonate ester (ethylene carbonate (EC)) and the chain carbonate ester (diethyl carbonate (DEC)) were used as the solvent, and a mixture ratio (volume ratio) of the solvent was set to ethylene carbonate/diethyl carbonate=20:80. A content of the electrolyte salt with respect to the solvent was set to 1.2 mol/l (=1.2 mol/dm$^3$). Thereafter, an additional solvent (vinylene carbonate serving as the unsaturated cyclic carbonate ester) was added to the solvent, and the resultant solvent was stirred. In this case, a content of the unsaturated cyclic carbonate ester in the electrolytic solution was set to 1 wt %.

In a case of assembling the secondary battery, first, the positive electrode lead 11 including aluminum was welded to the positive electrode current collector 13A, and the negative electrode lead 12 including copper was welded to the negative electrode current collector 14A. Thereafter, the positive electrode 13 and the negative electrode 14 were stacked on each other with the separator 15 (a fine-porous polyethylene film having a thickness of 15 μm) interposed therebetween to thereby obtain a stacked body. Thereafter, the stacked body was wound, following which the protective tape was attached to a surface of the stacked body to thereby obtain a wound body.

Thereafter, the outer package member 20 was folded in such a manner as to sandwich the wound body, following which the outer edges of two sides of the outer package member 20 were thermal fusion bonded to each other. As the outer package member 20, an aluminum laminated film was used in which a surface protective layer (a nylon film having a thickness of 25 μm), a metal layer (an aluminum foil having a thickness of 40 μm), and a fusion-bonding layer (a polypropylene film having a thickness of 30 μm) were stacked in this order. In this case, the sealing film 31 (a polypropylene film having a thickness of 5 μm) was interposed between the outer package member 20 and the positive electrode lead 11, and the sealing film 32 (a polypropylene film having a thickness of 5 μm) was interposed between the outer package member 20 and the negative electrode lead 12.

Lastly, the electrolytic solution was injected into the outer package member 20 and thereafter, the outer edges of one of the remaining sides of the outer package member 20 were thermal fusion bonded to each other in a reduced-pressure environment. Thus, the wound body was impregnated with the electrolytic solution, thereby forming the wound electrode body 10 and sealing the wound electrode body 10 in the outer package member 20. As a result, the laminated secondary battery was completed.

Evaluation of battery characteristics of the secondary batteries revealed the results described in Table 23. A capacity retention characteristic, a high-temperature cyclability characteristic, and a high-temperature swelling characteristic were evaluated here as the battery characteristics.

In a case of examining the capacity retention characteristic, first, the secondary battery was charged and discharged for one cycle in an ambient temperature environment (at a temperature of 23° C.) in order to stabilize a state of the secondary battery. Upon charging, the secondary battery was charged with a constant current of 0.2 C until a battery voltage reached the charge voltage Ec (4.38 V or 4.45 V), and was thereafter charged with a constant voltage of the battery voltage corresponding to the charge voltage Ec until a current reached 0.05 C. Upon discharging, the secondary battery was discharged with a constant current of 0.2 C until a battery voltage reached the discharge voltage Ed (3.00 V). It should be understood that 0.2 C and 0.05 C are values of currents that cause battery capacities (theoretical capacities) to be completely discharged in 5 hours and 20 hours, respectively.

Thereafter, the secondary battery was charged and discharged for another cycle in the same environment and in the above-described charging and discharging conditions to thereby measure a discharge capacity (a discharge capacity before varying the charge voltage Ec). Thereafter, the secondary battery was charged and discharged for another cycle in the same environment and in similar charging and discharging conditions except that the charge voltage Ec was lowered by 10 mV to thereby measure a discharge capacity (a discharge capacity after varying the charge voltage Ec). Lastly, the following was calculated: capacity variation rate (%)=[(discharge capacity before varying charge voltage Ec−discharge capacity after varying charge voltage Ec)/discharge capacity before varying charge voltage Ec]×100.

In a case of examining the high-temperature cyclability characteristic, the state of the secondary battery was stabilized by the above procedures, following which the secondary battery was charged and discharged for one cycle in an ambient temperature environment (at a temperature of 23° C.) to thereby measure a second-cycle discharge capacity. Thereafter, the secondary battery was charged and discharged for another 700 cycles in a high temperature environment (at a temperature of 45° C.) to thereby measure a 702nd-cycle discharge capacity. Lastly, the following was calculated: high-temperature retention rate (%)=(702nd-cycle discharge capacity/second-cycle discharge capacity)×100. Charging and discharging conditions were similar to those for the case of examining the capacity retention characteristic, except that the current at the time of charging was changed to 0.7 C and that the current at the time of discharging was changed to 1 C. It should be understood that 0.7 C and 1 C are values of currents that cause battery capacities (theoretical capacities) to be completely discharged in 10/7 hours and 1 hour, respectively.

In a case of examining the high-temperature swelling characteristic, in the above-described procedures of examining the high-temperature cyclability characteristic, a thickness (a second-cycle thickness) of the secondary battery was measured at the time of measuring the second-cycle discharge capacity, and a thickness (a 702nd-cycle thickness) of the secondary battery was measured at the time of measuring the 702nd-cycle discharge capacity. Thus, the following was calculated: swelling increase rate (%)=[(702nd-cycle thickness−second-cycle thickness)/second-cycle thickness]×100.

TABLE 23

Positive electrode active material: LiCoO$_2$, Negative electrode active material: artificial graphite

| Experiment example | Charge voltage Ec (V) | Negative electrode potential Ef (mV) | Negative electrode potential variation Ev (mV) | Capacity variation rate (%) | High-temperature retention rate (%) | Swelling increase rate (%) |
|---|---|---|---|---|---|---|
| 17-1 | 4.38 | 86 | 1 | 2.0 | 61 | 28 |
| 17-2 |  | 80 | 3 | 1.6 | 63 | 26 |
| 17-3 |  | 68 | 9 | 1.2 | 65 | 25 |
| 17-4 |  | 50 | 17 | 0.8 | 68 | 24 |
| 17-5 |  | 19 | 28 | 0.6 | 71 | 24 |
| 17-6 | 4.45 | 86 | 1 | 1.0 | 47 | 39 |
| 17-7 |  | 80 | 3 | 0.9 | 50 | 38 |
| 17-8 |  | 66 | 10 | 0.8 | 52 | 36 |
| 17-9 |  | 34 | 23 | 0.7 | 63 | 26 |
| 17-10 |  | 19 | 28 | 0.7 | 64 | 25 |
| 17-11 | 4.38 | 12 | 15 | 0.7 | 58 | 25 |
| 17-12 |  | 87 | <1 | 2.1 | 60 | 29 |
| 17-13 |  | 88 | <1 | 2.2 | 59 | 28 |
| 17-14 |  | 90 | <1 | 2.3 | 56 | 27 |
| 17-15 |  | 91 | <1 | 2.5 | 50 | 38 |
| 17-16 | 4.45 | 14 | 18 | 0.6 | 33 | 57 |
| 17-17 |  | 87 | <1 | 1.1 | 35 | 59 |
| 17-18 |  | 89 | <1 | 1.2 | 34 | 58 |
| 17-19 |  | 90 | <1 | 1.5 | 32 | 57 |
| 17-20 |  | 92 | <1 | 1.7 | 29 | 62 |

As described in Table 23, in the case where the positive electrode 13 included the positive electrode active material (the layered rock-salt lithium-cobalt composite oxide) and the negative electrode 14 included the negative electrode active material (graphite), and where the charge voltage Ec was set to higher than or equal to 4.38 V, each of the capacity variation rate, the high-temperature retention rate, and the swelling increase rate varied depending on the negative electrode potential Ef and the negative electrode potential variation Ev.

Specifically, in a case where two configuration conditions, i.e., the negative electrode potential Ef being from 19 m V to 86 mV both inclusive and the negative electrode potential variation Ev being greater than or equal to 1 mV, were satisfied together (Experiment examples 17-1 to 17-10), the capacity variation rate and the swelling increase rate each decreased slightly and the high-temperature retention rate increased slightly, as compared with a case where the two configuration conditions were not satisfied together (Experiment examples 17-11 to 17-20). However, each of the capacity variation rate, the high-temperature retention rate, and the swelling increase rate obtained in a case where only the two configuration conditions were satisfied was not satisfactory.

Experiment Examples 18-1 to 18-18

As described in Tables 24 and 25, in the case where the two configuration conditions (the negative electrode potential Ef and the negative electrode potential variation Ev) were satisfied, secondary batteries were fabricated following which the battery characteristics of the secondary batteries were examined by similar procedures except that the composition of the electrolytic solution was changed and that the low-temperature cyclability characteristic was newly examined.

In the case of preparing the electrolytic solution, a ratio (vol %) of the carbonate ester (the cyclic carbonate ester and the chain carbonate ester) was changed, and the lactone (γ-butyrolactone (GBL)) and the chain carboxylate ester (propyl propionate (PP), ethyl propionate (EP), and methyl propionate (MP)) were newly used as solvents. In this case, a mixture ratio (a volume ratio) between the carbonate ester, the lactone, and the chain carboxylate ester was adjusted to thereby vary the ratio (vol %) of the chain carboxylate ester as illustrated in Tables 24 and 25.

In a case of preparing the electrolytic solution, the dinitrile compound (succinonitrile (SN)), the halogenated carbonate ester (4-fluoro-1,3-dioxane-2-one (FEC)), the boron-containing lithium salt (the lithium tetrafluoroborate (LiBF$_4$)), and the dioxane compound (1,3-dioxane (DOX)) were newly used. The respective contents (wt %) of the dinitrile compound, the halogenated carbonate ester, and the dioxane compound in the electrolytic solution and the content (mol/dm$^3$) of the boron-containing lithium salt in the electrolytic solution were as described in Tables 24 and 25.

In a case of examining the low-temperature cyclability characteristic, the state of the secondary battery was stabilized by the above procedures, following which the secondary battery was charged and discharged for one cycle in an ambient temperature environment (at a temperature of 23° C.) to thereby measure the second-cycle discharge capacity. Thereafter, the secondary battery was charged and discharged for another 100 cycles in a low temperature environment (at a temperature of 0° C.) to thereby measure a 102nd-cycle discharge capacity. Lastly, the following was calculated: low-temperature retention rate (%)=(102nd-cycle discharge capacity/second-cycle discharge capacity)× 100. Charging and discharging conditions were similar to those for the case of examining the capacity retention characteristic, except that the current at the time of charging was changed to 0.5 C and that the current at the time of discharging was changed to 0.5 C.

TABLE 24

Charge voltage Ec = 4.38 V, Negative electrode potential Ef = 50 mV, Negative electrode potential variation Ev = 17 mV

| Experiment example | Carbonate ester Kind | Ratio (vol %) | Lactone Kind | Ratio (vol %) | Chain carboxylate ester Kind | Ratio (vol %) | Capacity variation rate (%) | High-temperature retention rate (%) | Swelling increase rate (%) | Low-temperature retention rate (%) |
|---|---|---|---|---|---|---|---|---|---|---|
| 17-4 | EC | 20 | DEC | 80 | — | — | 0.8 | 68 | 24 | 55 |
| 18-1 | EC | 20 | DEC | 75 | PP | 5 | 0.8 | 71 | 22 | 58 |
| 18-2 | EC | 20 | DEC | 70 | PP | 10 | 0.8 | 78 | 17 | 65 |
| 18-3 | EC | 20 | DEC | 40 | PP | 40 | 0.8 | 80 | 15 | 67 |
| 18-4 | EC | 20 | — | — | PP | 80 | 0.8 | 83 | 16 | 70 |
| 18-5 | EC | 10 | — | — | PP | 90 | 0.8 | 58 | 19 | 50 |

TABLE 24-continued

Charge voltage Ec = 4.38 V, Negative electrode potential Ef = 50 mV,
Negative electrode potential variation Ev = 17 mV

| Experiment example | Carbonate ester Kind | Ratio (vol %) | Lactone Kind | Ratio (vol %) | Chain carboxylate ester Kind | Ratio (vol %) | Capacity variation rate (%) | High-temperature retention rate (%) | Swelling increase rate (%) | Low-temperature retention rate (%) |
|---|---|---|---|---|---|---|---|---|---|---|
| 18-6 | EC | 20 | DEC | 70 | EP | 10 | 0.8 | 79 | 17 | 66 |
| 18-7 | EC | 20 | DEC | 70 | MP | 10 | 0.8 | 80 | 17 | 67 |
| 18-8 | EC | 20 | — | — | PP + EP | 10 + 70 | 0.8 | 88 | 16 | 75 |
| 18-9 | GBL | 20 | DEC | 70 | PP | 10 | 0.8 | 76 | 14 | 63 |

TABLE 25

| Experiment example | Carbonate ester Kind | Ratio (vol %) | Chain carboxylate ester Kind | Ratio (vol %) | Dinitrile compound Kind | Content (wt %) | Halogenated carbonate ester Kind | Content (wt %) | Boron-containing lithium salt Kind | Content (mol/dm$^3$) | Dioxane compound Kind | Content (wt %) | Capacity variation rate (%) | High-temperature retention rate (%) | Swelling increase rate (%) | Low-temperature retention rate (%) |
|---|---|---|---|---|---|---|---|---|---|---|---|---|---|---|---|---|
| 18-10 | EC | 20 | PP | 80 | SN | 1 | — | — | — | — | — | — | 0.8 | 85 | 15 | 72 |
| 18-11 | EC | 20 | PP | 80 | SN | 3 | — | — | — | — | — | — | 0.8 | 87 | 13 | 74 |
| 18-12 | EC | 20 | PP | 80 | SN | 20 | — | — | — | — | — | — | 0.8 | 85 | 10 | 72 |
| 18-13 | EC | 20 | PP | 80 | — | — | FEC | 1 | — | — | DOX | 0.1 | 0.8 | 85 | 16 | 72 |
| 18-14 | EC | 20 | PP | 80 | — | — | FEC | 3 | — | — | DOX | 1 | 0.8 | 87 | 16 | 74 |
| 18-15 | EC | 20 | PP | 80 | — | — | FEC | 20 | — | — | DOX | 2 | 0.8 | 93 | 18 | 80 |
| 18-16 | EC | 20 | PP | 80 | — | — | — | — | LiBF$_4$ | 0.1 | DOX | 0.1 | 0.8 | 86 | 16 | 72 |
| 18-17 | EC | 20 | PP | 80 | — | — | — | — | LiBF$_4$ | 1 | DOX | 1 | 0.8 | 90 | 17 | 76 |
| 18-18 | EC | 20 | PP | 80 | — | — | — | — | LiBF$_4$ | 2 | DOX | 2 | 0.8 | 94 | 18 | 81 |

In the case where the two configuration conditions (the negative electrode potential Ef and the negative electrode potential variation Ev) were satisfied (Experiment examples 17-4 and 18-1 to 18-5), the capacity variation rate, the high-temperature retention rate, the swelling increase rate, and the low-temperature retention rate each varied depending on the ratio of the chain carboxylate ester.

Specifically, in a case where a configuration condition, i.e., the ratio of the chain carboxylate ester being from 10 vol % to 80 vol % both inclusive, was satisfied (Experiment examples 18-2 to 18-4), the high-temperature retention rate and the low-temperature retention rate each increased sufficiently and the swelling increase rate decreased sufficiently while retaining the capacity variation rate, as compared with a case where the configuration condition was not satisfied (Experiment examples 17-4, 18-1, and 18-5).

In particular, in the case where the three configuration conditions were satisfied, advantageous tendencies to be described below were obtained.

First, in a case of using other types of chain carboxylate ester (EP and MP) (Experiment examples 18-6 to 18-8), similarly to a case of using the chain carboxylate ester (PP) (Experiment example 18-2) described above, the high-temperature retention rate and the low-temperature retention rate each increased sufficiently and the swelling increase rate decreased sufficiently, while retaining the capacity variation rate.

Second, also in a case of using the lactone (Experiment example 18-9), similarly to a case of using the carbonate ester (Experiment example 18-2), the high-temperature retention rate and the low-temperature retention rate increased sufficiently and the swelling increase rate decreased sufficiently while retaining the capacity variation rate.

Third, in a case where the electrolytic solution included the dinitrile compound (SN) and where a content of the dinitrile compound was from 1 wt % to 20 wt % both inclusive (Experiment examples 18-10 to 18-12), the high-temperature retention rate and the low-temperature retention rate each further increased and the swelling increase rate further decreased while retaining the capacity variation rate, as compared with a case where the electrolytic solution included no dinitrile compound (Experiment example 18-4).

Fourth, in a case where the electrolytic solution included the halogenated carbonate ester (FEC) and the dioxane compound (DOX) and where a content of the halogenated carbonate ester was from 1 wt % to 20 wt % both inclusive and a content of the dioxane compound was from 0.1 wt % to 2 wt % both inclusive (Experiment examples 18-13 to 18-15), the high-temperature retention rate and the low-temperature retention rate each further increased as compared with a case where the electrolytic solution did not include the halogenated carbonate ester and the dioxane compound (Experiment example 18-4).

Fifth, in a case where the electrolytic solution included the boron-containing lithium salt (LiBF$_4$) and the dioxane compound (DOX) and where a content of the lithium tetrafluoroborate was from 0.1 mol/dm$^3$ to 2 mol/dm$^3$ both inclusive, and a content of the dioxane compound was from 0.1 wt % to 2 wt % both inclusive (Experiment examples 18-16 to 18-18), the high-temperature retention rate and the low-temperature retention rate each further increased, as compared with a case where the electrolytic solution did not include lithium tetrafluoroborate and the dioxane compound dinitrile compound (Experiment example 18-4).

Experiment Examples 19-1 to 19-6

As described in Table 26, secondary batteries were fabricated following which the battery characteristics of the secondary batteries were examined by similar procedures except that the configuration of the negative electrode 14 (the median diameter D50 (μm) of the negative electrode active material (artificial graphite)) was changed.

TABLE 26

Charge voltage Ec = 4.38 V,
Negative electrode potential Ef = 50 mV,
Negative electrode potential variation Ev = 17 mV,
Solvent = EC (20 vol %) + PP (80 vol %)

| Experiment example | D50 (μm) | Capacity variation rate (%) | High-temperature retention rate (%) | Swelling increase rate (%) | Low-temperature retention rate (%) |
|---|---|---|---|---|---|
| 19-1 | 2 | 0.9 | 76 | 20 | 69 |
| 19-2 | 3.5 | 0.9 | 78 | 19 | 78 |
| 19-3 | 5 | 0.8 | 80 | 19 | 74 |
| 18-4 | 10 | 0.8 | 83 | 16 | 70 |
| 19-4 | 20 | 0.8 | 81 | 17 | 68 |
| 19-5 | 30 | 0.8 | 81 | 17 | 65 |
| 19-6 | 50 | 0.8 | 78 | 18 | 60 |

In a case where the median diameter D50 was within an appropriate range (from 3.5 μm to 30 μm both inclusive) (Experiment examples 18-4 and 19-2 to 19-5), a high high-temperature retention rate and a high low-temperature retention rate were obtained while suppressing the swelling increase rate, as compared with a case where the median diameter D50 was outside the appropriate range (Experiment examples 19-1 and 19-6). In particular, in a case where the median diameter D50 was from 5 μm to 20 μm both inclusive (Experiment examples 18-4, 19-3, and 19-4), a further higher high-temperature retention rate and a further higher low-temperature retention rate were obtained while substantially suppressing the swelling increase rate.

Experiment Examples 20-1 to 20-5

As described in Table 27, secondary batteries were fabricated following which the battery characteristics of the secondary batteries were examined by similar procedures except that the configuration of the negative electrode 14 (the spacing S (nm) of the (002) plane of the negative electrode active material (artificial graphite)) was changed.

TABLE 27

Charge voltage Ec = 4.38 V,
Negative electrode potential Ef = 50 mV,
Negative electrode potential variation Ev = 17 mV,
Solvent = EC (20 vol %) + PP (80 vol %)

| Experiment example | Spacing S (nm) | Capacity variation rate (%) | High-temperature retention rate (%) | Swelling increase rate (%) | Low-temperature retention rate (%) |
|---|---|---|---|---|---|
| 20-1 | 0.3355 | 0.9 | 77 | 19 | 65 |
| 20-2 | 0.3356 | 0.8 | 79 | 18 | 68 |
| 18-4 | 0.3360 | 0.8 | 83 | 16 | 70 |
| 20-3 | 0.3363 | 0.8 | 83 | 17 | 74 |
| 20-4 | 0.3370 | 0.7 | 85 | 17 | 76 |
| 20-5 | 0.3375 | 0.7 | 82 | 19 | 80 |

In a case where the spacing S was within an appropriate range (from 0.3355 nm to 0.3370 nm both inclusive) (Experiment examples 18-4 and 20-1 to 20-4), a high high-temperature retention rate and a high low-temperature retention rate were obtained while suppressing each of the capacity variation rate and the swelling increase rate, as compared with a case where the spacing S was outside the appropriate range (Experiment example 20-5). In particular, in a case where the spacing S was within the range of 0.3356 nm to 0.3363 nm (Experiment examples 18-4, 20-3, and 20-4), a further higher high-temperature retention rate and a further higher low-temperature retention rate were obtained while further suppressing each of the capacity variation rate and the swelling increase rate.

Based upon the results described in Tables 23 to 27, in the case where the positive electrode 13 included the positive electrode active material (the layered rock-salt lithium-cobalt composite oxide), the negative electrode 14 included the negative electrode active material (graphite), and the solvent of the electrolytic solution included the chain carboxylate ester together with the carbonate ester, the lactone, or both, and where the above-described three configuration conditions (the negative electrode potential Ef, the negative electrode potential variation Ev, and the ratio of the chain carboxylate ester) were satisfied: the capacity retention characteristic, the high-temperature cyclability characteristic, the high-temperature swelling characteristic, and the low-temperature cyclability characteristic were each improved. Accordingly, superior battery characteristics of the secondary batteries were obtained.

Although the technology has been described above with reference to some embodiments and Examples, embodiments of the technology are not limited to those described with reference to the series of embodiments and Examples above and are modifiable in a variety of ways.

Specifically, although the description has been given of the laminated secondary battery, this is non-limiting. For example, the secondary battery may be of any other type such as a cylindrical type, a prismatic type, or a coin type. Moreover, although the description has been given of a case of the battery device having a wound structure to be used in the secondary battery, this is non-limiting. For example, the battery device may have any other structure such as a stacked structure.

It should be understood that the effects described herein are mere examples, and effects of the technology are therefore not limited to those described herein. Accordingly, the technology may achieve any other effect.

It should also be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A secondary battery comprising:
 a positive electrode including a lithium-cobalt composite oxide represented by Formula (1) and having a layered rock-salt crystal structure;
 a negative electrode including graphite; and
 an electrolytic solution, wherein
 an open circuit potential, versus a lithium reference electrode, of the negative electrode measured in a full charge state is from 19 millivolts to 86 millivolts, the full charge state being a state in which the secondary battery is charged with a constant voltage of a closed circuit voltage of higher than or equal to 4.38 volts for 24 hours, and
 a potential variation of the negative electrode represented by Formula (2) is greater than or equal to 1 millivolt when the secondary battery is discharged from the full charge state by a capacity corresponding to 1 percent of a maximum discharge capacity, the maximum discharge capacity being a discharge capacity obtained when the secondary battery is discharged with a constant current from the full charge state until the closed circuit voltage reaches 3.00 volts, following which the secondary battery is discharged with a constant voltage of the closed circuit voltage of 3.00 volts for 24 hours, $$Li_xCo_{1-y}M_yO_{2-z}X_z \qquad (1)$$

wherein

M represents at least one of titanium (Ti), vanadium (V), chromium (Cr), manganese (Mn), iron (Fe), nickel (Ni), copper (Cu), sodium (Na), magnesium (Mg), aluminum (Al), silicon (Si), tin (Sn), potassium (K), calcium (Ca), zinc (Zn), gallium (Ga), strontium (Sr), yttrium (Y), zirconium (Zr), niobium (Nb), molybdenum (Mo), barium (Ba), lanthanum (La), tungsten (W), or boron (B), X represents at least one of fluorine (F), chlorine (Cl), bromine (Br), iodine (I), or sulfur (S), and x, y, and z satisfy $0.8<x<1.2$, $0\leq y<0.15$, and $0\leq z<0.05$, potential variation (millivolt(s)) of negative electrode=second negative electrode potential (millivolt(s))−first negative electrode potential (millivolt(s)) (2)

wherein the first negative electrode potential is the open circuit potential, versus the lithium reference electrode, of the negative electrode measured in the full charge state, and the second negative electrode potential is an open circuit potential, versus the lithium reference electrode, of the negative electrode measured in a state in which the secondary battery is discharged from the full charge state by the capacity corresponding to 1 percent of the maximum discharge capacity, the positive electrode includes a positive electrode active material layer, the positive electrode active material layer including a positive electrode active material and a positive electrode binder, the positive electrode active material includes the lithium-cobalt composite oxide, the positive electrode binder includes at least one of a homopolymer or a copolymer, the homopolymer and the copolymer each including vinylidene fluoride as a polymerization unit, the electrolytic solution includes a cyclic carbonate ester and at least one of a chain carbonate ester or a chain carboxylate ester, an area density of the positive electrode active material layer is greater than or equal to 36 milligrams per square centimeter, a volume density of the positive electrode active material layer is greater than or equal to 3.9 grams per cubic centimeter, a ratio of a weight of the positive electrode binder to a weight of the positive electrode active material layer is from 0.8 weight percent to 2.5 weight percent, a ratio of a weight of the cyclic carbonate ester to a sum of a weight of the chain carbonate ester and a weight of the chain carboxylate ester is greater than or equal to 0.2 and less than or equal to 1, and a content of the electrolyte salt in the electrolytic solution is from 0.7 moles per kilogram to 1.5 moles per kilogram with respect to the solvent.

2. The secondary battery according to claim 1, wherein a potential variation of the positive electrode represented by Formula (3) is greater than or equal to 2 millivolts when the secondary battery is discharged from the full charge state by the capacity corresponding to 1 percent of the maximum discharge capacity, potential variation (millivolt(s)) of positive electrode=first positive electrode potential (millivolt(s))−second positive electrode potential (millivolt(s)) (3)

wherein the first positive electrode potential is an open circuit potential, versus the lithium reference electrode, of the positive electrode measured in the full charge state, and the second positive electrode potential is an open circuit potential, versus the lithium reference electrode, of the positive electrode measured in the state in which the secondary battery is discharged from the full charge state by the capacity corresponding to 1 percent of the maximum discharge capacity.

3. The secondary battery according to claim 1, wherein the homopolymer and the copolymer each including the vinylidene fluoride as the polymerization unit include at least one of polyvinylidene difluoride, a copolymer of the vinylidene fluoride and tetrafluoroethylene, a copolymer of the vinylidene fluoride and hexafluoropropylene, or a copolymer of the vinylidene fluoride, the tetrafluoroethylene, and the hexafluoropropylene.

4. The secondary battery according to claim 3, wherein a copolymerization amount of the tetrafluoroethylene is from 0.1 weight percent to 20 weight percent, and a copolymerization amount of the hexafluoropropylene is from 0.2 weight percent to 5 weight percent.

5. The secondary battery according to claim 1, wherein the negative electrode includes a negative electrode active material layer, the negative electrode active material layer including a plurality of first negative electrode active material particles, the first negative electrode active material particles each include the graphite, a median diameter D50 of the first negative electrode active material particles is less than or equal to 20 micrometers, a volume density of the negative electrode active material layer is greater than or equal to 1.5 grams per cubic centimeter, and an integrated intensity ratio represented by Formula (8) in a case where the negative electrode active material layer is analyzed by X-ray diffractometry is less than or equal to 500, integrated intensity ratio=second integrated intensity/first integrated intensity (8)

wherein the first integrated intensity is an integrated intensity of a peak derived from a (002) plane of the graphite, and the second integrated intensity is an integrated intensity of a peak derived from a (110) plane of the graphite.

6. The secondary battery according to claim 5, wherein the negative electrode active material layer further includes a plurality of second negative electrode active material particles, and the second negative electrode active material particles each include a material including silicon as a constituent element.

7. The secondary battery according to claim 5, wherein the negative electrode active material layer further includes a plurality of second negative electrode active material particles, and wherein a ratio of mass of the second negative electrode active material particles to mass of the first negative electrode active material particles is from 0.1 mass percent to 5 mass percent.

8. The secondary battery according to claim 5, wherein the negative electrode active material layer further includes a plurality of second negative electrode active material particles, and a median diameter D50 of the second negative electrode active material particles is smaller than the median diameter D50 of the first negative electrode active material particles.

9. The secondary battery according to claim 8, wherein the negative electrode active material layer further includes a plurality of second negative electrode active material particles, and the median diameter D50 of the second negative electrode active material particles is from 1 micrometer to 10 micrometers.

10. The secondary battery according to claim 5, wherein the negative electrode active material layer further includes a plurality of second negative electrode active material particles, and at least a portion of a surface of each of the second negative electrode active material particles is covered with a carbon material.

11. The secondary battery according to claim 10, wherein the carbon material includes at least one of amorphous carbon, graphite, graphene, a carbon nanotube, or a carbon nanofiber.

12. The secondary battery according to claim 1, further comprising
a wound electrode body including the positive electrode and the negative electrode, the positive electrode and the negative electrode being wound while being separated away from each other, wherein
the wound electrode body has an elongated shape including a flat part and a pair of curved parts, the pair of curved parts opposing each other with the flat part interposed therebetween,
the positive electrode includes a positive electrode current collector and a positive electrode active material layer, the positive electrode active material layer being provided on the positive electrode current collector,
the positive electrode active material layer includes the lithium-cobalt composite oxide, and
a degree of durability of the positive electrode in the curved parts represented by Formula (12) is less than or equal to 200, degree of durability=(area density (milligram(s) per square centimeter) of positive electrode active material layer×volume density (gram(s) per cubic centimeter) of positive electrode active material layer)/piercing strength (newton(s)) of positive electrode          (12).

13. The secondary battery according to claim 1, further comprising
a separator interposed between the positive electrode and the negative electrode, wherein
the negative electrode includes a negative electrode active material layer, the negative electrode active material layer including the graphite,
the separator is adhered to the negative electrode active material layer, and
an adhesive strength of the negative electrode active material layer to the separator is from 5 millinewtons per millimeter to 100 millinewtons per meter.

14. The secondary battery according to claim 13, wherein the separator includes
a base layer, and
a first polymer compound layer provided on the base layer and adhered to the negative electrode active material layer, and
the first polymer compound layer includes a plurality of insulating particles.

15. The secondary battery according to claim 13, wherein the positive electrode includes a positive electrode active material layer, the positive electrode active material layer including the lithium-cobalt composite oxide,
the separator is adhered to the positive electrode active material layer, and
an adhesive strength of the positive electrode active material layer to the separator is from 5 millinewtons per millimeter to 100 millinewtons per meter.

16. The secondary battery according to claim 1, wherein the electrolytic solution includes a chain carboxylate ester and at least one of a carbonate ester or a lactone, and
a ratio of a volume of the chain carboxylate ester to a sum of a volume of the carbonate ester, a volume of the lactone, and a volume of the chain carboxylate ester is from 10 volume percent to 80 volume percent.

17. The secondary battery according to claim 16, wherein the chain carboxylate ester includes at least one of an acetate ester, a propionate ester, or a butyrate ester, and
a molecular weight of the chain carboxylate ester is less than or equal to 119.

18. The secondary battery according to claim 16, wherein the electrolytic solution further includes a dinitrile compound, and
a content of the dinitrile compound in the electrolytic solution is from 1 weight percent to 20 weight percent.

19. The secondary battery according to claim 16, wherein the electrolytic solution further includes a halogenated carbonate ester and a dioxane compound, the dioxane compound being represented by Formula (17),
a content of the halogenated carbonate ester in the electrolytic solution is from 1 weight percent to 20 weight percent, and
a content of the dioxane compound in the electrolytic solution is from 0.1 weight percent to 2 weight percent,

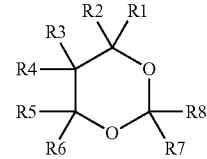

(17)

wherein each of R1 to R8 represents one of a hydrogen group and a monovalent hydrocarbon group.

* * * * *